(12) United States Patent
Wan et al.

(10) Patent No.: US 8,859,573 B2
(45) Date of Patent: Oct. 14, 2014

(54) PYRIMIDINONE AND PYRIDINONE COMPOUNDS FOR USE IN THE TREATMENT OF DISEASES OR CONDITIONS MEDIATED BY LP-PLA$_2$

(75) Inventors: Zehong Wan, Shanghai (CN); Xiaomin Zhang, Shanghai (CN); Jian Wang, Shanghai (CN); Cheng Peng, Shanghai (CN); Yun Jin, Shanghai (CN); Yimin Hu, Shanghai (CN)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 13/991,953

(22) PCT Filed: Dec. 5, 2011

(86) PCT No.: PCT/CN2011/083465
§ 371 (c)(1),
(2), (4) Date: Jun. 6, 2013

(87) PCT Pub. No.: WO2012/075917
PCT Pub. Date: Jun. 14, 2012

(65) Prior Publication Data
US 2013/0252986 A1   Sep. 26, 2013

(30) Foreign Application Priority Data
Dec. 6, 2010  (WO) .................. PCT/CN2010/079463

(51) Int. Cl.
| | | |
|---|---|---|
| A01N 43/54 | (2006.01) | |
| A61K 31/505 | (2006.01) | |
| C07D 401/06 | (2006.01) | |
| C07D 403/06 | (2006.01) | |
| C07D 401/14 | (2006.01) | |
| C07D 213/69 | (2006.01) | |
| C07D 239/52 | (2006.01) | |
| C07D 401/12 | (2006.01) | |

(52) U.S. Cl.
CPC ............ *C07D 239/52* (2013.01); *C07D 401/06* (2013.01); *C07D 403/06* (2013.01); *C07D 401/14* (2013.01); *C07D 213/69* (2013.01); *C07D 401/12* (2013.01)

USPC ........... 514/274; 544/299; 544/300; 544/315; 544/316; 546/290; 546/296; 514/345; 514/348

(58) Field of Classification Search
CPC .. C07D 213/64; C07D 213/69; C07D 239/36; C07D 239/52; A61K 31/4412; A61K 31/513
USPC .......... 544/299, 300, 315, 316; 546/296, 290; 514/274, 348, 345
See application file for complete search history.

(56) References Cited

U.S. PATENT DOCUMENTS

| | | | |
|---|---|---|---|
| 6,417,192 B1 | 7/2002 | Hickey | |
| 6,559,155 B1 | 5/2003 | Leach et al. | |
| 2012/0142717 A1* | 6/2012 | Jin et al. ....................... | 514/274 |

FOREIGN PATENT DOCUMENTS

| | | |
|---|---|---|
| WO | WO0010980 | 3/2000 |
| WO | WO0160805 | 8/2001 |
| WO | WO 0160805 A1 * | 8/2001 |
| WO | WO0230904 | 4/2002 |
| WO | WO 0230904 A1 * | 4/2002 |
| WO | WO 0247690 A1 * | 6/2002 |
| WO | WO2007043835 | 4/2007 |

OTHER PUBLICATIONS

B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*
M.A. Fox, Organic Chemistry, 133-134 (1997).*
Oxford Dictionary of Chemistry 169 (John Daintith ed., 6th ed., 2008).*
S. Mirozoeva et al. J. Med. Chem. 45, 563-566 (2002).*
J.H. H Poupaert, Drug Design: Basic Principles and Applications, in 2 Encyclopedia of Pharmaceutical Technology 1362-1369, 1367 (James Swarbrick ed., 3rd ed., 2007).*

* cited by examiner

*Primary Examiner* — James O Wilson
*Assistant Examiner* — Alexander R Pagano
(74) *Attorney, Agent, or Firm* — Fang Qian

(57) ABSTRACT

The present invention relates to novel compounds that inhibit Lp-PLA$_2$ activity, processes for their preparation, to compositions containing them and to their use in the treatment of diseases associated with the activity of Lp-PLA$_2$, for example atherosclerosis, Alzheimer's disease, and/or diabetic macular edema.

13 Claims, No Drawings

PYRIMIDINONE AND PYRIDINONE COMPOUNDS FOR USE IN THE TREATMENT OF DISEASES OR CONDITIONS MEDIATED BY LP-PLA$_2$

This application is a 371 of International Application No. PCT/CN2011/083465, filed 5 Dec. 2011, which claims priority to PCT Application No. PCT/CN2010/079463 filed 6 Dec. 2010.

FIELD OF THE INVENTION

The present invention relates to novel pyrimidinone and pyridinones compounds, processes for their preparation, intermediates useful in their preparation, pharmaceutical compositions containing them, and their use in therapy for the treatment of diseases or conditions mediated by Lp-PLA$_2$.

BACKGROUND OF THE INVENTION

Lipoprotein-associated phospholipase A$_2$ (Lp-PLA$_2$) previously known as platelet-activating factor acetylhydrolase (PAF-AH), is a phospholipase A2 enzyme involved in hydrolysis of lipoprotein lipids or phospholipids, Lp-PLA$_2$ travels with low-density lipoprotein (LDL) and rapidly cleaves oxidized phosphatidylcholine molecules derived from the oxidation of LDL. (See e.g., Zalewski A, et ah, *Arterioscler. Thromb. Vase. Biol*, 25, 5, 923-31(2005)). Lp-PLA$_2$ hydrolyzes the sn-2 ester of the oxidized phosphatidylcholines to give lipid mediators, lysophosphatidylcholine (lysoPC) and oxidized nonesterified fatty acids (NEFAs). It has been observed that lysoPC and NEFAs elicit inflammatory responses. (See e.g., Zalewski A, et al. (2005)).

A number of Lp-PLA$_2$ inhibitors and/or uses thereof have been previously described. (See for example, published patent application nos. WO96/13484, WO96/19451, WO97/02242, WO97/12963, WO97/21675, WO97/21676, WO 97/41098, WO97/41099, WO99/24420, WO00/10980, WO00/66566, WO00/66567, WO00/68208, WO01/60805, WO02/30904, WO02/30911, WO03/015786, WO03/016287, WO03/041712, WO03/042179, WO03/042206, WO03/042218, WO03/086400, WO03/87088, WO08/048, 867, US 2008/0103156, US 2008/0090851, US 2008/0090852, and WO08/048,866.) Disclosed uses include treating disease that involves or is associated with endothelial dysfunction, disease that involves lipid oxidation in conjunction with Lp-PLA$_2$ activity (e.g., associated with the formation of lysophosphatidylcholine and oxidized free fatty acids), and disease that involves activated monocytes, macrophages or lymphocytes or which is associated with increased involvement of monocytes, macrophages or lymphocytes. Examples of particular diseases or conditions include atherosclerosis (e.g. peripheral vascular atherosclerosis and cerebrovascular atherosclerosis), diabetes, hypertension, angina pectoris, after ischaemia and reperfusion, rheumatoid arthritis, stroke, inflammatory conditions of the brain such as Alzheimer's Disease, various neuropsychiatric disorders such as schizophrenia, myocardial infarction, ischaemia, reperfusion injury, sepsis, acute and chronic inflammation, and psoriasis.

Lp-PLA$_2$ inhibitors and/or uses thereof are also reported, for example, in PCT Publication Nos. WO05/003118 (and its Canadian family member CA 2530816A1); WO06/063811; WO06/063813 and WO 2008/141176, JP 200188847 and US Published Patent Application Nos. US 2008/0279846 A1, US 2010/0239565 A1, and US 2008/0280829 A1.

Other researchers have studied the effects related to Lp-PLA$_2$ and inhibitors thereof. For example, research data has also indicated that LysoPC promotes atherosclerotic plaque development, which can ultimately lead to the formation of a necrotic core, (See e.g., Wilensky et al, *Current Opinion in Lipidology,* 20, 415-420 (2009)). In addition, the effect of Lp-PLA$_2$ inhibitors on atherosclerotic plaque composition was demonstrated in a diabetic and hypercholesterolemic porcine model of accelerated coronary atherosclerosis. (See e.g., Wilensky et al., *Nature Medicine,* 10, 1015-1016 (2008)). These research results provided further evidence that Lp-PLA$_2$ inhibitors may be used to treat atherosclerosis.

Additional research have found that high Lp-PLA$_2$ activity is associated with high risk of dementia, including Alzheimer's disease (AD) (See e.g., Van Oijen, et al. Annals of Neurology, 59,139 (2006)). Higher level of oxidized LDL has also been observed in AD patients (See e.g., Kassner et al. *Current Alzheimer Research,* 5, 358-366 (2008); Dildar, et al, *Alzheimer Dis Assoc Disord,* 24, April-June (2010); Sinem, et al. *Current Alzheimer Research,* 7, 463-469 (2010)). Further, research data has shown that neuroinflammation are present in AD patients and multiple cytotoxic inflammatory cytokines are up-regulated in AD patients. (See e.g., Colangelo, et al, *Journal of Neuroscience Research,* 70, 462-473 (2002); Wyss-Coray, *Nature Medicine,* 12, September (2006)). Research has shown that LysoPC function as a pro-inflammatory factor inducing multiple cytotoxic inflammatory cytokine release (See Shi, et al. *Atherosclerosis,* 191, 54-62 (2007)). Therefore, these recent researches have provided additional evidence that that the inhibitors of Lp-PLA$_2$ can be used to treat AD by inhibiting activity of Lp-PLA$_2$ and reducing lysoPC production.

In addition, the treatment of an Lp-PLA$_2$ inhibitor on a diabetic and hypercholesterolemia swine model demonstrated that the blood-brain-barrier leakage and the brain amyloid beta protein (Aβ) burden, the pathological hallmarks of Alzheimer's disease, were reduced. (See U.S. Patent Application Publication No. 2008/0279846). This publication describes several uses of Lp-PLA$_2$ inhibitors for treating diseases associated with blood-brain-barrier leakage, including, e.g., Alzheimer's disease and vascular dementia.

Further, neuroinflammation, including multiple cytotoxic cytokine release, is a common feature of all neurodegenerative diseases including multiple sclerosis, amyotrophic lateral sclerosis, Parkinson's disease, Alzheimer's disease, etc. (See e.g., Perry, *Acta Neuropathol,* 120, 277-286 (2010)). As discussed above, Lp-PLA$_2$ inhibitors can reduce inflammation, for example, reducing multiple cytokine release by suppressing lysoPC production. (See e.g., Shi, et al. *Atherosclerosis* 191, 54-62 (2007)). Thus, inhibiting Lp-PLA$_2$ is a potential therapeutic treatment for neurodegenerative diseases including multiple sclerosis, amyotrophic lateral sclerosis, Parkinson's disease, etc.

In addition to the inflammatory effect, LysoPC has been implicated in leukocyte activation, induction of apoptosis and mediation of endothelial dysfunction (See, e.g., Wilensky et al, *Current Opinion in Lipidology,* 20, 415-420 (2009)). Therefore, it is believed that Lp-PLA$_2$ inhibitors can be used to treat tissue damage associated with diabetes by reducing the production of lysoPC, which can cause a continuous cycle of vascular inflammation and increased reactive oxygen species (ROS) production. In light of the inflammatory roles of Lp-PLA$_2$ and the association between localized inflammatory processes and diabetic retinopathy, it is postulated that Lp-PLA$_2$ can be used to treat diabetic eye disease.

Glaucoma and age-related macular degeneration (AMD) are retina neurodegenerative diseases. Studies suggested that inflammation, including TNF-alpha signaling, may play an important role in the pathogenesis of glaucoma and AMD (See e.g., Buschini et al., *Progress in Neurobiology*, 95, 14-25 (2011); Tezel, *Progress in Brain Research*, vol. 173, ISSN0079-6123, Chapter 28). Thus, considering Lp-PLA$_2$ inhibitors' function of blocking inflammatory cytokine release (See e.g., Shi, et al. *Atherosclerosis*, 191, 54-62 (2007)), it is believed that Lp-PLA$_2$ inhibitors can provide a potential therapeutic application for both glaucoma and AMD.

In view of the number of pathological responses that are mediated by Lp-PLA$_2$) attempts have been made to prepare compounds that inhibit its activity. Though a number of such compounds have been disclosed in the art, there remains a continuing need for inhibitors of Lp-PLA$_2$ which can be used in the treatment of a variety of conditions.

SUMMARY OF THE INVENTION

In a first aspect, this invention relates to a compound of Formula (I) or pharmaceutically acceptable salts thereof

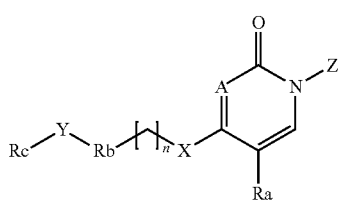

(I)

or a salt thereof wherein:
A is N or CH;
n is 1 or 2;
X is O, CH$_2$ or NH;
when A is N, Y is absent, O or CH$_2$ or when A is CH, Y is O;
Z is H, C$_1$-C$_3$alkyl, —(C$_1$-C$_3$alkyl)-heteroaryl wherein said heteroaryl is optionally substituted with one or more substituents independently selected from the group consisting of C$_1$-C$_3$alkyl and C$_1$-C$_3$alkoxyl;
Ra is H, F, Cl, or C$_1$-C$_3$alkyl;
Rb is phenyl or heteroaryl, either of which is optionally substituted with one or more substituents independently selected from the group consisting of CN and halo; and
Rc is phenyl or heteroaryl, wherein either of phenyl or heteroaryl is optionally substituted with one or more substituents independently selected from the group consisting of halo, C$_1$-C$_3$alkyl, and C$_1$-C$_3$haloalkyl.

This invention also provides pharmaceutical compositions comprising a compound of present invention and pharmaceutically acceptable carriers.

The invention also provides methods of treating a disease associated with the activity of Lp-PLA$_2$, which comprises treating a subject in need thereof with a therapeutically effective amount of an inhibitor of Lp-PLA$_2$. The disease may be associated with the increased involvement of monocytes, macrophages or lymphocytes; with the formation of lyso-phosphatidylcholine and oxidized free fatty acids; with lipid oxidation in conjunction with Lp-PLA$_2$ activity; or with endothelial dysfunction.

This invention also provides methods of treating a disease by inhibiting Lp-PLA$_2$ activity. Exemplary disease includes, but is not limited to, neurodegeneration disease (e.g., Alzheimer's disease, vascular dementia), atherosclerosis, stroke, metabolic bone disorder (e.g., bone marrow abnormalities), dyslipidemia, Paget's diseases, type II diseases, metabolic syndrome, insulin resistance, and hyperparathyroidism, diabetic ocular disorder (e.g., macular edema, diabetic retinopathy, and posterior uveitis), macular edema, wound healing, rheumatoid arthritis, chronic obstructive pulmonary disease (COPD) and multiple sclerosis. The methods comprise administering a safe and effective amount of a compound of this invention to a subject in need thereof. It is not intended that the present invention to be limited to any particular stage of the disease (e.g. early or advanced).

This invention also provides methods of treating Alzheimer's disease. The methods comprise administering to a subject in need thereof a safe and effective amount of a compound of this invention.

This invention also provides methods of decreasing beta amyloid (also referred to as "Aβ") accumulation in the brain of a subject. The methods comprise administering to a subject in need thereof a safe and effective amount of a compound of the present invention. In certain embodiment, the beta amyloid is Abeta-42.

This invention also provides methods for treating eye diseases and disorders by administering a compound of this invention. In certain embodiment, this invention provides methods of treating macular edema, which comprises administering to the subject a safe and effective amount of a compound of this invention. In certain embodiment, the macular edema is associated with diabetic eye disease, for example, diabetic retinopathy. In one embodiment, the macular edema is associated with posterior uveitis.

This invention also provides the use of a compound of this invention for manufacturing a medicament for treating diseases described herein.

This invention also provides a compound described herein for use in carrying out methods of treatment described herein.

DETAILED DESCRIPTION OF THE INVENTION

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Generally, the nomenclature used herein and the laboratory procedures in organic chemistry, medicinal chemistry, biology and virology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

All patents, patent applications and publications referred to herein are incorporated by reference in their entirety. In case of a conflict in terminology, the present specification is controlling.

A. DEFINITIONS

The term "disease" refers to any alteration in state of the body or of some of the organs, interrupting or disturbing the performance of the functions and/or causing symptoms such as discomfort, dysfunction, distress, or even death to the person afflicted or those in contact with a person. A disease can also include a distemper, ailing, ailment, malady, disorder, sickness, illness, complain, interdisposition and/or affectation.

The term "neurodegeneration disease" or "neurodegenerative disease" as used herein refers to a varied assortment of central nervous system disorders characterized by gradual and progressive loss of neural tissue and/or neural tissue function. A neurodegeneration disease is a class of neurological disorder or disease where the neurological disease is characterized by a gradual and progressive loss of neural tissue, and/or altered neurological function, typically reduced neurological function as a result of a gradual and progressive loss of neural tissue. In one embodiment, the neurodegeneration diseases described herein are neurodegeneration diseases or disorders where there is an abnormal blood brain barrier, for example a permeable blood brain barrier. Examples of neurodegeneration diseases where there is a defective blood brain barrier include, but are not limited to, Alzheimer's disease, Huntington's disease, Parkinson's disease, vascular dementia and the like.

The term "vascular dementia" is also referred to as "multi-infarct dementia", which refers to a group of syndromes caused by different mechanisms, which all result in vascular lesions in the brain. The main subtypes of vascular dementia are, for example, vascular mild cognitive impairment, multi-infarct dementia, vascular dementia due to a strategic single infarct, (affecting the thalamus, the anterior cerebral artery, the parietal lobes or the cingulated gyrus), vascular dementia due to hemorrhagic lesions, small vessel disease (including, e.g. vascular dementia due to lacunar lesions and Binswanger disease), and mixed Alzheimer's Disease with vascular dementia.

The phrase "blood-brain barrier" or "BBB" are used interchangeably herein, and are used to refer to the permeability barrier that exists in blood vessels as they travel through the brain tissue that severely restricts and closely regulates what is exchanged between the blood and the brain tissue. The blood brain barrier components include the endothelial cells that form the innermost lining of all blood vessels, the tight junctions between adjacent endothelial cells that are structural correlate of the BBB, the basement membrane of endothelial cells and the expanded foot process of nearby astrocytes which cover nearly all of the exposed outer surface of the blood vessel.

The phrase "metabolic bone disease" as used herein refers to a varied assortment of bone diseases and disorders characterized by gradual and progressive loss of bone tissue. Metabolic bone diseases described herein are metabolic bone diseases whereby there is a condition of diffusely decreased bone density and/or diminished bone strength. Such diseases are characterized by histological appearance. Exemplary metabolic bone diseases include, but are not limited to, osteoporosis which is characterized by decreased mineral and bone matrix, and osteomalacia which is characterized by decreased mineral but intact bone matrix.

The term "osteopenic diseases" or "osteopenia" are used interchangeably herein, and refer to conditions with decreased calcification and/or bone density, and is a descriptive term used to refer to all skeletal systems in which decreased calcification and/or bone density is observed. Osteopenia also refers to a reduced bone mass due to inadequate osteiod synthesis.

The term "osteoporosis" refers to conditions which mineral and/or bone matrix are decreased and/or bone mass is reduced.

"Alkyl" refers to a straight- or branched-chain hydrocarbon radical having the specified number of carbon atoms. In one embodiment, alkyl is monovalent and saturated hydrocarbon chain. In certain embodiment, $C_1$-$C_6$ alkyl refers to an alkyl group having from 1 to 6 carbon atoms. In certain embodiment, $C_1$-$C_3$ alkyl refers to an alkyl group having from 1 to 3 carbon atoms. In still other embodiments, alkyl groups contain 1 to 2, 3, 4, or 5 carbon atoms. Alkyl groups may be optionally substituted with one or more substituent as defined herein. Alkyl groups may be straight or branched. In one embodiment, branched alkyl groups may have one, two, or three branches. Exemplary alkyl includes, but is not limited to, methyl, methylethyl, ethyl, propyl (n-propyl and isopropyl), methylpropyl, butyl (n-butyl, isobutyl, and t-butyl), pentyl (n-pentyl, isopentyl, and neopentyl), and hexyl.

"Alkoxy" refers to the group —O-alkyl. In one embodiment, alkoxyl groups contain 1 to 2, 3, 4, 5 or 6 carbon atoms. Exemplary alkoxy groups include, but are not limited to, methoxy, ethoxy and propoxy.

"Halogen" refers to fluorine (F), chlorine (Cl), bromine (Br), or iodine (I). "Halo" refers to the halogen radicals: fluoro (—F), chloro (—Cl), bromo (—Br), and iodo (–1).

"Haloalkyl" refers to an alkyl group, as defined above, having one or more halogen atoms selected from F, Cl, Br, or I, which are substituted on any or all of the carbon atoms of the alkyl group by replacing hydrogen atoms attached to the carbon atoms. Exemplary haloalkyl groups include, but are not limited to, chloromethyl, bromoethyl, trifluoromethyl, dichloromethyl, $CH_2CF_3$.

"Heteroaryl" refers to an aromatic monocyclic ring has the specified number of ring atoms, and that ring contains at least one heteratom selected from N, O, and/or S. Examples of "heteroaryl" groups include pyrazolyls, pyridinyl, pyrimidinyl, furanyl, thiophenyl, pyrrolyl, imidazolyl, trizolyl, tetrazolyl, oxazolyl, isoxazolyl, oxadiazolyl, oxo-pyridyl, thiadiazolyl, thiazolyl, isothizolyl, pyridazinyl, pyrazinyl, triazinyl.

"Optionally" means that the subsequently described event(s) may or may not occur, and includes both event(s), which occur, and events that do not occur.

"Substituted" in reference to a group indicates that one or more hydrogen atom attached to a member atom (e.g., carbon atom) within the group is replaced with a substituent selected from the group of defined substituents. It should be understood that the term "substituted" includes the implicit provision that such substitution is in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom. Exemplary substituents include, but are not limited to, halo, hydroxyl, amino, substituted amine, amide, —SH, cyano, nitro, thioalkyl, carboxylic acid, —NH—C(=NH)—NH$_2$, alkyl, alkenyl, alkynyl, alkoxyl, aryl, heteroaryl, cycloalkyl, heterocycloalkyl, in which alkyl, alkenyl, alkynyl, alkoxyl, aryl, heteroaryl, cycloalkyl, thioalkyl and heterocycloalkyl may be further substituted. Suitable substituents are defined herein for each substituted or optionally substituted group.

"Treat", "treating" or "treatment" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, and/or (4) to slow the progression of the condition or one or more of the biological manifestations of the condition.

"Solvate" refers to a complex of variable stoichiometry formed by a solute and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

"Pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

An "effective amount" means that the amount of a compound of Formula (I) or a salt thereof that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

B. COMPOUNDS

This invention provides, in a first aspect, compounds of Formula (I) and pharmaceutically acceptable salts thereof:

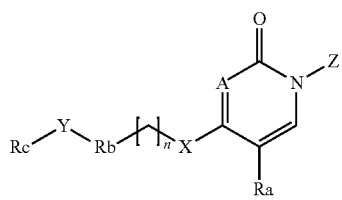

(I)

wherein:
A is N or CH;
n is 1 or 2;
X is O, CH$_2$ or NH;
when A is N, Y is absent, O or CH$_2$ or when A is CH, Y is O;
Z is H, C$_1$-C$_3$ alkyl, —(C$_1$-C$_3$alkyl)-heteroaryl wherein said heteroaryl is optionally substituted with one or more substituents independently selected from the group consisting of C$_1$-C$_3$alkyl and C$_1$-C$_3$alkoxyl;
Ra is H, F, Cl, or C$_1$-C$_3$alkyl;
Rb is phenyl or heteroaryl, wherein either of which is optionally substituted with one or more substituents independently selected from the group consisting of CN and halo; and
Rc is phenyl or heteroaryl, wherein either of phenyl or heteroaryl is optionally substituted with one or more substituents independently selected from the group consisting of halo, C$_1$-C$_3$alkyl, and C$_1$-C$_3$haloalkyl.

In one embodiment, this invention provides compounds of Formula (I), wherein
A is N;
n is 1 or 2;
X is O;
Y is O;
Z is H, C$_2$H$_5$, —CH$_2$-heteroaryl, wherein said heteroaryl is selected from the group consisting of pyridinyl, pyrazolyl, pyrimidinyl, and the heteroaryl is optionally substituted with one or more substituents independently selected from the group consisting of CH$_3$ and —OCH$_3$;
Ra is H, F, Cl, or C$_1$-C$_3$alkyl;
Rb is phenyl or heteroaryl, wherein either of which is optionally substituted with one or more substituents independently selected from the group consisting of CN and halo; and
Rc is phenyl or heteroaryl, wherein either of phenyl or heteroaryl is optionally substituted with one or more substituents independently selected from the group consisting of halo, C$_1$-C$_3$alkyl, and C$_1$-C$_3$haloalkyl.

In one embodiment, this invention provides compounds of Formula (I), wherein
A is N;
n is 1 or 2;
X is O;
Y is O;
Z is —CH$_2$-heteroaryl, wherein said heteroaryl is selected from the group consisting of pyridinyl, pyrazolyl, pyrimidinyl, and the heteroaryl is optionally substituted with one or more substituents independently selected from the group consisting of CH$_3$ and —OCH$_3$;
Ra is H, F, Cl or C$_1$-C$_3$alkyl;
Rb is phenyl optionally substituted with one or more substituents independently selected from the group consisting of CN and F; and
Rc is phenyl optionally substituted with one or more substituents independently selected from the group consisting of F, Cl, CH$_3$ and CF$_3$.

In one embodiment, this invention also relates to compounds of any of the above embodiments, wherein A is N.

In one embodiment, this invention also relates to compounds of any of the above embodiments, wherein n is 1 or 2. In one embodiment, this invention also relates to compounds of any of the above embodiments, wherein n is 1. In one embodiment, this invention also relates to compounds of any of the above embodiments, wherein n is 2.

In one embodiment, this invention also relates to compounds of any of the above embodiments, wherein X is O. In one embodiment, this invention also relates to compounds of any of the above embodiments, wherein X is CH$_2$. In one embodiment, this invention also relates to compounds of any of the above embodiments, wherein X is NH.

In one embodiment, this invention also relates to compounds of any of the above embodiments, wherein Y is O. In one embodiment, this invention also relates to compounds of any of the above embodiments, wherein Y is absent. In one embodiment, this invention also relates to compounds of any of the above embodiments, wherein Y is $CH_2$.

In one embodiment, this invention also relates to compounds of any of the above embodiments, wherein Z is H. In one embodiment, this invention also relates to compounds of any of the above embodiments, wherein Z is $C_1$-$C_6$-alkyl, for example ethyl. In one embodiment, this invention also relates to compounds of any of the above embodiments, wherein Z is —($C_1$-$C_3$alkyl)-heteroaryl wherein said heteroaryl is optionally substituted with one or more substituents independently selected from the group consisting of $C_1$-$C_3$ alkyl and $C_1$-$C_3$ alkoxyl. In one embodiment, this invention also relates to compounds of any of the above embodiments, wherein Z is —$CH_2$-heteroaryl, wherein said heteroaryl is selected from the group consisting of pyridinyl, pyrazolyl, pyrimidinyl, and the heteroaryl is optionally substituted with one or more substituents independently selected from the group consisting of $CH_3$ and —$OCH_3$. In one embodiment, this invention also relates to compounds of any of the above embodiments, wherein Z is —$CH_2$-pyridinyl, wherein the pyridinyl is unsubstituted. In one embodiment, this invention also relates to compounds of any of the above embodiments, wherein Z is —$CH_2$-pyrazolyl or —$CH_2$-pyrimidinyl, wherein pyrazolyl or pyrimidinyl is optionally substituted with one or more substituents independently selected from the group consisting of $CH_3$ and —$OCH_3$ In one embodiment, this invention also relates to compounds of any of the above embodiments, wherein Ra is H. In one embodiment, this invention also relates to compounds of any of the above embodiments, wherein Ra is F or Cl. In one embodiment, this invention also relates to compounds of any of the above embodiments, wherein Ra is $C_1$-$C_3$ alkyl.

In one embodiment, this invention also relates to compounds of any of the above embodiments, wherein Rb is phenyl optionally substituted with one or more substituents independently selected from the group consisting of CN and F. In one embodiment, this invention also relates to compounds of any of the above embodiments, wherein Rb is pyridinyl optionally substituted with one or more substituents independently selected from the group consisting of CN and F.

In one embodiment, this invention also relates to compounds of any of the above embodiments, wherein Rc is phenyl optionally substituted with one or more substituents independently selected from the group consisting of halo, $C_1$-$C_6$alkyl and $C_1$-$C_6$haloalkyl. In one embodiment, this invention also relates to compounds of any of the above embodiments, wherein Rc is phenyl optionally substituted with one or more substituents independently selected from the group consisting of F, Cl, $CH_3$ and $CF_3$. In one embodiment, this invention also relates to compounds of any of the above embodiments, wherein Rc is phenyl substituted with $CF_3$ at the 3 position and Cl at the 4 position. In one embodiment, this invention also relates to compounds of any of the above embodiments, wherein Rc is pyridinyl optionally substituted with one or more substituents independently selected from the group consisting of $CH_3$ and $CF_3$.

The compounds of Formula (I), or pharmaceutically acceptable salts thereof, or pharmaceutically acceptable solvates thereof may exist in stereoisomeric forms (e.g., it contains one or more asymmetric carbon atoms). The individual stereoisomers (enantiomers and diastereomers) and mixtures of these are included within the scope of the present invention. The invention also covers the individual isomers of the compounds of Formula (I) or pharmaceutically acceptable salts, or pharmaceutically acceptable solvates thereof as mixtures with isomers thereof in which one or more chiral centers are inverted. Likewise, it is understood that the compounds of Formula (I) or pharmaceutically acceptable salts thereof, or pharmaceutically acceptable solvates thereof may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. Also included within the scope of the invention are individual isomers of the compounds of Formula (I) or pharmaceutically acceptable salts thereof, or pharmaceutically acceptable solvates thereof as well as any wholly or partially equilibrated mixtures thereof. The present invention also includes the individual isomers of the compounds of Formula (I) or pharmaceutically acceptable salts thereof, or pharmaceutically acceptable solvates thereof as well as mixtures with isomers thereof in which one or more chiral centers are inverted. It is to be understood that the present invention includes all combinations and subsets of the particular groups defined hereinabove.

Certain compounds described herein may contain one or more chiral atoms, or may otherwise be capable of existing as enantiomers. The compounds of the present invention include mixtures of enantiomers as well as purified enantiomers or enantiomerically enriched mixtures. Also included within the scope of the invention are the individual isomers of the compounds of the present invention as well as any wholly or partially equilibrated mixtures thereof. The present invention also covers the individual isomers of the claimed compounds as mixtures with isomers thereof in which one or more chiral centers are inverted. Also, it is understood that any tautomers and mixtures of tautomers of the compounds described herein are included within the scope of the compounds of the present invention. The different isomeric forms may be separated or resolved one from the other by conventional methods, or any given isomer may be obtained by conventional synthetic methods or by stereospecific or asymmetric syntheses.

The invention also includes various deuterated forms of compounds of Formula (I) or pharmaceutically acceptable salts thereof, or pharmaceutically acceptable solvates thereof. Each available hydrogen atom attached to a carbon atom may be independently replaced with a deuterium atom. A person of ordinary skill in the art will know how to synthesize deuterated forms of compounds of Formula (I) or pharmaceutically acceptable salts thereof, or pharmaceutically acceptable solvates thereof. Commercially available deuterated starting materials may be employed in the preparation of deuterated forms of compounds of Formula (I) or pharmaceutically acceptable salts thereof, or pharmaceutically acceptable solvates thereof or they may be synthesized using conventional techniques employing deuterated reagents (e.g. lithium aluminum deuteride).

In addition to the free base form of the compounds described herein, the salt form of the compounds is also within the scope of the present invention. The pharmaceutically-acceptable salts may be prepared in situ during the final isolation and purification of the compound, or by separately reacting the purified compound in its free acid or free base form with a suitable base, or acid, respectively.

In one embodiment, compounds of the present invention may contain an acidic functional group, which is acidic enough to form salts. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, diethylamine, triethylamine, ethylenediamine, ethanolamine, diethanolamine, and cyclohexylamine.

In certain embodiments, compounds of the present invention may contain a basic group and are therefore capable of forming pharmaceutically-acceptable acid addition salts by treatment with a suitable acid. Suitable acids include pharmaceutically-acceptable inorganic acids and pharmaceutically-acceptable organic acids. These salts may be crystalline or amophorus. Exemplary pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicylate, glycollate, lactate, heptanoate; phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In some embodiments, the pharmaceutically acceptable salts include the L-tartrate, ethanedisulfonate (edisylate), sulfate, phosphate, p-toluenesulfonate (tosylate), hydrochloride salt, methanesulfonate, citrate, fumarate, benzenesulfonate, maleate, hydrobromate, L-lactate, malonate, and S-camphor-10-sulfonate. Some of these salts form solvates, some are crystalline.

As used herein, the term "compounds of the invention" means both the compounds according to Formula I, the pharmaceutically-acceptable salts thereof, and the pharmaceutically-acceptable solvates thereof. The term "a compound of the invention" also appears herein and refers to both a compound according to Formula I, the pharmaceutically-acceptable salts thereof, and the pharmaceutically-acceptable solvates thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing viable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. The invention includes all such polymorphs.

C. SYNTHESIS OF COMPOUNDS

The process to be utilized in the preparation of the compounds described herein depends upon the desired compounds. Such factors as the selection of the specific substituent and various possible locations of the specific substituent all play a role in the path to be followed in the preparation of the specific compounds of this invention. Those factors are readily recognized by one of ordinary skill in the art.

In general, the compounds of the present invention may be prepared by standard techniques known in the art and by known processes analogous thereto. General methods for preparing compounds of the present invention are set forth below.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

General experiment schemes 1-3 provide an exemplary process of synthesis for preparing some compounds of the present invention.

General Experimental Scheme 1

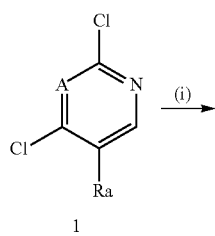

-continued

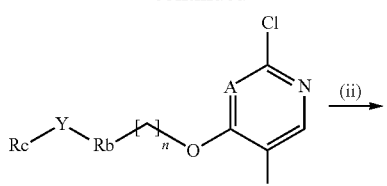
2

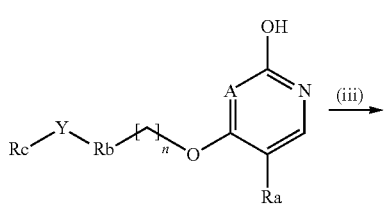
3

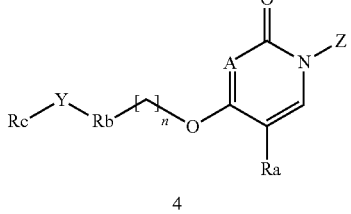
4

Ra is H, Cl or C$_{1-3}$alkyl
A, Z, Y, n, Rb and Rc are as defined in Formula (I)

General Experimental Scheme 1 provides an exemplary synthesis for compound 4. Step (i) may be carried out by reacting compound 1 with alcohol Rc-Y-Rb-(CH$_2$)$_n$—OH or amine Rc-Y-Rb-(CH$_2$)$_n$—NH$_2$ in the presence of suitable base such as NaH in a suitable solvent such as dimethylformamide (DMF) at suitable temperature such as 0° C. to provide compound 2. Step (ii) may be carried out by reacting compound 2 with suitable base such as K$_2$CO$_3$ and 1,4-diazabicyclo[2.2.2]octane (DABCO) in a suitable mixed solvent such as dioxane/H$_2$O at suitable temperature such as 60° C. to provide compound 3, Step (iii) may be taken place by reacting compound 3 with a suitable reagent such as Z—X, wherein X represents a suitable leaving group such as halo, using a suitable base such as Cs$_2$CO$_3$ in a suitable solvent such as DMF at suitable temperature such as 60° C. to afford compound 4.

General Experimental Scheme 2

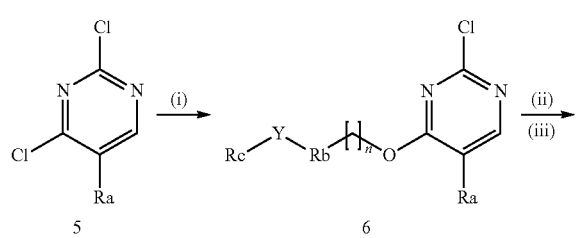
5      6

-continued

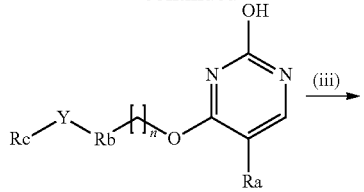
7

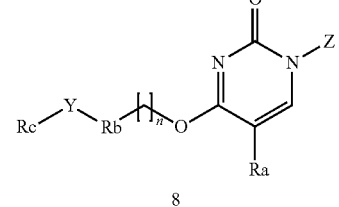
8

Ra is F
A, Z, Y, n, Rb and Rc are as defined in Formula (I)

General Experimental Scheme 2 provides an exemplary synthesis for compound 8. Step (i) may be carried out by reacting compound 5 with alcohol Rc-Y-Rb-(CH$_2$)$_n$—OH in the presence of suitable base such as NaH in a suitable solvent such as dimethylformamide (DMF) at suitable temperature such as 0° C. to provide compound 6. Step (ii) may be carried out by reacting compound 6 with suitable base such as NaH in a suitable solvent such as DMF at suitable temperature such as 0° C., then hydrogenation takes place in Step (iii) by using a suitable reagent such as Pd/C in a suitable solvent such as MeOH under H$_2$ atmosphere at suitable temperature such as rt to afford compound 7. Step (iv) may be carried out by reacting compound 7 with a suitable reagent such as Z—X, wherein X represents a suitable leaving group such as halo, using a suitable base such as Cs$_2$CO$_3$ in a suitable solvent such as DMF at suitable temperature such as 60° C. to afford compound 8.

General Experimental Scheme 3

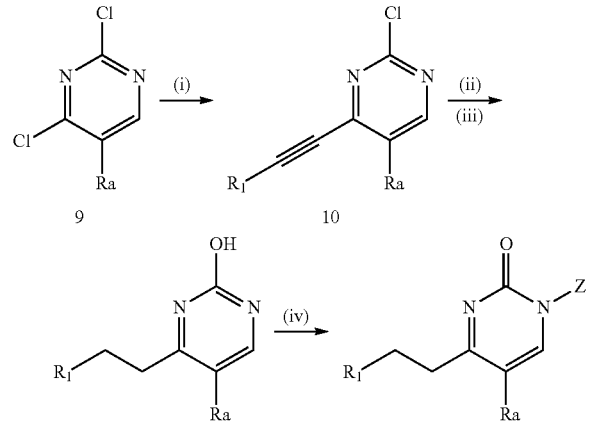

R$_1$ is Rc—Y—Rb—(CH$_2$)$_{n-1}$-
A, Ra, Rb, Rc, Y, Z and n are as defined in Formula (I)

General Experimental Scheme 3 provides an exemplary synthesis for compound 12. Step (i) may be carried out by reacting compound 1 with alkynes R$_1$—C≡CH in the presence of a suitable catalyst such as copper(I) iodide and dichloropalladium-triphenylphosphane in a mixed solvent such as triethyl amine and tetrahydrofuran (THF) at suitable temperature such as 60° C. to provide compound 10. Step (ii) may be carried out by reacting compound 10 with hydrogen gas with suitable catalyst such as Pd/C in a suitable solvent such as methanol at suitable temperature such as room temperature, then hydrolysis takes place in Step (iii) by using a suitable base such as $K_2CO_3$ and DABCO in a suitable mixed solvents such as dioxane/$H_2O$ at suitable temperature such as 60° C. Step (iv) may be taken place by reacting compound 11 with a suitable reagent such as Z—X, wherein X' represents a suitable leaving group such as halo, using a suitable base such as $Cs_2CO_3$ in a suitable solvent such as DMF at suitable temperature such as 60° C. to afford compound 12.

General Experimental Procedures

Heating of reaction mixtures with microwave irradiations was carried out on a Smith Creator (purchased from Personal Chemistry, Forboro/MA, now owned by Biotage), an Emrys Optimizer (purchased from Personal Chemistry) or an Explorer (provided by CEM Discover, Matthews/NC) microwave.

Conventional techniques may be used herein for work up of reactions and purification of the products of the Examples.

References in the Examples below relating to the drying of organic layers or phases may refer to drying the solution over magnesium sulfate or sodium sulfate and filtering off the drying agent in accordance with conventional techniques. Products may generally be obtained by removing the solvent by evaporation under reduced pressure.

Purification of the compounds in the examples may be carried out by conventional methods such as chromatography and/or recrystallization using suitable solvents. Chromatographic methods are known to the skilled person and include e.g. column chromatography, flash chromatography, HPLC (high performance liquid chromatography), and MDAP (mass directed autopreparation, also referred to as mass directed LCMS purification). MDAP is described in e.g. W. Goetzinger et al. *Int. J, Mass Spectrom.,* 2004, 238, 153-162.

Analtech Silica Gel GF and E, Merck Silica Gel 60 F-254 thin layer plates were used for thin layer chromatography. Both flash and gravity chromatography were carried out on E. Merck Kieselgel 60 (230-400 mesh) silica gel. Preparative HPLC were performed using a Gilson Preparative System using a Luna 5u C18(2) 100 A reverse phase column eluting with a 10-80 gradient (0.1% TFA in acetonitrile/0.1% aqueous TFA) or a 10-80 gradient (acetonitrile/water). The CombiFlash system used for purification in this application was purchased from Isco, Inc. CombiFlash purification was carried out using a prepacked $SiO_2$ column, a detector with UV wavelength at 254 nm and mixed solvents.

The terms "CombiFlash", "Biotage®", "Biotage 75" and "Biotage SP4®" when used herein refer to commercially available automated purification systems using pre-packed silica gel cartridges.

Final compounds were characterized with LCMS (conditions listed below) or NMR. $^1$H-NMR spectra were recorded using a Bruker Avance 400 MHz spectrometer. $CDCl_3$ is deuteriochloroform, DMSO-$d_6$ is hexadeuteriodimethylsulfoxide, and $CD_3OD$ (or MeOD) is tetradeuteriomethanol. Chemical shifts are reported in parts per million ($\delta$) downfield from the internal standard tetramethylsilane (TMS) or the NMR solvent. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Mass spectra were taken on instruments, using electrospray (ES) ionization techniques. All temperatures are reported in degrees Celsius. All other abbreviations are as described in the ACS Style Guide (American Chemical Society, Washington, D.C., 1986).

LCMS Conditions:
1) Acidic Conditions;
Mobile phase: water containing 0.05% TFA/0.05% acetonitrile
Column: Agilent SB-C18 4.6×30 mm-1.8 microns
Detection: MS and photodiode array detector (PDA)
2) Basic Conditions:
Mobile phase: water containing 10 mmol $NH_4HCO_3$/acetonitrile
Column: XBridge™ C18 4.6×50 mm-3.5 microns
Detection: MS and photodiode array detector (PDA)
MDAP Conditions:
1) Acidic conditions:
Instrument: Waters instrument
Column: Sunfire Prep C18 column (5 um, 19×50 mm)
Mobile phase: water containing 0.05% TFA/acetonitrile.
2) Basic Conditions:
Instrumnet. Waters instrument
Column: Xbridge Prep C18 column (5 um, 19×50 mm)
Mobile phase: water containing 0.04% ammonia/acetonitrile.

Abbreviations and Resource Sources

The following abbreviations and resources are used herein below:
ISCO system—Teledyne ISCO (http://www.isco.com/html/seFlashChromatography.html)
r.t/rt/RT—Room Temperature;
ACN—Acetonitrile;
AcCl—Acetic chloride
Aq.—aqueous
CV—Column volumesDABCO-1,4-diazabicyclo[2.2.2]octane
DABCO—1,4-diazabicyclo[2.2.2]octane
DCM—Dichloromethane;
DMF—Dimethylformamide;
EA—Ethyl acetate;
NBS—N-bromosuccinamide;
TEA—Triethylamine;
TFA—Trifluoro acetic acid
THF—Tetrahydrofuran;
PE—Petroleum ether;
DIBAL-H—Diisobutylaluminum hydride;
9-BBN—9-Borabicyclo[3,3,1]nonane;
Nomenclature
ChemBioDraw Ultra, or MDL ISIS/Draw 2.5 SP1

EXAMPLES

The following synthetic processes and examples are provided to more specifically illustrate the invention. These examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made without departing from the spirit and scope of the invention.

Intermediates

D1

2-{[4-chloro-3-(trifluoromethyl)phenyl]oxy}-5-formylbenzonitrile

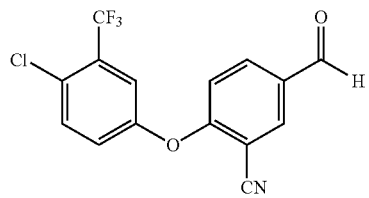

A mixture of 2-fluoro-5-formylbenzonitrile (5.0 g, 33.5 mmol), 4-chloro-3-(trifluoromethyl)phenol (6.59 g, 33.5 mmol) and potassium carbonate (13.9 g, 101 mmol) in N,N-dimethyl formamide (DMF) (10 mL) was stirred at 60° C. overnight and filtered. Purification via Biotage-$C_{18}$ system afforded the title product (6 g) as a pale solid. LC-MS (ESI): m/z 326 [M+H]$^+$; 3.51 min (ret time).

D2

2-{[4-chloro-3-(trifluoromethyl)phenyl]oxy}-5-(hydroxymethyl)benzonitrile

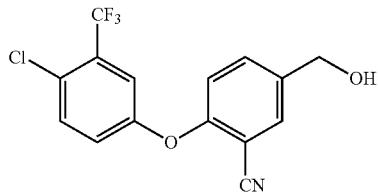 [SMILES: N#Cc1cc(CO)ccc1Oc1ccc(Cl)c(C(F)(F)F)c1]

To a solution of 2-{[4-chloro-3-(trifluoromethyl)phenyl]oxy}-5-formylbenzonitrile (5.0 g, 15.4 mmol) in methanol (50 mL) was added sodium borohydride (0.61 g, 16.1 mmol) at 0° C. The reaction mixture was stirred at rt for 30 min and concentrated. Purification via ISCO system ($CH_2Cl_2$/MeOH-20/1) afforded the title product (4.76 g) as an off-white solid. LC-MS (ESI): m/z 328 [M+H]$^+$; 3.96 min (ret time).

D3

5-{[(2-chloro-4-pyrimidinyl)oxy]methyl}-2-{[4-chloro-3-(trifluoromethyl)phenyl]oxy}benzonitrile

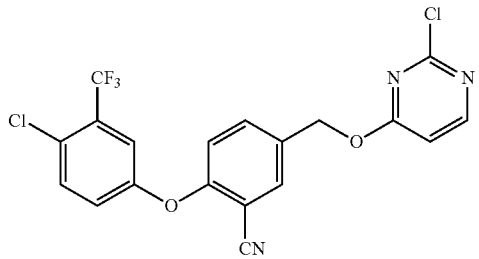 [SMILES: N#Cc1cc(COc2ccnc(Cl)n2)ccc1Oc1ccc(Cl)c(C(F)(F)F)c1]

To a solution of 2-{[4-chloro-3-(trifluoromethyl)phenyl]oxy}-5-(hydroxymethyl)benzonitrile (2.50 g, 7.63 mmol) in N,N-dimethylformamide (20 mL) was added sodium hydride (1.22 g, 30.5 mmol) at 0° C., then 2,4-dichloropyrimidine (1.25 g, 8.39 mmol) was added at 0° C. after 10 min. The reaction mixture was stirred for 30 min, and poured into ice-water (100 mL), extracted with ethyl acetate (50 mL) twice. Combined organic parts were washed with water and brine, dried over sodium sulfate, filtered and concentrated. Purification via ISCO system afforded the title product (2.31 g). LC-MS (ESI): m/z 440 [M+H]$^+$; 3.95 min (ret time).

D4

2-{[4-chloro-3-(trifluoromethyl)phenyl]oxy}-5-{[(2-oxo-2,3-dihydro-4-pyrimidinyl)oxy]methyl}benzonitrile

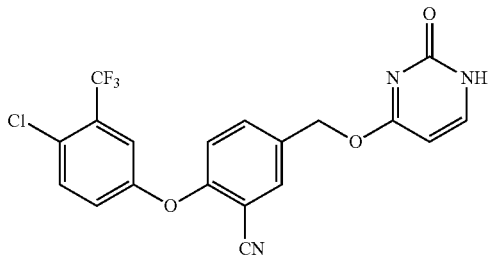 [SMILES: N#Cc1cc(COc2cc[nH]c(=O)n2)ccc1Oc1ccc(Cl)c(C(F)(F)F)c1]

A mixture of 5-{[(2-chloro-4-pyrimidinyl)oxy]methyl}-2-{[4-chloro-3-(trifluoromethyl)phenyl]oxy}benzo-nitrile (2.30 g, 2.61 mmol), DABCO (0.147 g, 1.31 mmol) and potassium carbonate (1.08 g, 7.84 mmol) in a mixed solvents of 1,4-Dioxane (10 mL) and water (10 mL) was heated at 70° C. for 3 h, then concentrated and diluted with ethyl acetate (100 mL) and water (100 mL). Separated organic part was washed with water and brine, dried over sodium sulfate, concentrated. Purification via mass-directed autopreparation afforded the title product (1.0 g). LC-MS (ESI): m/z 420 [M−H]$^+$; 3.89 min (ret time).

D5

2-[(4-{[4-chloro-3-(trifluoromethyl)phenyl]oxy}phenyl)oxy]-5-ethenylbenzonitrile

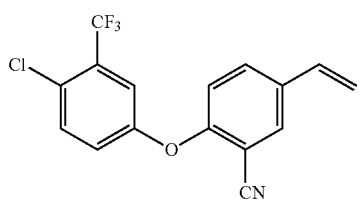 [SMILES: C=Cc1ccc(Oc2ccc(Cl)c(C(F)(F)F)c2)c(C#N)c1]

To the suspension of methyl(triphenyl)phosphonium bromide (1.504 g, 4.62 mmol) in anhydrous tetrahydrofuran (THF) (30 mL), was added BuLi (2.76 mL, 4.41 mmol) dropwise at 0° C. The reaction mixture was turned to clear and stirred for 15 min at 0° C., then a solution of 2-{[4-chloro-3-(trifluoromethyl)phenyl]oxy}-5-formylbenzonitrile (1.5 g, 4.20 mmol) in THF (5 mL) was added. The reaction mixture was warmed to rt and stirred for 1 h, then quenched by sat. $NH_4Cl$, concentrated. The residue was dissolved in ethyl acetate (100 mL), washed with water, and brine, dried over sodium sulfate, concentrated. Purification via ISCO system afforded the title product (720 mg). LC-MS (ESI); m/z 324 [M−H]$^+$; 3.95 min (ret time).

D6

2-[(4-{[4-chloro-3-(trifluoromethyl)phenyl]oxy}phenyl)oxy]-5-(2-hydroxyethyl)benzonitrile

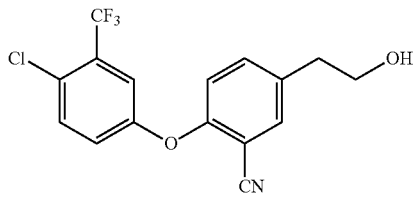 [SMILES: N#Cc1cc(CCO)ccc1Oc1ccc(Cl)c(C(F)(F)F)c1]

A mixture of 2-{[4-chloro-3-(trifluoromethyl)phenyl]oxy}-5-ethenylbenzonitrile (350 mg, 1.08 mmol) in anhydrous tetrahydrofuran (20 mL) was added 9-BBN (3.89 mL, 1.95 mmol) dropwise at 0° C. The reaction mixture was stirred at rt overnight, then sodium hydroxide (3.60 mL, 10.8 mmol) and $H_2O_2$ (0.199 mL, 1.95 mmol) were added at 0° C. The reaction mixture was stirred at 50° C. for 2 h, quenched with aq. $Na_2SO_3$ and concentrated. Purification via mass-directed autopreparation afforded the title product (150 mg). LC-MS (ESI): m/z 342 [M+H]$^+$; 3.33 min (ret time).

D7

2-(4-chloro-3-(trifluoromethyl)phenoxy)-5-(2-((2-chloropyrimidin-4-yl)oxy)ethyl)Benzonitrile

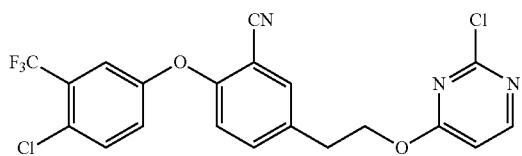 [SMILES: N#Cc1cc(CCOc2ccnc(Cl)n2)ccc1Oc1ccc(Cl)c(C(F)(F)F)c1]

The title compound was prepared by a procedure similar to that described for D3 starting from 2-{[4-chloro-3-(trifluoromethyl)phenyl]oxy}-5-(2-hydroxyethyl)benzonitrile. LC-MS (ESI): m/z 454 [M+H]$^+$; 3.99 min (ret time).

D8

2-[(4-{[4-chloro-3-(trifluoromethyl)phenyl]oxy}phenyl)oxy]-5-{2-[(2-oxo-2,3-dihydro-4-pyrimidinyl)oxy]ethyl}benzonitrile

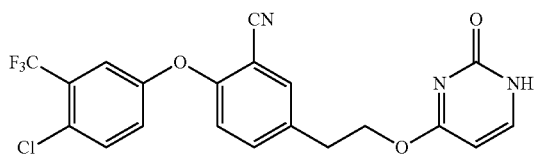 [SMILES: N#Cc1cc(CCOc2cc[nH]c(=O)n2)ccc1Oc1ccc(Cl)c(C(F)(F)F)c1]

The title compound was prepared by a procedure similar to that described for D4 starting from 2-[(4-{[4-chloro-3-(trifluoromethyl)phenyl]oxy}phenyl)oxy]-5-(2-hydroxyethyl)benzonitrile, LC-MS (ESI); m/z 454 [M+H]$^+$; 3.99 min (ret time).

D9

4-{[4-Chloro-3-(trifluoromethyl)phenyl]oxy}benzaldehyde

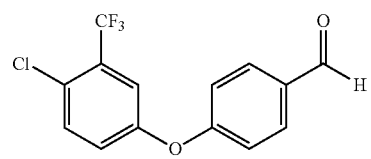

The title compound was prepared by a procedure similar to that described for D1 starting from 4-fluorobenzaldehyde and 4-Chloro-3-(trifluoromethyl)phenol. LC-MS (ESI): m/z 301 [M+H]$^+$; 3.76 min (ret time).

D10

(4-{[4-chloro-3-(trifluoromethyl)phenyl]oxy}phenyl)methanol

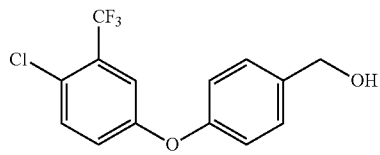 [SMILES: OCc1ccc(Oc2ccc(Cl)c(C(F)(F)F)c2)cc1]

The title compound was prepared by a procedure similar to that described for D2 starting from 4-{[4-chloro-3-(trifluoromethyl)phenyl]oxy}benzaldehyde. LC-MS (ESI): m/z 303 [M+H]$^+$; 3.43 min (ret time).

D11

2-chloro-4-{[(4-{[4-chloro-3-(1,1difluoroethyl)phenyl]oxy}phenyl)methyl]oxy}pyrimidine

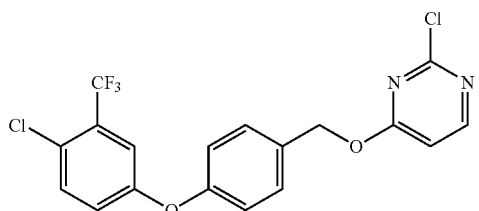

The title compound was prepared by a procedure similar to that described for D3 starting from (4-{[4-chloro-3-(trifluoromethyl)phenyl]oxy}phenyl)methanol and 2,4-dichloropyrimidine. LC-MS (ESI): m/z 415 [M+H]$^+$; 4.22 min (ret time).

D12

6-{[(4-{[4-Chloro-3-(1,1-difluoroethyl)phenyl]oxy}phenyl)methyl]oxy}-2(1H)-pyrimidinone

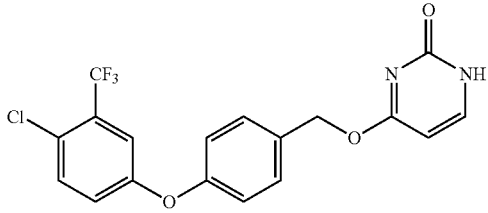 [SMILES: O=c1nc(OCc2ccc(Oc3ccc(Cl)c(C(F)(F)F)c3)cc2)cc[nH]1]

The title compound was prepared by a procedure similar to that described for D4 starting from 2-chloro-4-{[(4-{[4-chloro-3-(trifluoromethyl)phenyl]oxy}phenyl)methyl]oxy}pyrimidine. LC-MS (ESI): m/z 397 [M+H]$^+$; 3.34 min (ret time).

D13

4-Chloro-3-(trifluoromethyl)phenyl 4-ethenylphenyl ether

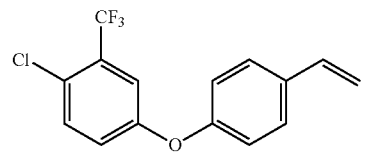 [SMILES: C=Cc1ccc(Oc2ccc(Cl)c(C(F)(F)F)c2)cc1]

The title compound was prepared by a procedure similar to that described for D5 starting from 4-{[4-chloro-3-(trifluoromethyl)phenyl]oxy}benzaldehyde. LC-MS (ESI): m/z 299 [M+H]$^+$; 5.07 min (ret time).

D14

2-(4-{[4-chloro-3-(trifluoromethyl)phenyl]oxy}phenyl)ethanol

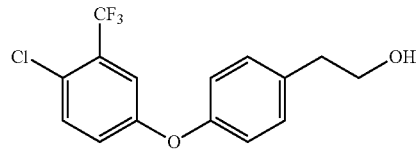 [SMILES: OCCc1ccc(Oc2ccc(Cl)c(C(F)(F)F)c2)cc1]

The title compound was prepared by a procedure similar to that described for D6 starting from 4-chloro-3-(trifluoromethyl)phenyl 4-ethenylphenyl ether. LC-MS (ESI): m/z 317 [M+H]$^+$; 3.56 min (ret time).

D15

2-chloro-4-{[2-(4-{[4-chloro-3-(trifluoromethyl)phenyl]oxy}phenyl)ethyl]oxy}pyrimidine

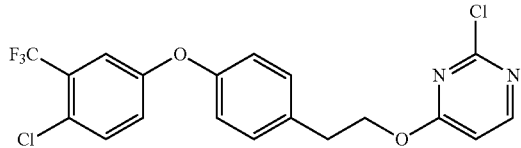 [SMILES: FC(F)(F)c1cc(Oc2ccc(CCOc3ccnc(Cl)n3)cc2)ccc1Cl]

The title compound was prepared by a procedure similar to that described for D3 starting from 2-chloro-4-{[2-(4-{[4-chloro-3-(trifluoromethyl)phenyl]oxy}phenyl)ethyl]oxy}pyrimidine. LC-MS (ESI): m/z 429 [M+H]$^+$; 4.32 min (ret time).

D16

6-{[2-(4-{[4-chloro-3-(trifluoromethyl)phenyl]oxy}phenyl)ethyl]oxy}-2(1H)-pyrimidinone

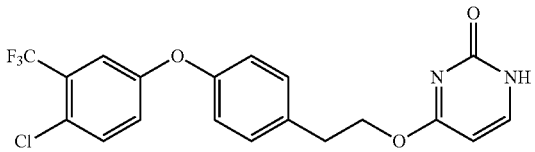 [SMILES: O=c1nc(OCCc2ccc(Oc3ccc(Cl)c(C(F)(F)F)c3)cc2)cc[nH]1]

The title compound was prepared by a procedure similar to that described for D4 starting from 2-chloro-4-{[2-(4-{[4-chloro-3-(trifluoromethyl)phenyl]oxy}phenyl)ethyl]oxy}pyrimidine. LC-MS (ESI): m/z 411 [M+H]$^+$; 4.15 min (ret time).

D17

5-(aminomethyl)-2-{[4-Chloro-3-(trifluoromethyl)phenyl]oxy}benzonitrile

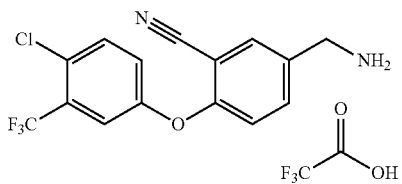

To a suspension of 2-{[4-chloro-3-(trifluoromethyl)phenyl]oxy}-5-formylbenzonitrile (1.0 g, 3.07 mmol) and ammonia (10 mL, 70.0 mmol) (7M in MeOH) in methanol (50 mL), was added Pd/C (0.327 g, 3.07 mmol). The reaction mixture was stirred at rt overnight under H$_2$ atmosphere, filtered and concentrated. Purification via MDAP afforded the title compound (500 mg). LC-MS (ESI): m/z 327 [M+H]$^+$; 2.49 min (ret time).

D18

5-{[(2-Chloro-4-pyrimidinyl)amino]methyl}-2-{[4-Chloro-3-(trifluoromethyl)phenyl]oxy}benzonitrile

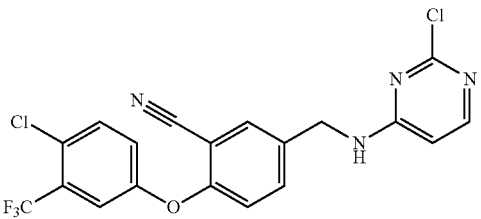 [SMILES: N#Cc1cc(CNc2ccnc(Cl)n2)ccc1Oc1ccc(Cl)c(C(F)(F)F)c1]

A solution of 5-(aminomethyl)-2-{[4-chloro-3-(trifluoromethyl)phenyl]oxy}benzonitrile (500 mg, 1.530 mmol), 2,4-dichloropyrimidine (239 mg, 1.607 mmol) and TEA (1.280 mL, 9.18 mmol) in the N,N-dimethylformamide (5 mL) was stirred at rt overnight. Purification via Biotage-C18 system afforded the title product (480 mg) as a white solid. LC-MS (ESI): m/z 439 [M+H]+; 3.56 min (ret time).

D19

2-{[4-Chloro-3-(trifluoromethyl)phenyl]oxy}-5-{[(2-oxo-1,2-dihydro-4-pyrimidinyl)amino]methyl}benzonitrile

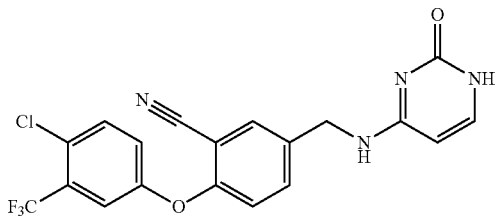 [SMILES: N#Cc1cc(CNc2cc[nH]c(=O)n2)ccc1Oc1ccc(Cl)c(C(F)(F)F)c1]

A mixture of 5-{[(2-chloro-4-pyrimidinyl)amino]methyl}-2-{[4-chloro-3-(trifluoromethyl)phenyl]oxy}benzonitrile (200 mg, 0.455 mmol), DABCO (25.5 mg, 0.228 mmol) and potassium carbonate (252 mg, 1.821 mmol) in a mixed solvents of 1,4-Dioxane (5 mL) and water (5.00 mL) was stirred at 80° C. overnight. Purification via MDAP, afforded the title compound (150 mg) as a white solid. LC-MS (ESI): m/z 421 [M+H]+; 2.63 min (ret time).

D20

5-{[4-chloro-3-(trifluoromethyl)phenyl]oxy}-2-pyridinecarbonitrile

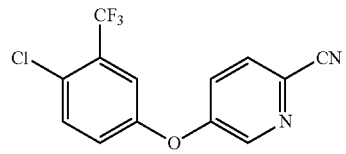 [SMILES: N#Cc1ccc(Oc2ccc(Cl)c(C(F)(F)F)c2)cn1]

The title compound was prepared by a procedure similar to that described for D1 starting from 5-fluoro-2-pyridinecarbonitrile and 4-chloro-3-(trifluoromethyl)phenol. LC-MS (ESI): m/z 299 [M+H]+; 3.59 min (ret time).

D21

5-{[4-chloro-3-(trifluoromethyl)phenyl]oxy}-2-pyridinecarbaldehyde

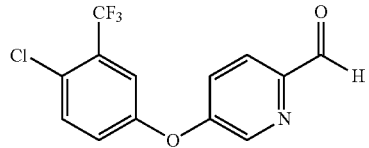

To a solution of 5-{[4-chloro-3-(trifluoromethyl)phenyl]oxy}-2-pyridinecarbonitrile (0.876 g, 2.93 mmol) in anhydrous tetrahydrofuran (30 mL), was added DIBAL-H (5.87 mL, 5.87 mmol) dropwise at −78° C. The reaction mixture was stirred for 1 h at −78° C., then quenched with 1N HCl solution, concentrated. Purification via ISCO afforded the title product (350 mg) as an off white solid. LC-MS (ESI): m/z 302 [M+H]+; 3.47 min (ret time).

D22

(5-{[4-Chloro-3-(trifluoromethyl)phenyl]oxy}-2-pyridinyl)methanol

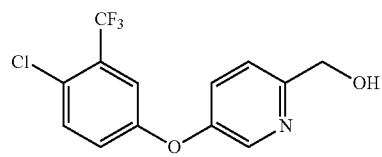 [SMILES: OCc1ccc(Oc2ccc(Cl)c(C(F)(F)F)c2)cn1]

The title compound was prepared by a procedure similar to that described for D2 starting from 5-{[4-Chloro-3-(trifluoromethyl)phenyl]oxy}-2-pyridinecarbaldehyde. LC-MS (ESI): m/z 304 [M+H]+; 2.71 min (ret time).

D23

2-chloro-4-{[(5-{[4-chloro-3-(trifluoromethyl)phenyl]oxy}-2-pyridinyl)methyl]oxy}pyrimidine

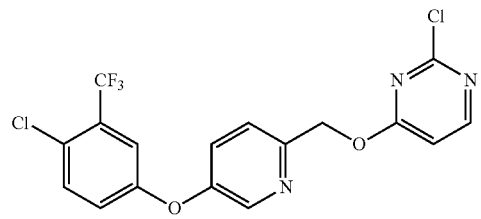

The title compound was prepared by a procedure similar to that described for D3 starting from (5-{[4-chloro-3-(trifluoromethyl)phenyl]oxy}-2-pyridinyl)methanol. LC-MS (ESI): m/z 416 [M+H]+; 3.79 min (ret time).

D24

6-{[(5-{[4-chloro-3-(1,1-difluoroethyl)phenyl]oxy}-2-pyridinyl)methyl]oxy}-2(1H)-pyrimidinone

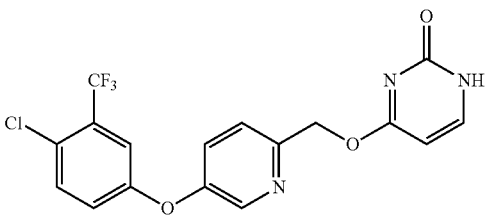

The title compound was prepared by a procedure similar to that described for D4 starting from 2-chloro-4-{[(5-{[4- chloro-3-(trifluoromethyl)phenyl]oxy}-2-pyridinyl)methyl]oxy}pyrimidine. LC-MS (ESI): m/z 398 [M+H]$^+$; 3.64 min (ret time).

D25

5-(Chloromethyl)-2-{[4-chloro-3-(trifluoromethyl)phenyl]oxy}benzonitrile

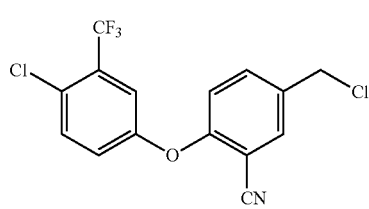 [SMILES: N#Cc1cc(CCl)ccc1Oc1ccc(Cl)c(C(F)(F)F)c1]

The title compound was prepared by a procedure similar to that described for D36 starting from 2-{[4-chloro-3-(trifluoromethyl)phenyl]oxy}-5-(hydroxymethyl)benzonitrile.

D26

2-{[4-Chloro-3-(trifluoromethyl)phenyl]oxy}-5-{[(2-oxo-1,2-dihydro-4-pyridinyl)oxy]methyl}benzonitrile

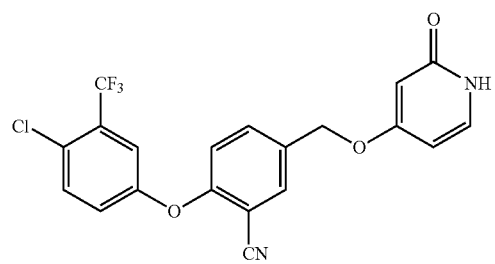 [SMILES: N#Cc1cc(COc2cc[nH]c(=O)c2)ccc1Oc1ccc(Cl)c(C(F)(F)F)c1]

The title compound was prepared by a procedure similar to that described for D37 starting from 5-(Chloromethyl)-2-{[4-chloro-3-(trifluoromethyl)phenyl]oxy}benzonitrile. LC-MS (ESI): m/z 421 [M+H]$^+$; 3.20 min (ret time).

D27

4-(Chloromethyl)phenyl 4-chloro-3-(trifluoromethyl)phenyl ether

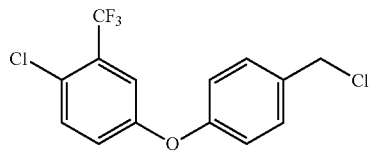 [SMILES: FC(F)(F)c1cc(Oc2ccc(CCl)cc2)ccc1Cl]

A solution of (4-{[4-chloro-3-(trifluoromethyl)phenyl]oxy}phenyl)methanol (200 mg, 0.661 mmol) in thionyl chloride (0.5 mL, 6.85 mmol) was stirred at rt for 1 h. Then the excess thionyl chloride was removed under vacuum to afford the title product (200 mg) as a yellow oil, which was used in the next reaction without purification. LC-MS (ESI): m/z 285 [M−Cl]$^+$; 4.17 min (ret time).

D28

4-{[(4-{[4-Chloro-3-(trifluoromethyl)phenyl]oxy}phenyl)methyl]oxy}-2(1H)-pyridinone

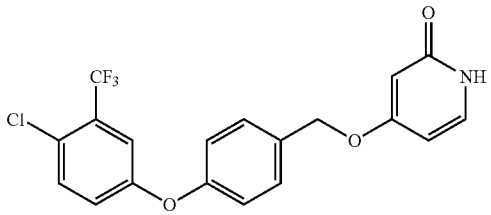

A solution of 4-(chloromethyl)phenyl 4-chloro-3-(trifluoromethyl)phenyl ether (500, mg, 1.557 mmol), potassium carbonate (500 mg, 3.62 mmol) and 2,4-dihydroxypyridine (350 mg, 3.15 mmol) in N,N-dimethylformamide (DMF) (5 mL) was heated at 60° C. for overnight, then cooled to rt and diluted with acetonitrile. Solid suspension was removed by filtration, concentrated. Purification via Biotage-C$_{18}$ system afforded the title product (310 mg) as a white solid. LC-MS (ESI): m/z 396 [M+H]$^+$; 3.48 min (ret time).

D29

4-(2-bromoethyl)phenyl 4-chloro-3-(trifluoromethyl)phenyl ether

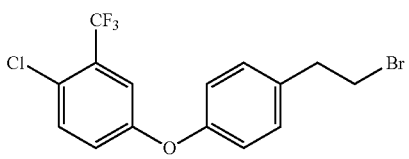 [SMILES: FC(F)(F)c1cc(Oc2ccc(CCBr)cc2)ccc1Cl]

To a solution of 2-(4-{[4-Chloro-3-(trifluoromethyl)phenyl]oxy}phenyl)ethanol (300 mg, 0.947 mmol) and triphenylphosphine (300 mg, 1.144 mmol) in dichloromethane (5 mL) was added carbon tetrabromide (350 mg, 1.055 mmol) in portions. The reaction mixture was stirred at rt for 2 h, then concentrated. Purification via ISCO system afforded the title product (335 mg) as a colorless liquid.

D30

4-{[2-(4-{[4-Chloro-3-(trifluoromethyl)phenyl]oxy}phenyl)ethyl]oxy}-2(1H)-pyridinone

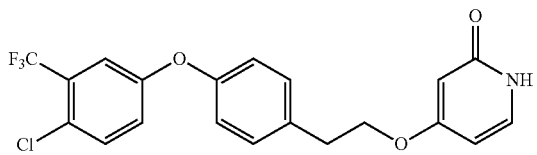 [SMILES: O=c1cc(OCCc2ccc(Oc3ccc(Cl)c(C(F)(F)F)c3)cc2)cc[nH]1]

A solution of 4-(2-bromoethyl)phenyl 4-Chloro-3-(trifluoromethyl)phenyl ether (335 mg, 0.883 mmol), 2,4-dihydroxypyridine (200 mg, 1.800 mmol), and cesium Carbonate (600 mg, 1.842 mmol) in N,N-dimethylformamide (DMF) (10 mL) was stirred at 120° C. for 4 h, then cooled to rt, Purification via Biotage-C$_{18}$ system afforded the title product (60 mg) as a white solid.

D31

5-Formyl-2-{[3-(trifluoromethyl)phenyl]oxy}benzonitrile

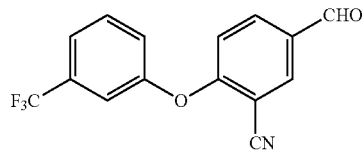 [SMILES: N#Cc1cc(C=O)ccc1Oc1cccc(C(F)(F)F)c1]

The title compound was prepared by a procedure similar to that described for D starting from 3-Trifluoromethyl-phenol and 2-Fluoro-5-formyl-benzonitrile.

D32

5-ethynyl-2-{[3-(trifluoromethyl)phenyl]oxy}benzonitrile

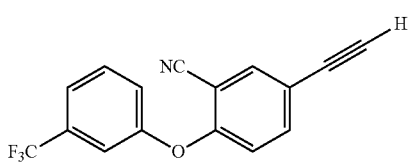 [SMILES: C#Cc1ccc(Oc2cccc(C(F)(F)F)c2)c(C#N)c1]

To a mixture of 5-formyl-2-{[3-(trifluoromethyl)phenyl]oxy}benzonitrile (1 g, 3.43 mmol) and dimethyl (1-diazo-2-oxopropyl)phosphonate (1.326 g, 6.87 mmol) in methanol (45 mL), was added potassium carbonate (2.373 g, 17.17 mmol) under argon. The reaction mixture was stirred for 1 h at rt, concentrated. The residue was dissolved in EtOAc (150 mL), washed with sat. ammonium hydrochloride solution (30 mL×3), water 30 mL, concentrated. Purification via ISCO system (EA/PE=1:20) afforded the title compound as a pale yellow oil. LC-MS (ESI): m/z 288 [M+H]$^+$; 3.71 min (ret time).

D33

5-[(2-Chloro-4-pyrimidinyl)ethynyl]-2-{[3-(trifluoromethyl)phenyl]oxy}benzonitrile

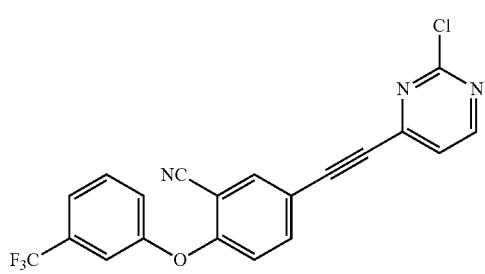 [SMILES: N#Cc1cc(C#Cc2ccnc(Cl)n2)ccc1Oc1cccc(C(F)(F)F)c1]

A mixture of copper(I) iodide (117 mg, 0.613 mmol), dichloropalladium-triphenylphosphane (1:2) (215 mg, 0.306 mmol), 2,4-dichloropyrimidine (913 mg, 6.13 mmol), and 5-ethynyl-2-{[3-(trifluoromethyl)phenyl]oxy}benzonitrile (880 mg, 3.06 mmol) in a mixed solvents of TEA (18 mL, 129 mmol) and tetrahydrofuran (12 mL), was added triphenylphosphine (161 mg, 0.613 mmol) under Argon. The reaction mixture was stirred for 12 h at 60° C., filtered, washed with EA, concentrated. Purification via ISCO system (EtOAc=1:20 to 1:5) afforded the title compound as a brown solid. LC-MS (ESI): m/z 400 [M+H]$^+$; 3.86 min (ret time).

D34

5-[2-(2-Chloro-4-pyrimidinyl)ethyl]-2-{[3-(triffluoromethyl)phenyl]oxy}benzonitrile

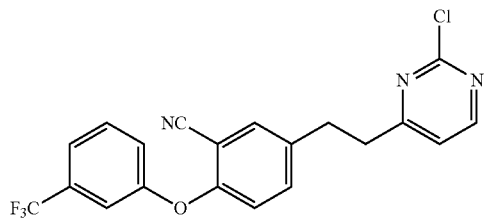 [SMILES: N#Cc1cc(CCc2ccnc(Cl)n2)ccc1Oc1cccc(C(F)(F)F)c1]

To a solution of 5-[(2-chloro-4-pyrimidinyl)ethynyl]-2-{[3-(trifluoromethyl)phenyl]oxy}benzo-nitrile (648 mg, 1.621 mmol), was added Pd/C (86 mg, 0.081 mmol). The reaction mixture was stirred for 1 h at rt under H$_2$ atmosphere, filtered, and concentrated to afford the title product as a pale yellow oil, which was used for next step without further purification. LC-MS (ESI): m/z 404 [M+H]$^+$; 3.76 min (ret time).

D35

5-[2-(2-oxo-1,2-dihydro-4-pyrimidinyl)ethyl]-2-{[3-(trifluoromethyl)phenyl]oxy}benzonitrile

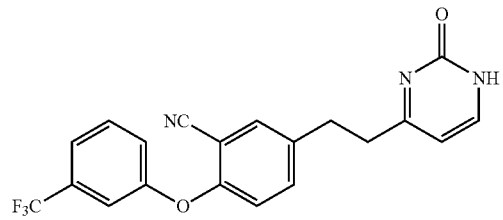 [SMILES: N#Cc1cc(CCc2cc[nH]c(=O)n2)ccc1Oc1cccc(C(F)(F)F)c1]

The title compound was prepared by a procedure similar to that described for D4 starting from 5-[2-(2-chloro-4-pyrimidinyl)ethyl]-2-{[3-(trifluoromethyl)phenyl]oxy}benzonitrile. LC-MS (EST): m/z 386 [M+H]$^+$; 2.74 min (ret time).

D36

2-chloro-5-(dibromomethyl)-3-fluoropyridine

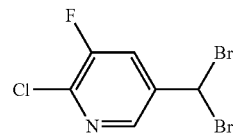

A suspension of 2-chloro-3-fluoro-5-methylpyridine (5.0 g, 34.3 mmol), dibenzoyl peroxide (1.109 g, 3.43 mmol) and NBS (18.34 g, 103 mmol) in CCl4 (100 mL) was refluxed for overnight, then cooled to rt and washed with water and brine, dried over sodium sulfate, concentrated. Purification via ISCO system afforded the title product (8.2 g) as a brown solid. LC-MS (ESI): m/z 300 [M+H]$^+$; 3.25 min (ret time).

D37

6-chloro-5-fluoro-3-pyridine carbaldehyde

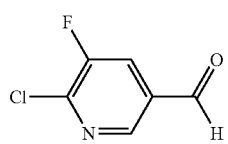

A suspension 2-chloro-5-(dibromomethyl)-3-fluoropyridine (2.3 g, 7.58 mmol), silver nitrate (5.15 g, 30.3 mmol) in a mixed solvents of ethanol (10 mL) and water (10 mL) was stirred for 1 h at 100° C., then filtrated, and concentrated. The residue was dissolved in ethyl acetate, washed with water and brine, dried over sodium sulfate, concentrated. Purification via ISCO system afforded the title product (1.0 g) as a pale solid. LC-MS (ESI): m/z 159 [M+H]$^+$; 2.01 min (ret time).

D38

6-{[4-chloro-3-(trifluoromethyl)phenyl]oxy}-5-fluoro-3-pyridinecarbaldehyde

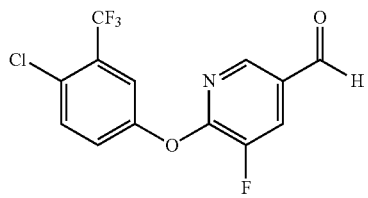 [SMILES: O=Cc1cnc(Oc2ccc(Cl)c(C(F)(F)F)c2)c(F)c1]

The title compound was prepared by a procedure similar to that described for D1 starting from 6-chloro-5-fluoro-3-pyridinecarbaldehyde and 4-chloro-3-(trifluoromethyl)phenol. LC-MS (ESI): m/z 320 [M+H]$^+$; 3.62 min (ret time).

D39

(6-{[4-chloro-3-(trifluoromethyl)phenyl]oxy}-S-fluoro-3-pyridinyl)methanol

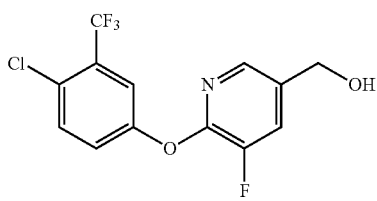 [SMILES: OCc1cnc(Oc2ccc(Cl)c(C(F)(F)F)c2)c(F)c1]

The title compound was prepared by a procedure similar to that described for D2 starting from 6-{[4-chloro-3-(trifluoromethyl)phenyl]oxy}-5-fluoro-3-pyridinecarbaldehyde, LC-MS (ESI): m/z 322 [M+H]$^+$; 3.52 min (ret time).

D40

2-chloro-4-{[(6-{[4-chloro-3-(trifluoromethyl)phenyl]oxy}-5-fluoro-3-pyridinyl)methyl]oxy}pyrimidine

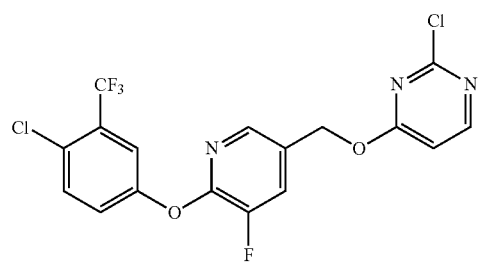 [SMILES: Fc1cc(COc2ccnc(Cl)n2)cnc1Oc1ccc(Cl)c(C(F)(F)F)c1]

The title compound was prepared by a procedure similar to that described for D3 starting from (6-{[4-chloro-3-(trifluoromethyl)phenyl]oxy}-5-fluoro-3-pyridinyl)methanol. LC-MS (ESI): m/z 434 [M+H]$^+$; 4.03 min (ret time).

D41

6-{[(6-{[4-chloro-3-(trifluoromethyl)phenyl]oxy}-5-fluoro-3-pyridinyl)methyl]oxy}-2(1H)-pyrimidinone

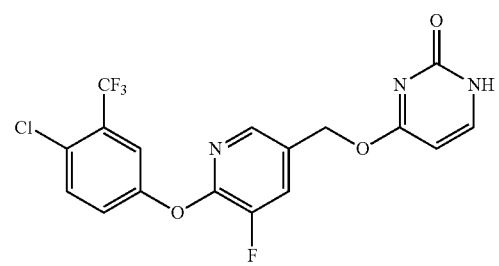 [SMILES: O=c1nc(OCc2cnc(Oc3ccc(Cl)c(C(F)(F)F)c3)c(F)c2)cc[nH]1]

The title compound was prepared by a procedure similar to that described for D4 starting from 2-chloro-4-{[(6-{[4-chloro-3-(trifluoromethyl)phenyl]oxy}-5-fluoro-3-pyridinyl)methyl]oxy}pyrimidine. LC-MS (ESI): m/z 416 [M+H]$^+$; 3.89 min (ret time).

D42

4-{[3-(Trifluoromethyl)phenyl]oxy}benzaldehyde

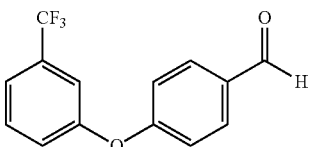

A solution of 3-(Trifluoromethyl)phenol (2.0 g, 12.34 mmol), 4-Fluorobenzaldehyde (2.0 g, 16.11 mmol), and Cs2CO3 (5.0 g, 15.35 mmol) in N,N-Dimethylformamide (DMF) (20 mL) was heated at 100° C. for 2 h, then cooled to rt. The solid suspension was removed by filtration over silica pad, and concentrated to afford crude title product (4.1 g) as a yellow liquid. LC-MS (ESI): m/z 267 [M+H]$^+$; 3.60 min (ret time).

D43

(4-{[3-(Trifluoromethyl)phenyl]oxy}phenyl)methanol

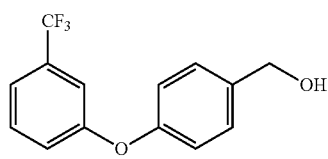 [SMILES: OCc1ccc(Oc2cccc(C(F)(F)F)c2)cc1]

A solution of 4-{[3-(Trifluoromethyl)phenyl]oxy}benzaldehyde (4.1 g, 9.55 mmol) in methanol (50 mL) at 0° C. was added sodium borohydride (1.0 g, 26.4 mmol) in portions. The reaction mixture was allowed to warm to rt and stirred for 1 h, then quenched with acetone, concentrated. Purification via ISCO system afforded the title product (3.11 g) as a colorless liquid. LC-MS (ESI): m/z 251 [M-OH]$^+$; 3.23 min (ret time).

D44

4-(chloromethyl)phenyl 3-(trifluoromethyl)phenyl ether

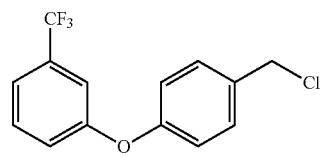 [SMILES: FC(F)(F)c1cccc(Oc2ccc(CCl)cc2)c1]

The title compound was prepared by a procedure similar to that described for D36 starting from (4-{[3-(Trifluoromethyl)phenyl]oxy}phenyl)methanol. LC-MS (ESI): m/z 251 [M-Cl]$^+$; 4.01 min (ret time).

D45

4-{[(4-{[3-(Trifluoromethyl)phenyl]oxy}phenyl)methyl]oxy}-2(1H)-pyridinone

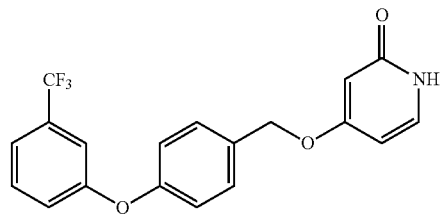 [SMILES: O=c1cc(OCc2ccc(Oc3cccc(C(F)(F)F)c3)cc2)cc[nH]1]

The title compound was prepared by a procedure similar to that described for D41 starting from 4-(chloromethyl)phenyl 3-(trifluoromethyl)phenyl ether, LC-MS (ESI): m/z 362 [M+H]$^+$; 3.26 min (ret time).

D46

2-{[4-chloro-3-(trifluoromethyl)phenyl]oxy}-5-ethenyl-3-fluoropyridine

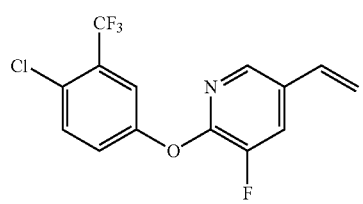 [SMILES: C=Cc1cnc(Oc2ccc(Cl)c(C(F)(F)F)c2)c(F)c1]

The title compound was prepared by a procedure similar to that described for D5 starting from 6-{[4-chloro-3-(trifluoromethyl)phenyl]oxy}-5-fluoro-3-pyridinecarbaldehyde. LC-MS (ESI): m/z 318 [M+H]$^+$; 4.05 min (ret time).

D47

2-(6-{[4-chloro-3-(trifluoromethyl)phenyl]oxy}-5-fluoro-3-pyridinyl)ethanol

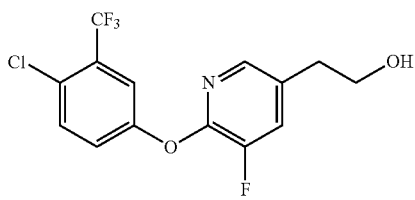 [SMILES: OCCc1cnc(Oc2ccc(Cl)c(C(F)(F)F)c2)c(F)c1]

The title compound was prepared by a procedure similar to that described for D6 starting from 2-{[4-chloro-3-(trifluoromethyl)phenyl]oxy}-5-ethenyl-3-fluoropyridine. LC-MS (ESI): m/z 336 [M+H]$^+$; 3.34 min (ret time).

D48

2-Chloro-4-{[2-(6-{[4-chloro-3-(trifluoromethyl)phenyl]oxy}-5-fluoro-3-pyridinyl)ethyl]oxy}pyrimidine

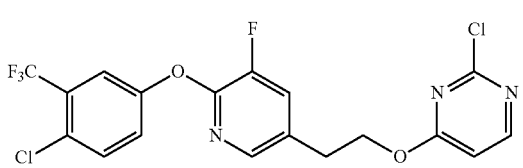 [SMILES: Fc1cc(CCOc2ccnc(Cl)n2)cnc1Oc1ccc(Cl)c(C(F)(F)F)c1]

The title compound was prepared by a procedure similar to that described for D3 starting from 2-(6-{[4-chloro-3-(trifluoromethyl)phenyl]oxy}-5-fluoro-3-pyridinyl)ethanol. LC-MS (ESI): m/z 448 [M+H]$^+$; 4.05 min (ret time).

D49

6-{[2-(6-{[4-Chloro-3-(trifluoromethyl)phenyl]oxy}-5-fluoro-3-pyridinyl)ethyl]oxy}-2(1H)pyrimidinone

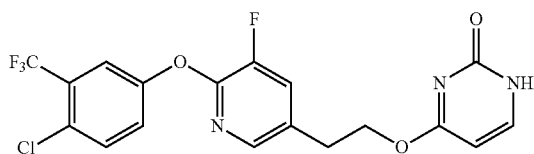 [SMILES: O=c1nc(OCCc2cnc(Oc3ccc(Cl)c(C(F)(F)F)c3)c(F)c2)cc[nH]1]

The title compound was prepared by a procedure similar to that described for D4 starting from 2-chloro-4-{[2-(6-{[4-chloro-3-(trifluoromethyl)phenyl]oxy}-5-fluoro-3-pyridinyl)ethyl]; oxy}pyrimidine. LC-MS (ESI): m/z 430 [M+H]⁺; 3.22 min (ret time).

D50

4-(Chloromethyl)phenyl 3-fluoro-4-methylphenyl ether

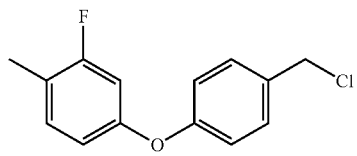 [SMILES: Cc1ccc(Oc2ccc(CCl)cc2)cc1F]

The title compound was prepared by a procedure similar to that described for D36 starting from {4-[(3-Fluoro-4-methylphenyl)oxy]phenyl}methanol. LC-MS (ESI): m/z 215 [M−Cl]⁺; 4.00 min (ret time).

D51

4-[({4-[(3-Fluoro-4-methylphenyl)oxy]phenyl}methyl)oxy]-2(1H)-pyridinone

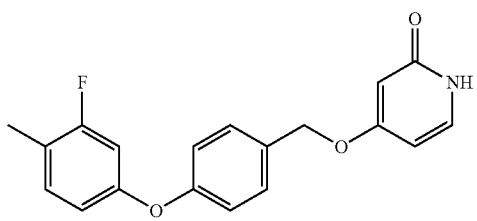 [SMILES: Cc1ccc(Oc2ccc(COc3cc[nH]c(=O)c3)cc2)cc1F]

The title compound was prepared by a procedure similar to that described for D37 starting from 4-(chloromethyl)phenyl 3-fluoro-4-methylphenyl ether. LC-MS (ESI): m/z 326 [M−Cl]⁺; 3.26 min (ret time).

D52

5-{[4-chloro-3-(trifluoromethyl)phenyl]oxy}-2-ethenylpyridine

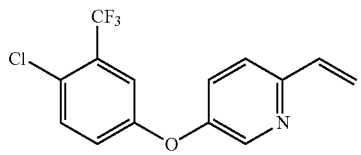

The title compound was prepared by a procedure similar to that described for D5 starting from 5-{[4-chloro-3-(trifluoromethyl)phenyl]oxy}-2-pyridinecarbaldehyde. LC-MS (ESI): m/z 300 [M+H]⁺; 3.48 min (ret time).

D53

2-(5-{[4-chloro-3-(trifluoromethyl)phenyl]oxy}-2-pyridinyl)ethanol

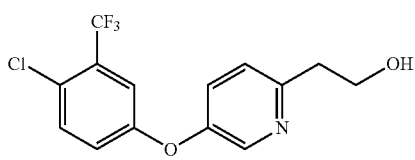

The title compound was prepared by a procedure similar to that described for D6 starting from 5-{[4-chloro-3-(trifluoromethyl)phenyl]oxy}-2-ethenylpyridine, LC-MS (ESI): m/z 318 [M+H]⁺; 2.53 min (ret time).

D54

2-chloro-4-{[2-(5-{[4-chloro-3-(trifluoromethyl)phenyl]oxy}-2-pyridinyl)ethyl]oxy}pyrimidine

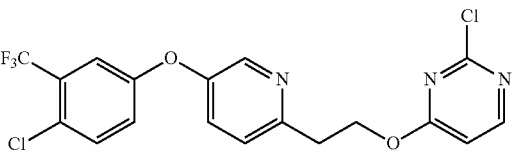

The title compound was prepared by a procedure similar to that described for D3 starting from 5-{[4-chloro-3-(trifluoromethyl)phenyl]oxy}-2-ethenylpyridine. LC-MS (ESI): m/z 430 [M+H]⁺; 3.55 min (ret time).

D55

6-{[2-(5-{[4-Chloro-3-(trifluoromethyl)phenyl]oxy}-2-pyridinyl)ethyl]oxy}-2(1H-pyrimidinone

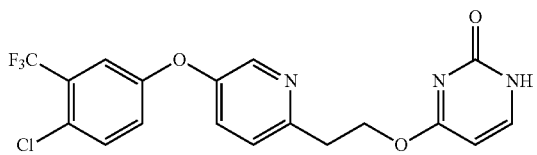 [SMILES: O=c1nc(OCCc2ccc(Oc3ccc(Cl)c(C(F)(F)F)c3)cn2)cc[nH]1]

The title compound was prepared by a procedure similar to that described for D4 starting from 5-{[4-chloro-3-(trifluoromethyl)phenyl]oxy}-2-ethenylpyridine. LC-MS (ESI); m/z 412 [M+H]+; 3.69 min (ret time),

D56

Pyridin-3-yl-acetic acid ethyl ester

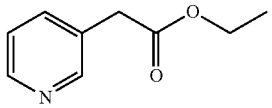

To a solution of 3-pyridylacetic acid hydrochloride (40 g, 230.41 mmol) in ethanol (90 mL) was added sulfuric acid (73 g, 744.3 mmole, 98%) under N2. The reaction mixture was refluxed for 4 h, then cooled to rt. Ammonium hydroxide (250 mL, 25%) was added and extracted with DCM (500 mL) twice, dried over sodium sulfate, concentrated to afford the title product (33 g),

D57

3-pyridinethanol

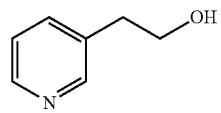

To a solution of pyridin-3-yl-acetic acid ethyl ester (33 g, 197.36 mmol) in methanol (400 mL) was added sodium borohydride (74.66 g, 1.9 mole). The reaction mixture was refluxed for 12 h, then cooled to rt, quenched with water (300 mL), concentrated. The residue was extracted with DCM (500 mL), dried over sodium sulfate, concentrated to afford the title product (20.76 g).

D58

2-ethyl-3-(4,4,5,5-tetramethyl-[1,3,2]dioxaborolan-2-yl)-benzaldehyde

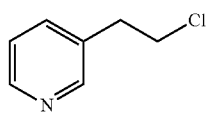

To a solution of 3-pyridinethanol (10 g, 81.20 mmol) in CHCl$_3$ (10 mL) was added thionyl chloride (10.11 g, 84.94 mmole) in CHCl$_3$ (15 mL). The reaction mixture was refluxed for 15 h, then concentrated. Sat. NaHCO$_3$ (100 mL) and CH$_2$Cl$_2$ (200 mL) were added to the residue. The separated organic layer was dried over sodium sulfate, concentrated. Purification via ISCO system afforded the title product (7.5 g).

D59

(1-Methyl-1H-pyrazol-4-yl)methanol

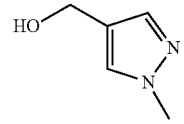

The title compound was prepared by a procedure similar to that described for D49 starting from 1-Methyl-1H-pyrazole-4-carboxaldehyde. LC-MS (ESI): m/z 113 [M+H]+; 1.30 min (ret time).

D60

4-(Chloromethyl)-1-methyl-1H-pyrazole

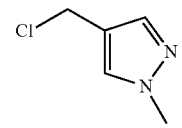

To a solution of (1-Methyl-1H-pyrazol-4-yl)methanol (1.1 g, 9.81 mmol) in dichloromethane (5.00 ml) was added thionyl chloride (2.0 ml, 27.4 mmol) in toluene (5.0 mL) dropwise. The reaction mixture was stirred for 1 hr at rt, concentrated to afford the title product (1.34 g) as a white solid, which was used in next reaction without purification.

D61

5-(Chloromethyl)pyrimidine

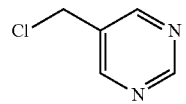

The title compound was prepared by a procedure similar to that described for D52 starting from 5-Pyrimidinemethanol. LC-MS (ESI): m/z 129 [M+H]+; 1.31 min (ret time).

D62

2-chloro-4-{[2-(4-{[4-chloro-3-(trifluoromethyl)phenyl]oxy}phenyl)ethyl]oxy}-5-fluoropyrimidine

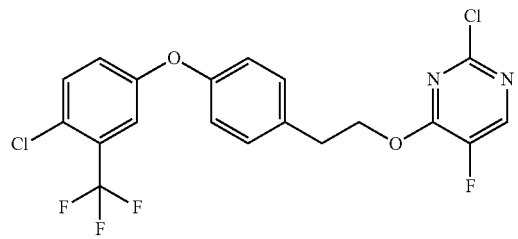

The title compound was prepared by a procedure similar to that described for D3 starting from 2-(4-{[4-chloro-3-(trifluoromethyl)phenyl]oxy}phenyl)ethanol. LC-MS (ESI): m/z 448 [M+H]+; 4.40 min (ret time),

D63

4-{[2-(4-{[4-Chloro-3-(trifluoromethyl)phenyl]oxy}phenyl)ethyl]oxy}-5-fluoro-2-[(phenylmethyl)oxy]pyrimidine

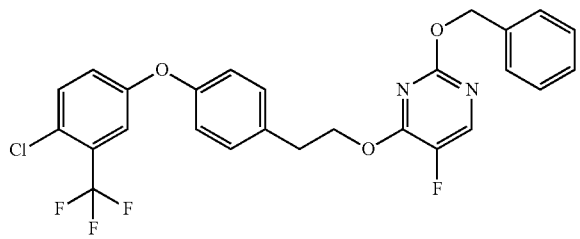 [SMILES: Fc1cnc(OCc2ccccc2)nc1OCCc1ccc(Oc2ccc(Cl)c(C(F)(F)F)c2)cc1]

To a solution of phenylmethanol (100 μL, 0.965 mmol) in N,N-dimethylformamide (DMF) (8 mL) was added sodium hydride (232 mg, 5.79 mmol) 0° C., the 2-chloro-4-{[2-(4-{[4-chloro-3-(trifluoromethyl)phenyl]oxy}phenyl)ethyl]oxy}-5-fluoropyrimidine (432 mg, 0.965 mmol) was added at 0° C. after 10 min. The reaction mixture was stirred for 30 min, and poured into ice-water (100 mL), extracted with ethyl acetate (50 mL) twice. Combined organic parts were washed with water and brine, dried over sodium sulfate, filtered and concentrated. Purification via ISCO system afforded the title product (370 mg). LC-MS (ESI): m/z 519[M+H]$^+$; 6.26 min (ret time).

D64

4-{[2-(4-{[4-chloro-3-(trifluoromethyl)phenyl]oxy}phenyl)ethyl]oxy}-5-fluoro-2(1H)-pyrimidinone

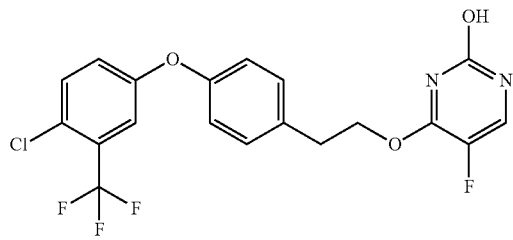

To a solution of 4-{[2-(4-{[4-chloro-3-(trifluoromethyl)phenyl]oxy}phenyl)ethyl]oxy}-5-fluoro-2-[(phenylmethyl)oxy]pyrimidine (240 mg, 0,463 mmol) in methanol (10 mL) was added wet Pd/C (24.61 mg, 0.023 mmol), the suspension was charged with hydrogen and stirred for 30 min, then filtrated. The solvent was removed in vacuum afforded title product (150 mg). LC-MS (ESI): m/z 429[M+H]$^+$; 4.22 min (ret time).

D65

5-chloro-4-{[2-(4-{[4-Chloro-3-(trifluoromethyl)phenyl]oxy}phenyl)ethyl]oxy}-2-[(phenylmethyl)oxy]pyrimidine

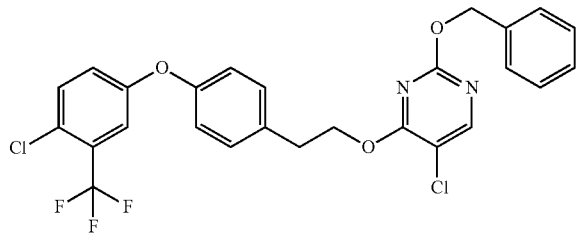 [SMILES: FC(F)(F)c1cc(Oc2ccc(CCOc3nc(OCc4ccccc4)ncc3Cl)cc2)ccc1Cl]

To a solution of 2-(4-{[4-chloro-3-(trifluoromethyl)phenyl]oxy}phenyl)ethanol (1.13 g, 3.57 m mol) in tetrahydrofuran (THF) (15 m L) was added Bu Li (2.342 m L, 3.75 m mol) in dropwise at 0° C., the solution was stirred for 10 min at r.t, then dropped to the solution of 2,4,5-trichloropyrimidine (0.409 m L, 3.57 m mol) in tetrahydrofuran (THF) (15 m L) at 0° C.

To a solution of phenyl methanol (0.370 m L, 3.57 m mol) in tetrahydrofuran (THF) (15 m L) was added BuLi (2.342 m L, 3.75 m mol) in prowise at 0° C. and stirred further 10 min at r.t. The result mixture was drop to previous solution and stirred further 30 min. The result mixture was quenched and concentrated in vacuum. The residue was purified via ISCO (hexane:ethyl acetate-5:1), removed the solvent afforded title compound (1.0 g). LC-MS (ESI): m/z 535 [M+H]$^+$; 2.06 min (ret time).

D66

5-chloro-4-(4-(4-chloro-3-(trifluoromethyl)phenoxy)phenethoxy)pyrimidin-2(1H)-one

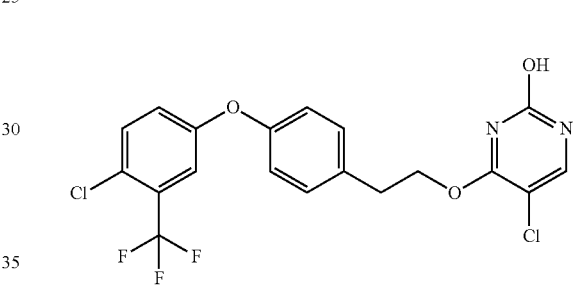

The title compound was prepared by a procedure similar to that described for D64 starting from 2-(benzyloxy)-5-fluoro-4-(4-((6-(trifluoromethyl)pyridin-2-yl)oxy)phenethoxy)pyrimidine. LC-MS (ESI): m/z 445 [M+H]$^+$; 4.35 min (ret time).

D67

2,5-dichloro-4-(2-(6-(4-chloro-3-(trifluoromethyl)phenoxy)-5-fluoropyridin-3-yl)ethoxy)pyrimidine

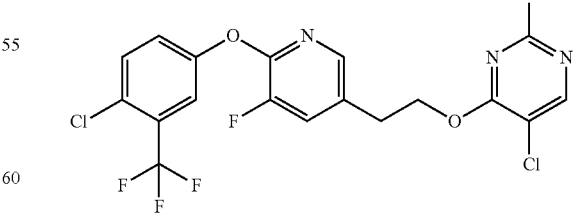

The title compound was prepared by a procedure similar to that described for D3 starting from 2-(6-(4-chloro-3-(trifluoromethyl)phenoxy)-5-fluoropyridin-3-yl)ethanol. LC-MS (ESI): m/z 481 [M+H]$^+$; 4.28 min (ret time).

D68

5-chloro-4-(2-(6-(4-chloro-3-(trifluoromethyl)phenoxy)-5-fluoropyridin-3-yl)ethoxy) pyrimidin-2-ol

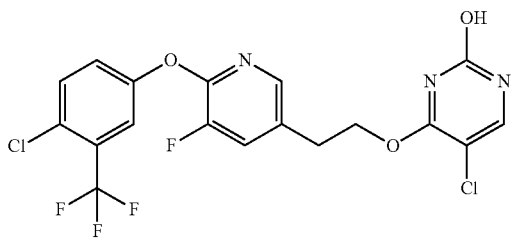 [SMILES: Oc1ncc(Cl)c(OCCc2cnc(Oc3ccc(Cl)c(C(F)(F)F)c3)c(F)c2)n1]

The title compound was prepared by a procedure similar to that described for D4 starting from 2,5-dichloro-4-(2-(6-(4-chloro-3-(trifluoromethyl)phenoxy)-5-fluoropyridin-3-yl)ethoxy) pyrimidine. LC-MS (ESI): m/z 481 [M+H]$^+$; 4.28 min (ret time).

D69

2-chloro-4-(2-(6-(4-Chloro-3-(trifluoromethyl)phenoxy)-5-fluoropyridin-3-yl)ethoxy)-5-fluoropyrimidine

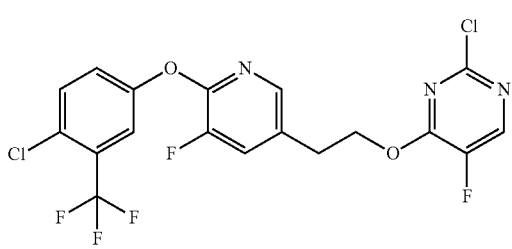 [SMILES: Fc1cnc(Cl)nc1OCCc1cnc(Oc2ccc(Cl)c(C(F)(F)F)c2)c(F)c1]

The title compound was prepared by a procedure similar to that described for D3 starting from 2-(6-(4-chloro-3-(trifluoromethyl)phenoxy)-5-fluoropyridin-3-yl)ethanol, LC-MS (ESI): m/z 467 [M+H]$^+$; 4.13 min (ret time).

D70

2-(benzyloxy)-4-(2-(6-(4-chloro-3-(trifluoromethyl)phenoxy)-5-fluoropyridin-3-yl)ethoxy)-5-fluoropyrimidine

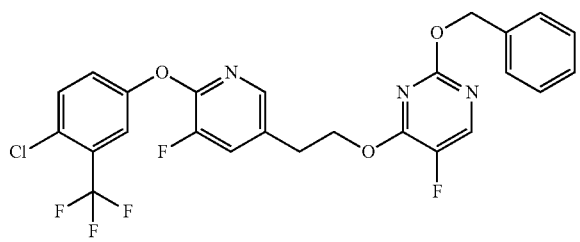 [SMILES: Fc1cnc(OCc2ccccc2)nc1OCCc1cnc(Oc2ccc(Cl)c(C(F)(F)F)c2)c(F)c1]

The title compound was prepared by a procedure similar to that described for D63 starting from 2-chloro-4-(2-(6-(4-chloro-3-(trifluoromethyl)phenoxy)-5-fluoropyridin-3-yl)ethoxy)-5-fluoro-pyrimidine. LC-MS (ESI): m/z 538 [M+H]$^+$; 5.88 min (ret time).

D71

4-(2-(6-(4-chloro-3-(trifluoromethyl)phenoxy)-5-fluoropyridin-3-yl)ethoxy)-5-fluoropyrimidin-2(1H)-one

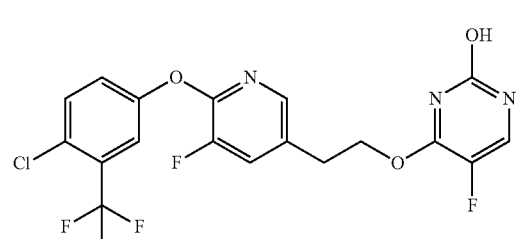

The title compound was prepared by a procedure similar to that described for D64 starting from 2-(benzyloxy)-4-(2-(6-(4-chloro-3-(trifluoromethyl)phenoxy)-5-fluoropyridin-3-yl)ethoxy)-5-fluoropyrimidine. LC-MS (ESI): m/z 538 [M+H]$^+$; 4.26 min (ret time).

D72

4'-(trifluoromethyl)-4-biphenylcarbaldehyde

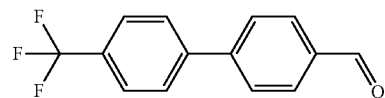

The title compound was prepared by a procedure similar to that described for D83 starting from [4-(trifluoromethyl)phenyl]boronic acid and 4-bromobenzaldehyde. LC-MS (ESI): m/z 251 [M+H]$^+$; 3.63 min (ret time).

D73

4-ethenyl-4'-(trifluoromethyl)biphenyl

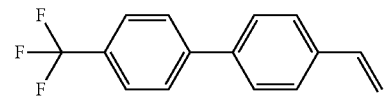

The title compound was prepared by a procedure similar to that described for D5 starting 4'-(trifluoromethyl)-4-biphenylcarbaldehyde. LC-MS (ESI): m/z 249 [M+H]$^+$; 5.76 min (ret time).

D74

2-(4'-(trifluoromethyl)-[1,1'-biphenyl]-4-yl)ethanol

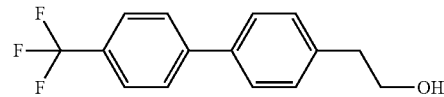

The title compound was prepared by a procedure similar to that described for D6 starting 4-ethenyl-4'-(trifluoromethyl)biphenyl. LC-MS (ESI): m/z 249 [M+H]$^+$; 4.36 min (ret time).

D75

5-chloro-4-(2-(4'-(trifluoromethyl)-[1,1'-biphenyl]-4-yl)ethoxy)pyrimidin-2(1H)-one

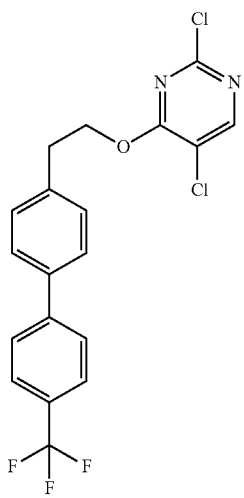 [SMILES: FC(F)(F)c1ccc(-c2ccc(CCOc3nc(Cl)ncc3Cl)cc2)cc1]

The title compound was prepared by a procedure similar to that described for D3 starting 2-(4'-(trifluoromethyl)-[1,1'-biphenyl]-4-yl)ethanol. LC-MS (ESI): m/z 413 [M+H]$^+$; 4.41 min (ret time).

D76

5-chloro-4-(2-(4'-(trifluoromethyl)-[1,1'-biphenyl]-4-yl)ethoxy)pyrimidin-2(1H)-one

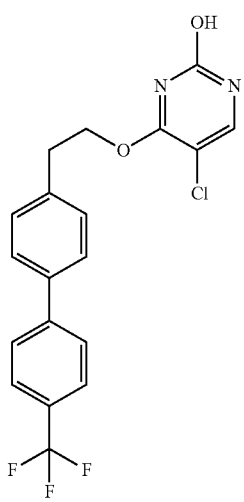 [SMILES: Oc1ncc(Cl)c(OCCc2ccc(-c3ccc(C(F)(F)F)cc3)cc2)n1]

The title compound was prepared by a procedure similar to that described for D4 starting 2,5-dichloro-4-(2-(4'-(trifluoromethyl)-[1,1'-biphenyl]-4-yl)ethoxy)pyrimidine, LC-MS (ESI): m/z 395 [M+H]$^+$; 3.49 min (ret time),

D77

5-fluoro-6-(4-fluoro-3-(trifluoromethyl)phenoxy)nicotinaldehyde

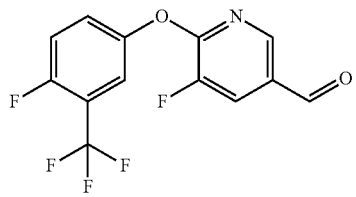 [SMILES: O=Cc1cnc(Oc2ccc(F)c(C(F)(F)F)c2)c(F)c1]

The title compound was prepared by a procedure similar to that described for D1 starting from 6-chloro-5-fluoronicotinaldehyde. LC-MS (ESI): m/z 304 [M+H]$^+$; 3.44 min (ret time).

D78

3-fluoro-2-(4-fluoro-3-(trifluoromethyl)phenoxy)-5-vinylpyridine

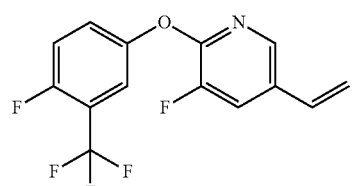

The title compound was prepared by a procedure similar to that described for D5 starting 5-fluoro-6-(4-fluoro-3-(trifluoromethyl)phenoxy)nicotinaldehyde. LC-MS (ESI): m/z 302 [M+H]$^+$; 3.44 min (ret time).

D79

2-(5-fluoro-6-(4-fluoro-3-(trifluoromethyl)phenoxy)pyridin-3-yl)ethanol

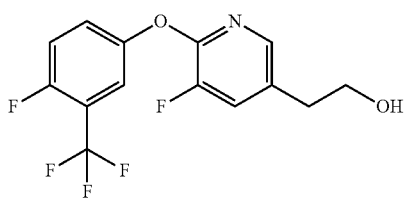 [SMILES: OCCc1cnc(Oc2ccc(F)c(C(F)(F)F)c2)c(F)c1]

The title compound was prepared by a procedure similar to that described for D6 starting 3-fluoro-2-(4-fluoro-3-(trifluoromethyl)phenoxy)-5-vinylpyridine. LC-MS (ESI): m/z 320 [M+H]$^+$; 4.04 min (ret time).

D80

2,5-dichloro-4-(2-(5-fluoro-6-(4-fluoro-3-(trifluoromethyl)phenoxy)pyridin-3-yl)ethoxy)pyrimidine

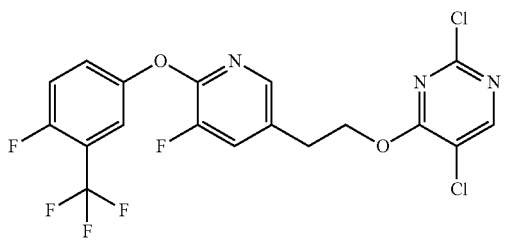 [SMILES: Fc1ccc(Oc2ncc(CCOc3nc(Cl)ncc3Cl)cc2F)cc1C(F)(F)F]

The title compound was prepared by a procedure similar to that described for D3 starting 2-(5-fluoro-6-(4-fluoro-3-(trifluoromethyl)phenoxy)pyridin-3-yl)ethanol. LC-MS (ESI): m/z 466 [M+H]$^+$; 4.09 min (ret time).

D81

5-chloro-4-(2-(5-fluoro-6-(4-fluoro-3-(trifluoromethyl)phenoxy)pyridin-3-yl)ethoxy) pyrimidin-2(1H)-one

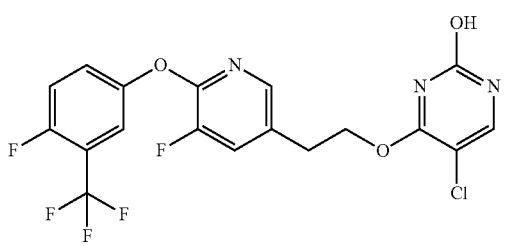

The title compound was prepared by a procedure similar to that described for D4 starting 2,5-dichloro-4-(2-(5-fluoro-6-(4-fluoro-3-(trifluoromethyl)phenoxy)pyridin-3-yl)ethoxy) pyrimidine. LC-MS (ESI): m/z 447 [M+H]$^+$; 3.91 min (ret time).

D82

2-chloro-5-fluoro-4-(2-(6-(4-fluoro-3-(trifluoromethyl)phenoxy)pyridin-3-yl)ethoxy)pyrimidine

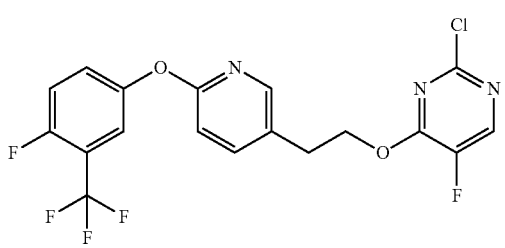 [SMILES: Fc1ccc(Oc2ccc(CCOc3nc(Cl)ncc3F)cn2)cc1C(F)(F)F]

The title compound was prepared by a procedure similar to that described for D3 starting from 2-(6-(4-fluoro-3-(trifluoromethyl)phenoxy)pyridin-3-yl)ethanol. LC-MS (ESI): m/z 432 [M+H]$^+$; 3.94 min (ret time).

D83

2-(benzyloxy)-5-fluoro-4-(2-(6-(4-fluoro-3-(trifluoromethyl)phenoxy)pyridin-3-yl)ethoxy)pyrimidine

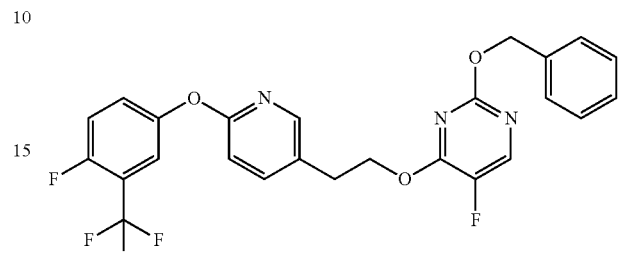

The title compound was prepared by a procedure similar to that described for D63 starting from 2-chloro-5-fluoro-4-(2-(6-(4-fluoro-3-(trifluoromethyl)phenoxy)pyridin-3-yl)ethoxy)pyrimidine. LC-MS (ESI): m/z 504 [M+H]$^+$; 4.24 min (ret time).

D84

5-fluoro-4-(2-(6-(4-fluoro-3-(trifluoromethyl)phenoxy)pyridin-3-yl)ethoxy)pyrimidin-2(1H)-one

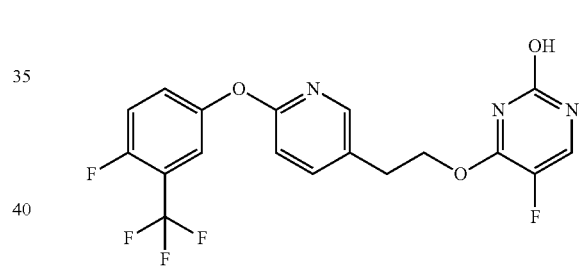

The title compound was prepared by a procedure similar to that described for D64 starting from 2-(benzyloxy)-5-fluoro-4-(2-(6-(4-fluoro-3-(trifluoromethyl)phenoxy)pyridin-3-yl) ethoxy) pyrimidine. LC-MS (ESI): m/z 413 [M+H]$^+$; 3.02 min (ret time).

D85

2-chloro-4-(2-(6-(4-chloro-3-(trifluoromethyl)phenoxy)pyridin-3-yl)ethoxy)-5-fluoropyrimidine

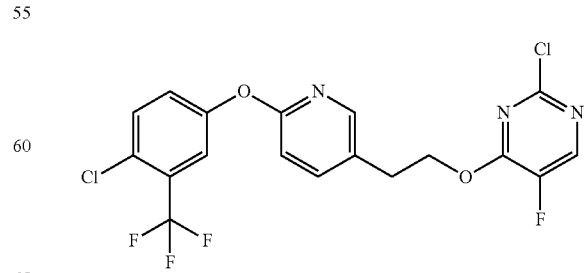

The title compound was prepared by a procedure similar to that described for D3 starting from 2-(6-(4-chloro-3-(trifluoromethyl)phenoxy)pyridin-3-yl)ethanol. LC-MS (ESI): m/z 448 [M+H]⁺; 4.11 min (ret time).

D86

2-(benzyloxy)-4-(2-(6-(4-chloro-3-(trifluoromethyl) phenoxy)pyridin-3-yl)ethoxy)-5-fluoropyrimidine

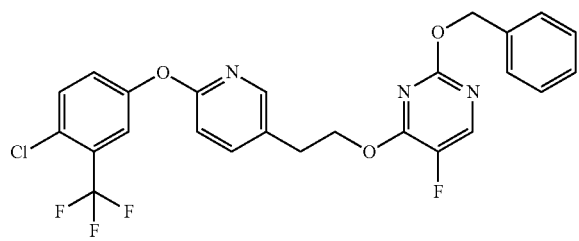 [SMILES: Fc1cnc(OCc2ccccc2)nc1OCCc1ccc(Oc2ccc(Cl)c(C(F)(F)F)c2)nc1]

The title compound was prepared by a procedure similar to that described for D63 starting from 2-chloro-4-(2-(6-(4-chloro-3-(trifluoromethyl)phenoxy)pyridin-3-yl)ethoxy)-5-fluoropyrimidine. LC-MS (ESI): m/z 520 [M+H]⁺; 4.37 min (ret time).

D87

4-(2-(6-(4-chloro-3-(trifluoromethyl)phenoxy)pyridin-3-yl)ethoxy)-5-fluoropyrimidin-2(1H)-one

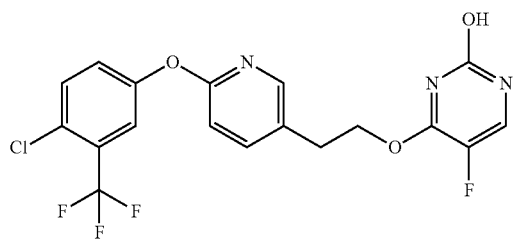 [SMILES: Oc1ncc(F)c(OCCc2ccc(Oc3ccc(Cl)c(C(F)(F)F)c3)nc2)n1]

The title compound was prepared by a procedure similar to that described for D64 starting from 2-(benzyloxy)-4-(2-(6-(4-chloro-3-(trifluoromethyl)phenoxy)pyridin-3-yl)ethoxy)-5-fluoro pyrimidine. LC-MS (ESI): m/z 430 [M+H]⁺; 3.19 min (ret time).

D88

2-chloro-5-fluoro-4-(3-fluoro-4-((6-(trifluoromethyl) pyridin-3-yl)oxy)phenethoxy)pyrimidine

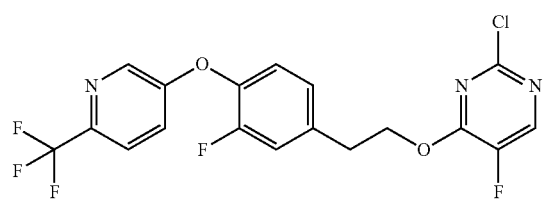 [SMILES: Fc1cc(CCOc2nc(Cl)ncc2F)ccc1Oc1ccc(C(F)(F)F)nc1]

The title compound was prepared by a procedure similar to that described for D3 starting from 2-(3-fluoro-4-((6-(trifluoromethyl)pyridin-3-yl)oxy)phenyl)ethanol. LC-MS (ESI): m/z 432 [M+H]⁺; 3.93 min (ret time).

D89

2-(benzyloxy)-5-fluoro-4-(3-fluoro-4-((6-(trifluoromethyl)pyridin-3-yl)oxy)phenethoxy)pyrimidine

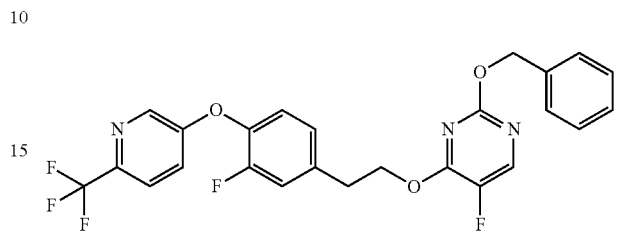

The title compound was prepared by a procedure similar to that described for D63 starting from 2-chloro-5-fluoro-4-(3-fluoro-4-((6-(trifluoromethyl)pyridin-3-yl)oxy)phenethoxy) pyrimidine, LC-MS (ESI): m/z 504 [M+H]⁺; 4.21 min (ret time).

D90

5-fluoro-4-(3-fluoro-4-((6-(trifluoromethyl)pyridin-3-yl)oxy)phenethoxy)pyrimidin-2(1H)-one

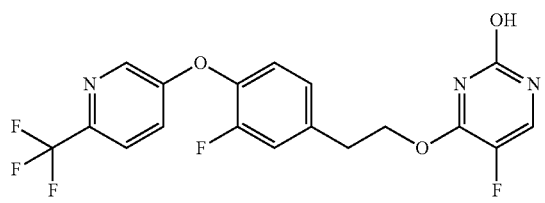 [SMILES: Oc1ncc(F)c(OCCc2ccc(Oc3ccc(C(F)(F)F)nc3)c(F)c2)n1]

The title compound was prepared by a procedure similar to that described for D64 starting from 2-(benzyloxy)-5-fluoro-4-(3-fluoro-4-((6-(trifluoromethyl)pyridin-3-yl)oxy) phenethoxy) pyrimidine. LC-MS (ESI): m/z 414 [M+H]⁺; 3.00 min (ret time).

D91

2-chloro-5-fluoro-4-(2-(5-fluoro-6-(4-fluoro-3-(trifluoromethyl)phenoxy)pyridiu-3-yl)ethoxy)pyrimidine

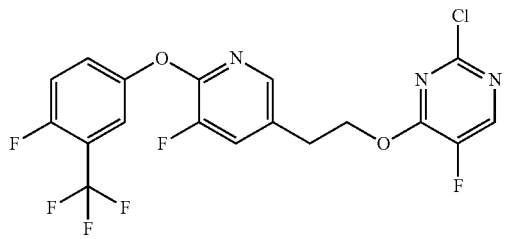 [SMILES: Fc1ccc(Oc2ncc(CCOc3nc(Cl)ncc3F)cc2F)cc1C(F)(F)F]

The title compound was prepared by a procedure similar to that described for D3 starting from 2-(5-fluoro-6-(4-fluoro- 3-(trifluoromethyl)phenoxy)pyridin-3-yl)ethanol. LC-MS (ESI): m/z [M+H]+, 4.04 min (ret time).

D92

2-(benzyloxy)-5-fluoro-4-(2-(5-fluoro-6-(4-fluoro-3-(trifluoromethyl)phenoxy)pyridin-3-yl)ethoxy)pyrimidine

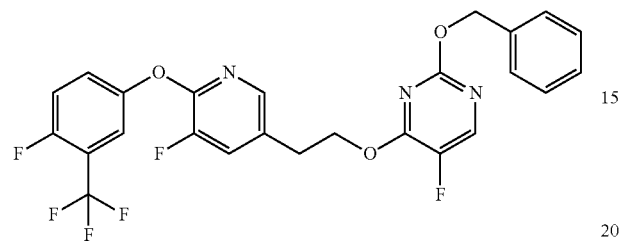

The title compound was prepared by a procedure similar to that described for D63 starting from 2-chloro-5-fluoro-4-(2-(5-fluoro-6-(4-fluoro-3-(trifluoromethyl)phenoxy)pyridin-3-yl)ethoxy)pyrimidine. LC-MS (ESI): m/z 522 [M+H]+, 4.19 min (ret time).

D93

5-fluoro-4-(2-(5-fluoro-6-(4-fluoro-3-(trifluoromethyl)phenoxy)pyridin-3-yl)ethoxy) pyrimidin-2(1H)-one

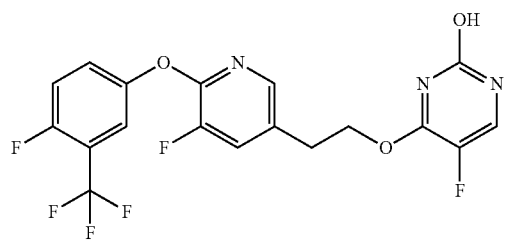 [SMILES: Oc1ncc(F)c(OCCc2cnc(Oc3ccc(F)c(C(F)(F)F)c3)c(F)c2)n1]

The title compound was prepared by a procedure similar to that described for D64 starting from 2-(benzyloxy)-5-fluoro-4-(2-(5-fluoro-6-(4-fluoro-3-(trifluoromethyl)phenoxy)pyridin-3-yl) ethoxy)pyrimidine. LC-MS (ESI): m/z 432 [M+H]+, 3.17 min (ret time).

D94

4-(4-chloro-3-(trifluoromethyl)benzyl)benzaldehyde

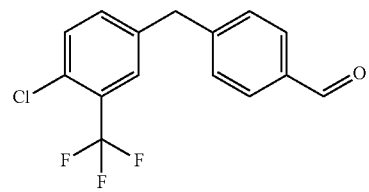 [SMILES: O=Cc1ccc(Cc2ccc(Cl)c(C(F)(F)F)c2)cc1]

To a suspension of 4-(bromomethyl)-1-chloro-2-(trifluoromethyl)benzene (4.5 g, 16.45 mmol), potassium trifluoro(4-formylphenyl)borate (3.52 g, 16.62 mmol), PdCl2(dppf)-CH2Cl2 adduct (0.672 g, 0.823 mmol) and Cs2CO3 (16.08 g, 49.4 mmol) in cyclopentyl methyl ether (100 mL) and water (100 mL). The mixture was charged with Argon and stirred for overnight at 80° C. The result mixture was cooled to room temperature and partitioned with water 100 mL and ethyl acetate 100 mL. The organic phase was washed by water, brine and dried over sodium sulfate, the solvent was removed and the residue was purified via flash column chromatography. Removed the solvent afforded the title compound (2.55 g). LC-MS (ESI): m/z 299 [M+H]+

D95

1-chloro-2-(trifluoromethyl)-4-(4-vinylbenzyl)benzene

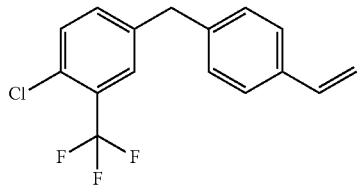 [SMILES: C=Cc1ccc(Cc2ccc(Cl)c(C(F)(F)F)c2)cc1]

The title compound was prepared by a procedure similar to that described for D5 starting 4-(4-chloro-3-(trifluoromethyl)benzyl)benzaldehyde. LC-MS (ESI): m/z 297 [M+H]+; 4.11 min (ret time).

D96

2-(4-(4-chloro-3-(trifluoromethyl)benzyl)phenyl)ethanol

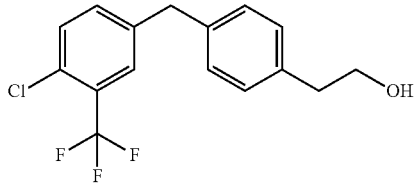 [SMILES: OCCc1ccc(Cc2ccc(Cl)c(C(F)(F)F)c2)cc1]

The title compound was prepared by a procedure similar to that described for D6 starting 1-Chloro-2-(trifluoromethyl)-4-(4-vinylbenzyl)benzene. LC-MS (ESI): m/z 315 [M+H]+; 3.60 min (ret time).

D97

2,5-diChloro-4-(4-(4-Chloro-3-(trifluoromethyl)benzyl)phenethoxy)pyrimidine

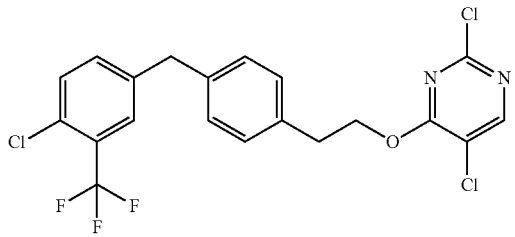 [SMILES: FC(F)(F)c1cc(Cc2ccc(CCOc3nc(Cl)ncc3Cl)cc2)ccc1Cl]

The title compound was prepared by a procedure similar to that described for D3 starting 2-(4-(4-chloro-3-(trifluoromethyl)benzyl)phenyl)ethanol. LC-MS (ESI): m/z 461 [M+H]⁺; 4.55 min (ret time).

D98

5-chloro-4-(4-(4-chloro-3-(trifluoromethyl)benzyl)phenethoxy)pyrimidin-2(1H)-one

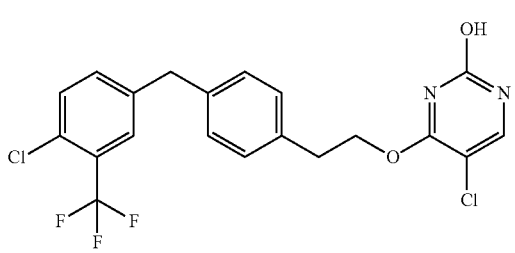

The title compound was prepared by a procedure similar to that described for D4 starting 2,5-dichloro-4-(4-(4-chloro-3-(trifluoromethyl)benzyl)phenethoxy)pyrimidine. LC-MS (ESI); m/z 443 [M+H]⁺; 3.66 min (ret time).

D99

2-chloro-4-(4-(4-chloro-3-(trifluoromethyl)benzyl)phenethoxy)-S-fluoropyrimidine

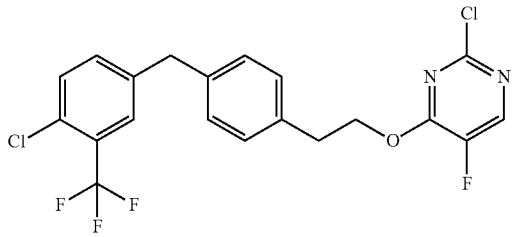 [SMILES: Fc1cnc(Cl)nc1OCCc1ccc(Cc2ccc(Cl)c(C(F)(F)F)c2)cc1]

The title compound was prepared by a procedure similar to that described for D3 starting from 2-(4-(4-chloro-3-(trifluoromethyl)benzyl)phenyl)ethanol. LC-MS (ESI): m/z 445 [M+H]⁺; 4.40 min (ret time).

D100

2-(benzyloxy)-4-(4-(4-chloro-3-(trifluoromethyl)benzyl)phenethoxy)-5-fluoropyrimidine

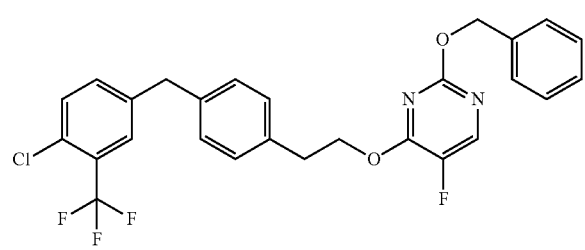 [SMILES: Fc1cnc(OCc2ccccc2)nc1OCCc1ccc(Cc2ccc(Cl)c(C(F)(F)F)c2)cc1]

The title compound was prepared by a procedure similar to that described for D63 starting from 2-chloro-4-(4-(4-chloro-3-(trifluoromethyl)benzyl)phenethoxy)-5-fluoropyrimidine, LC-MS (ESI): m/z 517 [M+H]⁺; 4.56 min (ret time).

D101

4-(4-(4-Chloro-3-(trifluoromethyl)benzyl)phenethoxy)-5-fluoropyrimidin-2(1H)-one

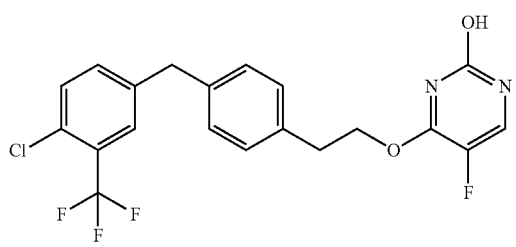 [SMILES: Oc1ncc(F)c(OCCc2ccc(Cc3ccc(Cl)c(C(F)(F)F)c3)cc2)n1]

The title compound was prepared by a procedure similar to that described for D64 starting from 2-(benzyloxy)-4-(4-(4-chloro-3-(trifluoromethyl)benzyl)phenethoxy)-5-fluoropyrimidine. LC-MS (ESI): m/z 427 [M+H]⁺; 4.24 min (ret time).

D102

2-(4-((4-(trifluoromethyl)pyrimidin-2-yl)oxy)phenyl)ethanol

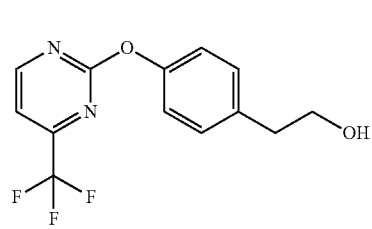 [SMILES: OCCc1ccc(Oc2nccc(C(F)(F)F)n2)cc1]

The title compound was prepared by a procedure similar to that described for D1 starting from 4-(2-hydroxyethyl)phenol and 2-chloro-4-(trifluoromethyl)pyrimidine. LC-MS (ESI): m/z 285 [M+H]⁺; 2.66 min (ret time).

D103

2,5-dichloro-4-(4-((4-(trifluoromethyl)pyrimidin-2-yl)oxy)phenethoxy)pyrimidine

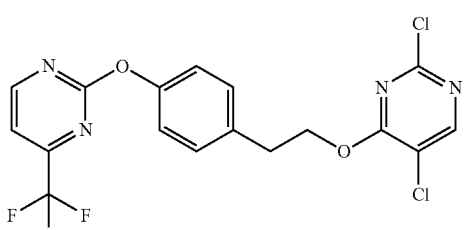

The title compound was prepared by a procedure similar to that described for D3 starting 2-(4-((4-(trifluoromethyl)pyrimidin-2-yl)oxy)phenyl)ethanol. LC-MS (ESI): m/z 431 [M+H]$^+$; 3.85 min (ret time).

D104

5-chloro-4-(4-((4-(trifluoromethyl)pyrimidin-2-yl)oxy)phenethoxy)pyrimidin-2(1H)-one

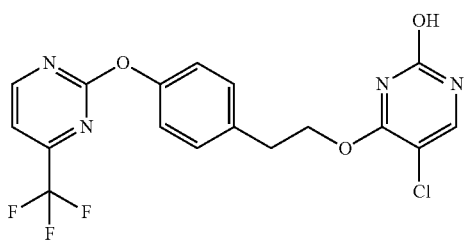 [SMILES: Oc1ncc(Cl)c(OCCc2ccc(Oc3nccc(C(F)(F)F)n3)cc2)n1]

The title compound was prepared by a procedure similar to that described for D4 starting 2,5-dichloro-4-(4-((4-(trifluoromethyl)pyrimidin-2-yl)oxy)phenethoxy)pyrimidine. LC-MS (ESI): m/z 413 [M+H]$^+$; 2.87 min (ret time).

D105

2-(4-((5-(trifluoromethyl)pyridin-2-yl)oxy)phenyl)ethanol

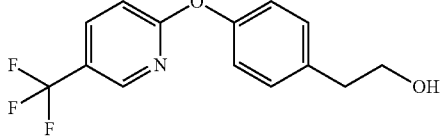

The title compound was prepared by a procedure similar to that described for D3 starting from 4-(2-hydroxyethyl)phenol and 2-chloro-5-(trifluoromethyl)pyridine. LC-MS (ESI): m/z 284 [M+H]$^+$; 2.97 min (ret time).

D106

2,5-dichloro-4-(4-((5-(trifluoromethyl)pyridin-2-yl)oxy)phenethoxy)pyrimidine

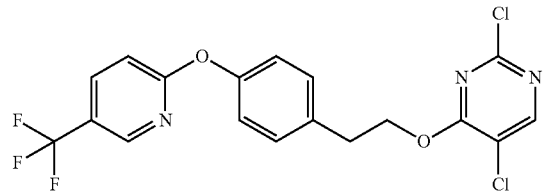

The title compound was prepared by a procedure similar to that described for D3 starting 2-(4-((5-(trifluoromethyl)pyridin-2-yl)oxy)phenyl)ethanol. LC-MS (ESI): m/z 430 [M+H]$^+$; 4.14 min (ret time).

D107

5-chloro-4-((4-(3,4-difluorophenoxy)-3-fluorobenzyl)oxy)pyrimidin-2(1H)-one

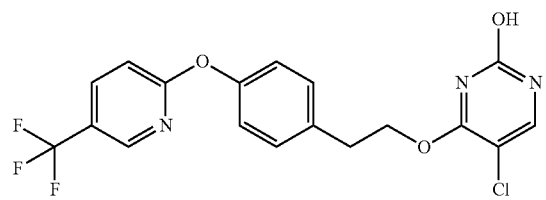 [SMILES: Oc1ncc(Cl)c(OCCc2ccc(Oc3ccc(C(F)(F)F)cn3)cc2)n1]

The title compound was prepared by a procedure similar to that described for D4 starting 2,5-dichloro-4-((4-(3,4-difluorophenoxy)-3-fluorobenzyl)oxy)pyrimidine. LC-MS (ESI): m/z 383 [M+H]$^+$; 3.18 min (ret time).

D108

2,5-dichloro-4-((4-(3,4-difluorophenoxy)-3-fluorobenzyl)oxy)pyrimidine

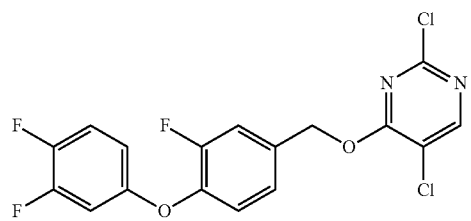 [SMILES: Fc1ccc(Oc2ccc(COc3nc(Cl)ncc3Cl)cc2F)cc1F]

The title compound was prepared by a procedure similar to that described for D3 starting (4-(3,4-difluorophenoxy)-3-fluorophenyl)methanol. LC-MS (ESI): m/z 400 [M+H]$^+$; 4.15 min (ret time).

D109

5-chloro-4-((4-(3,4-difluorophenoxy)-3-fluorobenzyl)oxy)pyrimidin-2(1H)-one

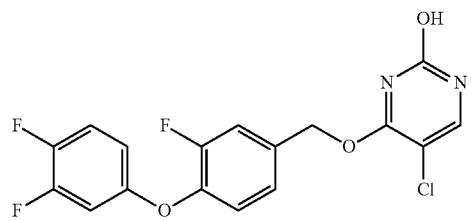 [SMILES: Oc1ncc(Cl)c(OCc2ccc(Oc3ccc(F)c(F)c3)c(F)c2)n1]

The title compound was prepared by a procedure similar to that described for D4 starting 2,5-dichloro-4-((4-(3,4-difluorophenoxy)-3-fluorobenzyl)oxy)pyrimidine. LC-MS (ESI): m/z 383 [M+H]+; 3.18 min (ret time).

D110

2-Chloro-4-(2-(5-(4-chloro-3-(trifluoromethyl)phenoxy)pyridin-2-yl)ethoxy)-5-fluoro pyrimidine

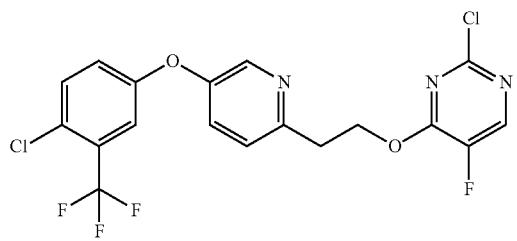

The title compound was prepared by a procedure similar to that described for D3 starting from 2-(5-(4-chloro-3-(trifluoromethyl)phenoxy)pyridin-2-yl)ethanol. LC-MS (ESI): m/z 448 [M+H]+; 3.73 min (ret time).

D111

2-(benzyloxy)-4-(2-(5-(4-Chloro-3-(trifluoromethyl)phenoxy)pyridin-2-yl)ethoxy)-5-fluoropyrimidine

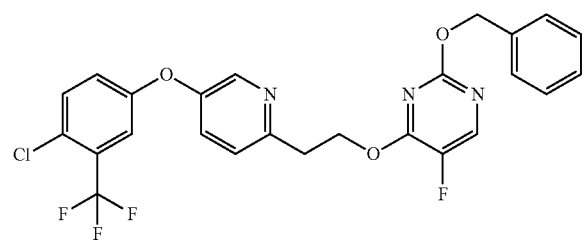

The title compound was prepared by a procedure similar to that described for D63 starting from 2-chloro-4-(2-(5-(4-chloro-3-(trifluoromethyl)phenoxy)pyridin-2-yl)ethoxy)-5-fluoropyrimidine. LC-MS (ESI): m/z 520 [M+H]+; 4.0 min (ret time).

D112

4-(2-(5-(4-chloro-3-(trifluoromethyl)phenoxy)pyridin-2-yl)ethoxy)-5-fluoropyrimidin-2(1H)-one

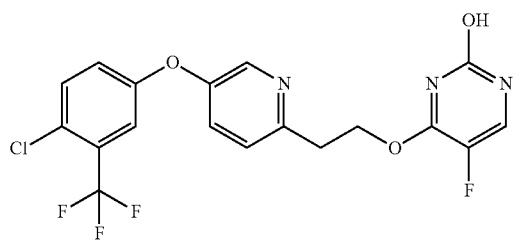 [SMILES: Oc1ncc(F)c(OCCc2ccc(Oc3ccc(Cl)c(C(F)(F)F)c3)cn2)n1]

The title compound was prepared by a procedure similar to that described for D63 starting from 2-(benzyloxy)-4-(2-(5-

(4-chloro-3-(trifluoromethyl)phenoxy)pyridin-2-yl)ethoxy)-5-fluoro pyrimidine, LC-MS (ESI): m/z 430 [M+H]+; 2.77 min (ret time).

D113

2-chloro-5-fluoro-4-(4-((5-(trifluoromethyl)pyridin-2-yl)oxy)phenethoxy)pyrimidine

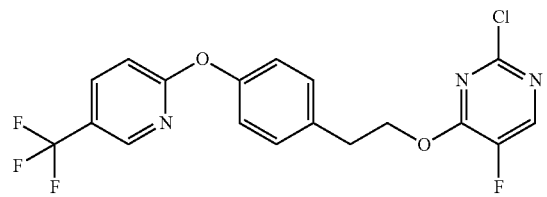 [SMILES: Fc1cnc(Cl)nc1OCCc1ccc(Oc2ccc(C(F)(F)F)cn2)cc1]

The title compound was prepared by a procedure similar to that described for D3 starting from 2-(4-((5-(trifluoromethyl)pyridin-2-yl)oxy)phenyl)ethanol. LC-MS (ESI): m/z 412 [M+H]+; 3.95 min (ret time).

D114

2-(benzyloxy)-5-fluoro-4-(4-((5-(trifluoromethyl)pyridin-2-yl)oxy)phenethoxy)pyrimidine

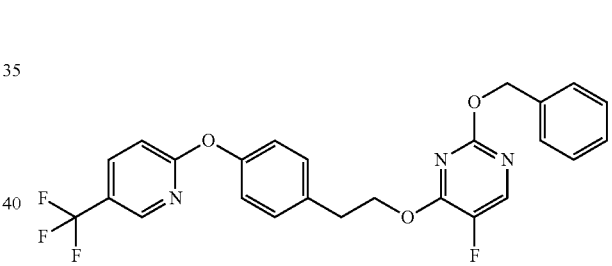

The title compound was prepared by a procedure similar to that described for D63 starting from 2-chloro-5-fluoro-4-(4-((5-(trifluoromethyl)pyridin-2-yl)oxy)phenethoxy)pyrimidine. LC-MS (ESI): m/z 486 [M+H]+; 5.68 min (ret time).

D115

5-fluoro-4-(4-((5-(trifluoromethyl)pyridin-2-yl)oxy)phenethoxy)pyrimidin-2(1H)-one

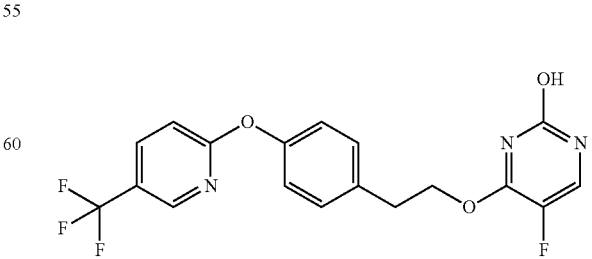

The title compound was prepared by a procedure similar to that described for D64 starting from 2-(benzyloxy)-5-fluoro- 4-(4-((5-(trifluoromethyl)pyridin-2-yl)oxy)phenethoxy)pyrimidine. LC-MS (ESI): m/z 396 [M+H]⁺; 3.02 min (ret time).

D116

4-(3,4-difluorophenoxy)-3-fluorobenzaldehyde

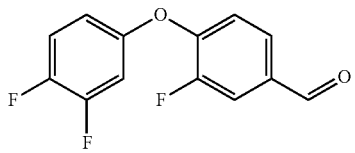 [SMILES: O=Cc1ccc(Oc2ccc(F)c(F)c2)c(F)c1]

The title compound was prepared by a procedure similar to that described for D1 starting from 3,4-difluorobenzaldehyde and 3,4-difluorophenol. LC-MS (ESI): m/z 253 [M+H]⁺; 3.39 min (ret time).

D117

1-(3,4-difluorophenoxy)-2-fluoro-4-vinylbenzene

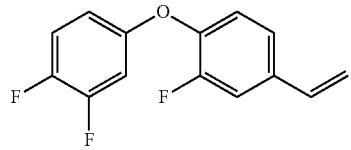 [SMILES: C=Cc1ccc(Oc2ccc(F)c(F)c2)c(F)c1]

The title compound was prepared by a procedure similar to that described for D5 starting from 4-(3,4-difluorophenoxy)-3-fluorobenzaldehyde. LC-MS (ESI): m/z 251 [M+H]⁺; 3.96 min (ret time).

D118

2-(4-(3,4-difluorophenoxy)-3-fluorophenyl)ethanol

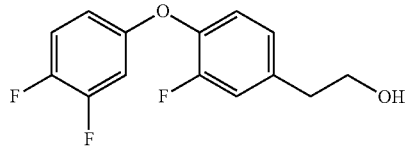 [SMILES: OCCc1ccc(Oc2ccc(F)c(F)c2)c(F)c1]

The title compound was prepared by a procedure similar to that described for D6 starting 1-(3,4-difluorophenoxy)-2-fluoro-4-vinylbenzene. LC-MS (ESI): m/z 268 [M+H]⁺; 3.15 min (ret time).

D119

2-chloro-4-(4-(3,4-difluorophenoxy)-3-fluorophenethoxy)-5-fluoropyrimidine

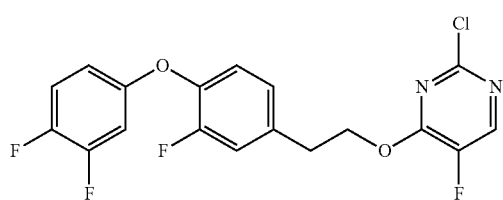 [SMILES: Oc1ncc(F)c(OCCc2ccc(Oc3ccc(F)c(F)c3)c(F)c2)n1]

The title compound was prepared by a procedure similar to that described for D3 starting from 2-(4-(3,4-difluorophenoxy)-3-fluorophenyl)ethanol. LC-MS (ESI): m/z 399 [M+H]⁺; 4.05 min (ret time).

D120

2-(benzyloxy)-4-(4-(3,4-difluorophenoxy)-3-fluorophenethoxy)-5-fluoropyrimidine

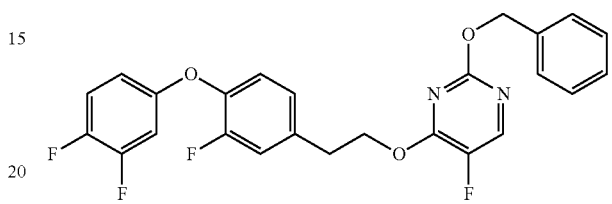

The title compound was prepared by a procedure similar to that described for D63 starting from 2-chloro-4-(4-(3,4-difluorophenoxy)-3-fluorophenethoxy)-5-fluoropyrimidine. LC-MS (ESI): m/z 471 [M+H]⁺; 3.83 min (ret time).

D121

4-(4-(3,4-difluorophenoxy)-3-fluorophenethoxy)-5-fluoropyrimidin-2(1H)-one

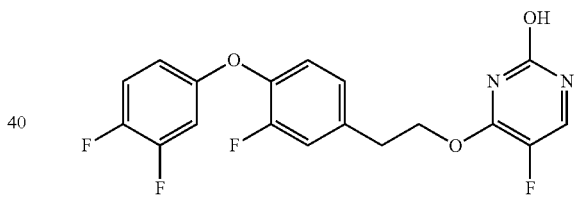

The title compound was prepared by a procedure similar to that described for D64 starting from 2-(benzyloxy)-4-(4-(3,4-difluorophenoxy)-3-fluorophenethoxy)-5-fluoropyrimidine. LC-MS (ESI): m/z 381 [M+H]⁺; 3.14 min (ret time).

D122

3-fluoro-4-((5-(trifluoromethyl)pyridin-2-yl)oxy)benzaldehyde

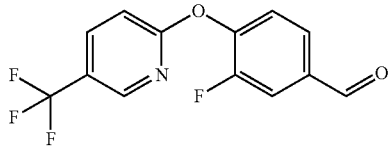 [SMILES: O=Cc1ccc(Oc2ccc(C(F)(F)F)cn2)c(F)c1]

The title compound was prepared by a procedure similar to that described for D1 starting from 3-fluoro-4-hydroxybenzaldehyde and 2-chloro-5-(trifluoromethyl)pyridine, LC-MS (ESI): m/z 286 [M+H]⁺; 3.37 min (ret time).

D123

2-(2-fluoro-4-vinylphenoxy)-5-(trifluoromethyl)
pyridine

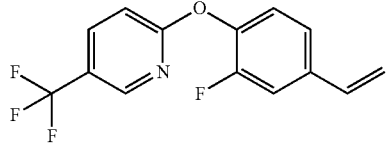 [SMILES: C=Cc1ccc(Oc2ccc(C(F)(F)F)cn2)c(F)c1]

The title compound was prepared by a procedure similar to that described for D5 starting from 3-fluoro-4-((5-(trifluoromethyl)pyridin-2-yl)oxy)benzaldehyde. LC-MS (ESI): m/z 284 [M+H]$^+$; 3.85 min (ret time).

D124

2-(3-fluoro-4-((5-(trifluoromethyl)pyridin-2-yl)oxy)
phenyl)ethanol

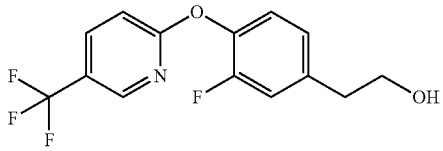 [SMILES: OCCc1ccc(Oc2ccc(C(F)(F)F)cn2)c(F)c1]

The title compound was prepared by a procedure similar to that described for D6 starting 1-(3,4-difluorophenoxy)-2-fluoro-4-vinylbenzene. LC-MS (ESI): m/z 302 [M+H]$^+$; 3.05 min (ret time).

D125

2-chloro-5-fluoro-4-(3-fluoro-4-((5-(trifluoromethyl)
pyridin-2-yl)oxy)phenethoxy)pyrimidine

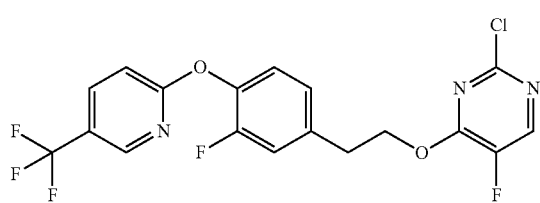 [SMILES: Fc1cc(CCOc2nc(Cl)ncc2F)ccc1Oc1ccc(C(F)(F)F)cn1]

The title compound was prepared by a procedure similar to that described for D3 starting from 2-(3-fluoro-4-((5-(trifluoromethyl)pyridin-2-yl)oxy)phenyl)ethanol. LC-MS (ESI): m/z 432 [M+H]$^+$; 5.03 min (ret time).

D126

2-(benzyloxy)-5-fluoro-4-(3-fluoro-4-((5-(trifluoromethyl)pyridin-2-yl)oxy)phenethoxy)pyrimidine

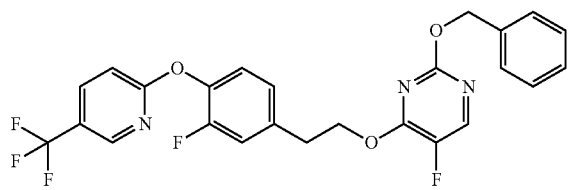 [SMILES: Fc1cc(CCOc2nc(OCc3ccccc3)ncc2F)ccc1Oc1ccc(C(F)(F)F)cn1]

The title compound was prepared by a procedure similar to that described for D63 starting from 2-chloro-4-(4-(3,4-difluorophenoxy)-3-fluorophenethoxy)-5-fluoropyrimidine. LC-MS (ESI): m/z 504 [M+H]$^+$; 5.68 min (ret time).

D127

5-fluoro-4-(3-fluoro-4-((5-(trifluoromethyl)pyridin-2-yl)oxy)phenethoxy)pyrimidin-2(1H)-one

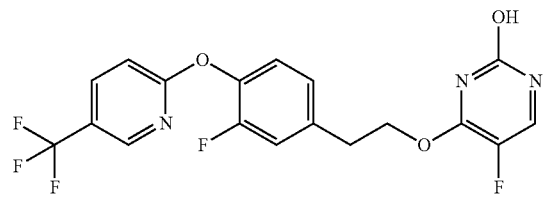 [SMILES: Oc1ncc(F)c(OCCc2ccc(Oc3ccc(C(F)(F)F)cn3)c(F)c2)n1]

The title compound was prepared by a procedure similar to that described for D64 starting from 2-(benzyloxy)-5-fluoro-4-(3-fluoro-4-((5-(trifluoromethyl)pyridin-2-yl)oxy)phenethoxy)pyrimidine. LC-MS (ESI): m/z 414 [M+H]$^+$; 3.07 min (ret time).

D128

2-chloro-5-fluoro-4-(4-methoxyphenethoxy)pyrimidine

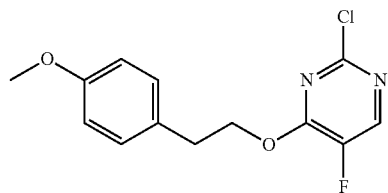 [SMILES: COc1ccc(CCOc2nc(Cl)ncc2F)cc1]

The title compound was prepared by a procedure similar to that described for D3 starting from 2-chloro-5-fluoro-4-(4-methoxyphenethoxy)pyrimidine. LC-MS (ESI): m/z 283 [M+H]$^+$; 3.47 min (ret time).

D129

2-(benzyloxy)-5-fluoro-4-(4-methoxyphenethoxy)
pyrimidine

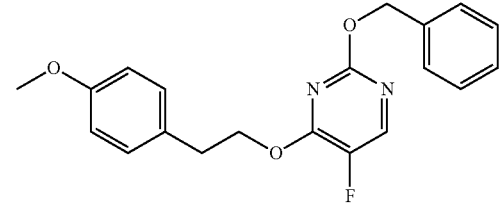 [SMILES: COc1ccc(CCOc2nc(OCc3ccccc3)ncc2F)cc1]

The title compound was prepared by a procedure similar to that described for D63 starting from 2-(4-methoxyphenyl)ethanol. LC-MS (ESI): m/z 355 [M+H]$^+$; 2.85 min (ret time).

D130

5-fluoro-4-(4-methoxyphenethoxy)pyrimidin-2(1H)-one

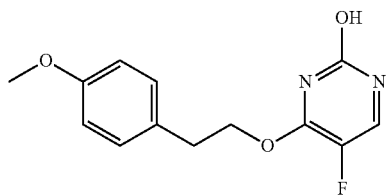 [SMILES: COc1ccc(CCOc2nc(O)ncc2F)cc1]

The title compound was prepared by a procedure similar to that described for D64 starting from 2-(benzyloxy)-5-fluoro-4-(4-methoxyphenethoxy)pyrimidine. LC-MS (ESI): m/z 265 [M+H]$^+$; 2.37 min (ret time).

D131

2-chloro-5-fluoro-4-(4-(trifluoromethoxy)phenethoxy)pyrimidine

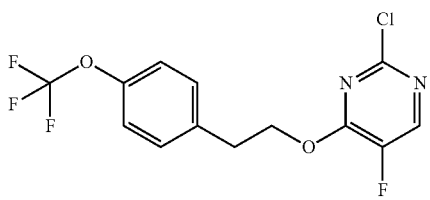 [SMILES: Fc1cnc(Cl)nc1OCCc1ccc(OC(F)(F)F)cc1]

The title compound was prepared by a procedure similar to that described for D3 starting from 2-(4-(trifluoromethoxy)phenyl)ethanol. LC-MS (ESI): m/z 337 [M+H]$^+$; 3.87 min (ret time).

D132

2-(benzyloxy)-5-fluoro-4-(4-(trifluoromethoxy)phenethoxy)pyrimidine

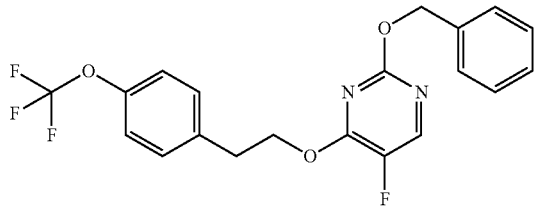 [SMILES: Fc1cnc(OCc2ccccc2)nc1OCCc1ccc(OC(F)(F)F)cc1]

The title compound was prepared by a procedure similar to that described for D63 starting from 2-chloro-5-fluoro-4-(4-(trifluoromethoxy)phenethoxy)pyrimidine. LC-MS (ESI): m/z 409 [M+H]$^+$; 4.19 min (ret time).

D133

5-fluoro-4-(4-(trifluoromethoxy)phenethoxy)pyrimidin-2(1H)-one

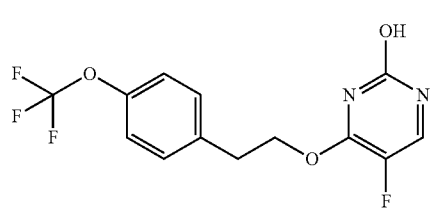 [SMILES: Oc1ncc(F)c(OCCc2ccc(OC(F)(F)F)cc2)n1]

The title compound was prepared by a procedure similar to that described for D64 starting from 2-(benzyloxy)-5-fluoro-4-(4-(trifluoromethoxy)phenethoxy)pyrimidine. LC-MS (ESI); m/z 319 [M+H]$^+$; 3.49 min (ret time).

D134

2-chloro-5-fluoro-4-(4-fluorophenethoxy)pyrimidine

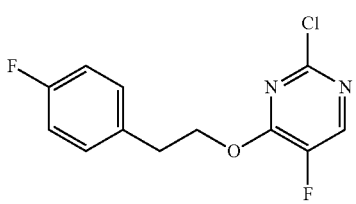 [SMILES: Fc1ccc(CCOc2nc(Cl)ncc2F)cc1]

The title compound was prepared by a procedure similar to that described for D3 starting from 2-(4-fluorophenyl)ethanol. LC-MS (ESI): m/z 271 [M+H]$^+$; 3.54 min (ret time).

D135

2-(benzyloxy)-5-fluoro-4-(4-fluorophenethoxy)pyrimidine

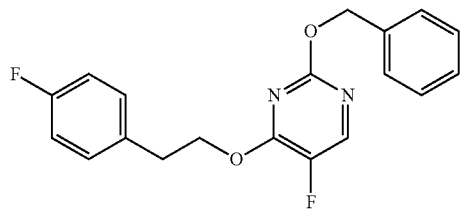 [SMILES: Fc1ccc(CCOc2nc(OCc3ccccc3)ncc2F)cc1]

The title compound was prepared by a procedure similar to that described for D63 starting from 2-chloro-5-fluoro-4-(4-fluorophenethoxy)pyrimidine. LC-MS (ESI): m/z 343 [M+H]$^+$; 3.95 min (ret time).

D136

5-fluoro-4-(4-fluorophenethoxy)pyrimidin-2(1H)-one

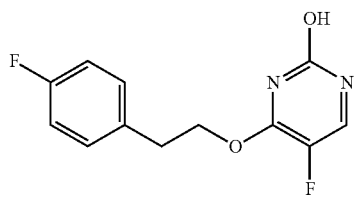 [SMILES: Oc1ncc(F)c(OCCc2ccc(F)cc2)n1]

The title compound was prepared by a procedure similar to that described for D64 starting from 2-chloro-5-fluoro-4-(4-fluorophenethoxy)pyrimidine. LC-MS (ESI): m/z 253 [M+H]$^+$; 2.98 min (ret time).

D137

2-(4-((6-methylpyridin-2-yl)oxy)phenyl)ethanol

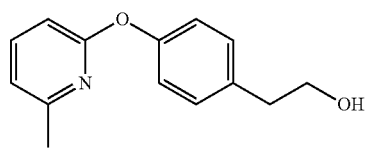 [SMILES: Cc1cccc(Oc2ccc(CCO)cc2)n1]

The title compound was prepared by a procedure similar to that described for D1 starting from 4-(2-hydroxyethyl)phenol and 2-chloro-6-methylpyridine. LC-MS (ESI): m/z 230 [M+H]$^+$; 3.08 min (ret time).

D138

2-Chloro-5-fluoro-4-(4-((6-methylpyridin-2-yl)oxy)phenethoxy)pyrimidine

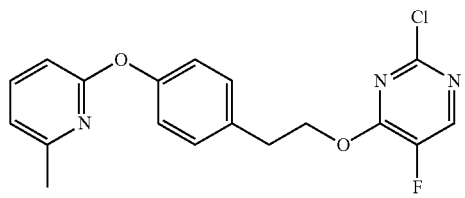 [SMILES: Cc1cccc(Oc2ccc(CCOc3nc(Cl)ncc3F)cc2)n1]

The title compound was prepared by a procedure similar to that described for D3 starting from 2-(4-((6-methylpyridin-2-yl)oxy)phenyl)ethanol. LC-MS (ESI): m/z 360 [M+H]$^+$; 3.51 min (ret time).

D139

2-(benzyloxy)-5-fluoro-4-(4-((6-methylpyridin-2-yl)oxy)phenethoxy)pyrimidine

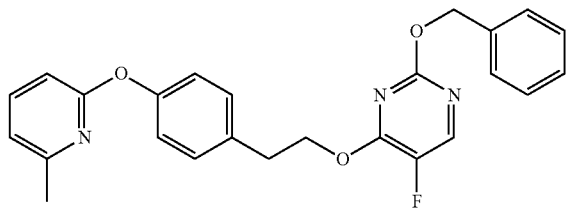 [SMILES: Cc1cccc(Oc2ccc(CCOc3nc(OCc4ccccc4)ncc3F)cc2)n1]

The title compound was prepared by a procedure similar to that described for D63 starting from 2-chloro-5-fluoro-4-(4-fluorophenethoxy)pyrimidine. LC-MS (ESI): m/z 432 [M+H]$^+$; 3.89 min (ret time).

D140

5-fluoro-4-(4-((6-methylpyridin-2-yl)oxy)phenethoxy)pyrimidin-2(1H)-one

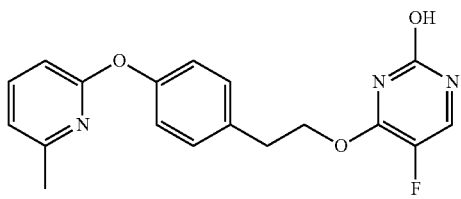 [SMILES: Cc1cccc(Oc2ccc(CCOc3nc(O)ncc3F)cc2)n1]

The title compound was prepared by a procedure similar to that described for D64 starting from 2-(benzyloxy)-5-fluoro-4-(4-((6-methylpyridin-2-yl)oxy)phenethoxy)pyrimidine. LC-MS (ESI): m/z 342 [M+H]$^+$; 3.26 min (ret time).

D141

2-chloro-5-fluoro-4-(4-(trifluoromethyl)phenethoxy)pyrimidine

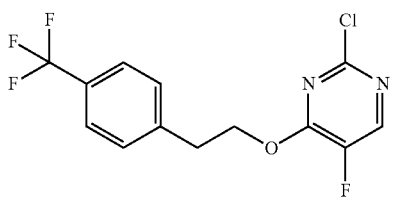 [SMILES: Fc1cnc(Cl)nc1OCCc1ccc(C(F)(F)F)cc1]

The title compound was prepared by a procedure similar to that described for D3 starting from 2-(4-(trifluoromethyl)phenyl)ethanol. LC-MS (ESI): m/z 321 [M+H]$^+$; 3.21 min (ret time).

D142

2-(benzyloxy)-5-fluoro-4-(4-(trifluoromethyl)phenethoxy)pyrimidine

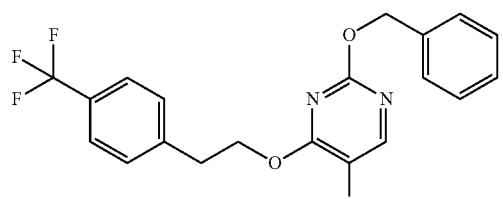

The title compound was prepared by a procedure similar to that described for D63 starting from 2-chloro-5-fluoro-4-(4-(trifluoromethyl)phenethoxy)pyrimidine. LC-MS (ESI): m/z 393 [M+H]$^+$; 4.11 min (ret time).

D143

5-fluoro-4-(4-(trifluoromethyl)phenethoxy)pyrimidin-2(1H)-one

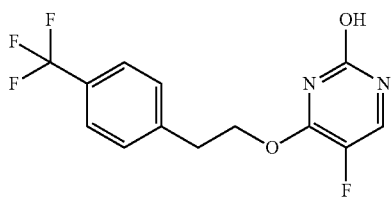 [SMILES: Oc1ncc(F)c(OCCc2ccc(C(F)(F)F)cc2)n1]

The title compound was prepared by a procedure similar to that described for D64 starting from 2-chloro-5-fluoro-4-(4-(trifluoromethyl)phenethoxy)pyrimidine, LC-MS (ESI): m/z 303 [M+H]$^+$; 2.77 min (ret time).

D144

2-(4-((6-(trifluoromethyl)pyridin-2-yl)oxy)phenyl)ethanol

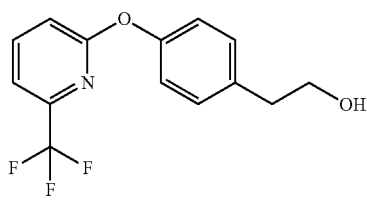 [SMILES: OCCc1ccc(Oc2cccc(C(F)(F)F)n2)cc1]

The title compound was prepared by a procedure similar to that described for D1 starting from 4-(2-hydroxyethyl)phenol and 2-chloro-6-(trifluoromethyl)pyridine, LC-MS (ESI): m/z 284 [M+H]$^+$; 3.00 min (ret time).

D145

2-chloro-5-fluoro-4-(4-((6-(trifluoromethyl)pyridin-2-yl)oxy)phenethoxy)pyrimidine

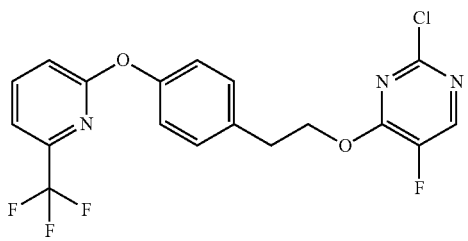 [SMILES: Fc1cnc(Cl)nc1OCCc1ccc(Oc2cccc(C(F)(F)F)n2)cc1]

The title compound was prepared by a procedure similar to that described for D3 starting from 2-(4-((6-(trifluoromethyl)pyridin-2-yl)oxy)phenyl)ethanol. LC-MS (ESI): m/z 414 [M+H]$^+$; 3.93 min (ret time).

D146

2-(benzyloxy)-5-fluoro-4-(4-((6-(trifluoromethyl)pyridin-2-yl)oxy)phenethoxy)pyrimidine

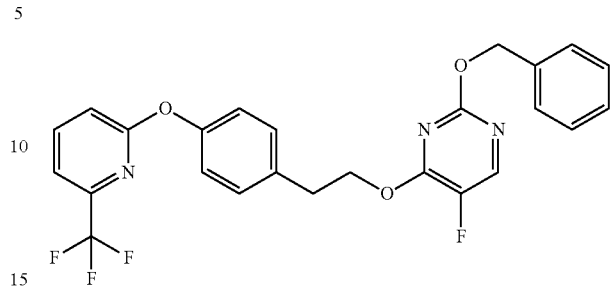

The title compound was prepared by a procedure similar to that described for D63 starting from 2-chloro-5-fluoro-4-(4-((6-(trifluoromethyl)pyridin-2-yl)oxy)phenethoxy)pyrimidine. LC-MS (ESI): m/z 486 [M+H]$^+$; 3.21 min (ret time).

D147

5-fluoro-4-(4-((6-(trifluoromethyl)pyridin-2-yl)oxy)phenethoxy)pyrimidin-2(1H)-one

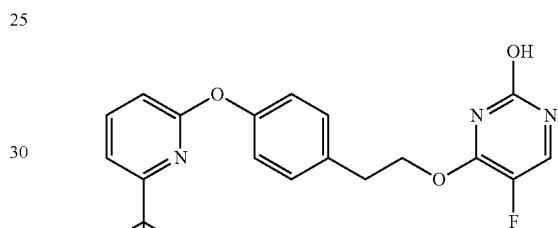

The title compound was prepared by a procedure similar to that described for D64 starting from 2-(benzyloxy)-5-fluoro-4-(4-((6-(trifluoromethyl)pyridin-2-yl)oxy)phenethoxy)pyrimidine. LC-MS (ESI): m/z 396 [M+H]$^+$; 3.01 min (ret time).

D148

(2-methoxypyrimidin-5-yl)methanol

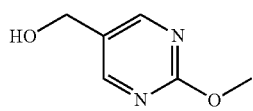

The title compound was prepared by a procedure similar to that described for D59 starting 2-methoxypyrimidine-5-carbaldehyde

D149

5-(chloromethyl)-2-methoxypyrimidine

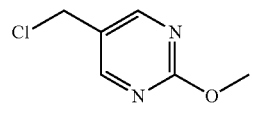

The title compound was prepared by a procedure similar to that described for D60 starting (2-from methoxypyrimidin-5-yl)methanol.

D150

2-Chloro-4-(4-(4-chloro-3-(trifluoromethyl)phenoxy)phenethoxy)-5-methylpyrimidine

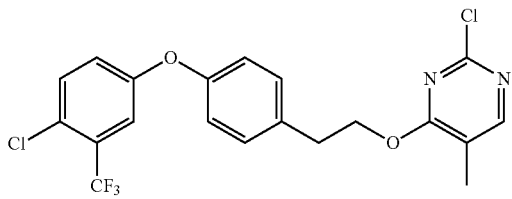 [SMILES: Cc1cnc(Cl)nc1OCCc1ccc(Oc2ccc(Cl)c(C(F)(F)F)c2)cc1]

The title compound was prepared by a procedure similar to that described for D3 starting from 2-(4-(4-chloro-3-(trifluoromethyl)phenoxy)phenyl)ethanol. LC-MS (ESI): m/z 443 [M+H]$^+$; 4.49 min (ret time).

D151

4-(4-(4-chloro-3-(trifluoromethyl)phenoxy)phenethoxy)-5-methylpyrimidin-2(1H)-one

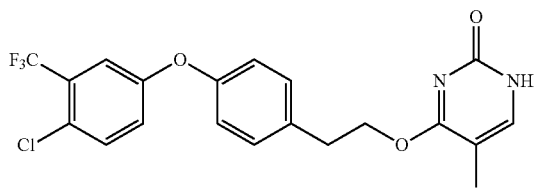 [SMILES: Cc1c[nH]c(=O)nc1OCCc1ccc(Oc2ccc(Cl)c(C(F)(F)F)c2)cc1]

The title compound was prepared by a procedure similar to that described for D4 starting from 2-chloro-4-(4-(4-chloro-3-(trifluoromethyl)phenoxy)phenethoxy)-5-methylpyrimidine. LC-MS (ESI): m/z 425 [M+H]$^+$; 3.61 min (ret time).

D152

2-chloro-4-(2-(6-(3,4-difluorophenoxy)pyridin-3-yl)ethoxy)-5-methylpyrimidine

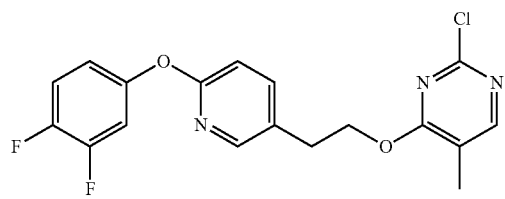 [SMILES: Cc1cnc(Cl)nc1OCCc1ccc(Oc2ccc(F)c(F)c2)nc1]

The title compound was prepared by a procedure similar to that described for D3 starting from 2-(6-(3,4-difluorophenoxy)pyridin-3-yl)ethanol. LC-MS (ESI): m/z 378 [M+H]$^+$; 3.74 min (ret time).

D153

4-(2-(6-(3,4-difluorophenoxy)pyridin-3-yl)ethoxy)-5-methylpyrimidin-2-ol

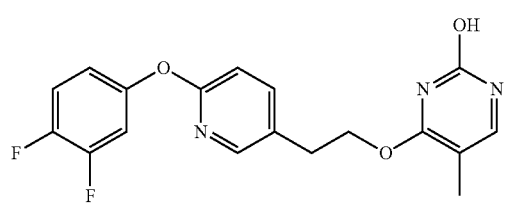 [SMILES: Cc1cnc(O)nc1OCCc1ccc(Oc2ccc(F)c(F)c2)nc1]

The title compound was prepared by a procedure similar to that described for D4 starting from 2-chloro-4-(2-(6-(3,4-difluorophenoxy)pyridin-3-yl)ethoxy)-5-methylpyrimidine. LC-MS (ESI): m/z 360 [M+H]$^+$; 2.77 min (ret time).

D154

1-phenoxy-4-vinylbenzene

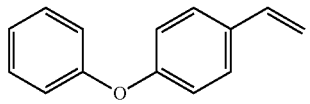

The title compound was prepared by a procedure similar to that described for D5 starting from 4-phenoxybenzaldehyde. LC-MS (ESI): m/z 197 [M+H]$^+$; 3.89 min (ret time).

D155

2-(4-phenoxyphenyl)ethanol

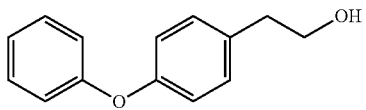 [SMILES: OCCc1ccc(Oc2ccccc2)cc1]

The title compound was prepared by a procedure similar to that described for D6 starting from 1-phenoxy-4-vinylbenzene. LC-MS (ESI): m/z 215 [M+H]$^+$; 2.97 min (ret time).

D156

2-chloro-5-fluoro-4-(4-phenoxyphenethoxy)pyrimidine

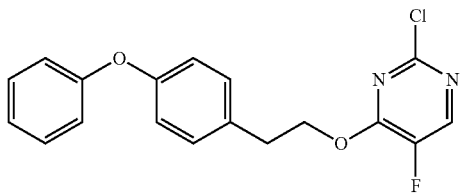 [SMILES: Fc1cnc(Cl)nc1OCCc1ccc(Oc2ccccc2)cc1]

The title compound was prepared by a procedure similar to that described for D3 starting from 2-(4-phenoxyphenyl)ethanol. LC-MS (ESI): m/z 345 [M+H]$^+$; 4.05 min (ret time).

D157

2-(benzyloxy)-5-fluoro-4-(4-phenoxyphenethoxy)pyrimidine

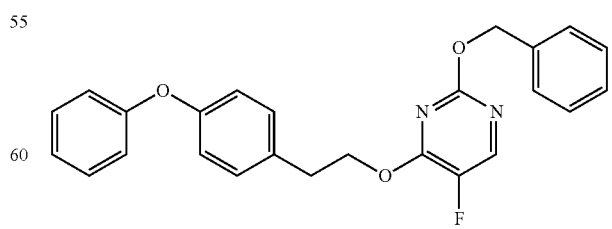

The title compound was prepared by a procedure similar to that described for D63 starting from 2-chloro-5-fluoro-4-(4-phenoxyphenethoxy)pyrimidine. LC-MS (ESI): m/z 417 [M+H]$^+$; 4.32 min (ret time).

D158

5-fluoro-4-(4-phenoxyphenethoxy)pyrimidin-2-ol

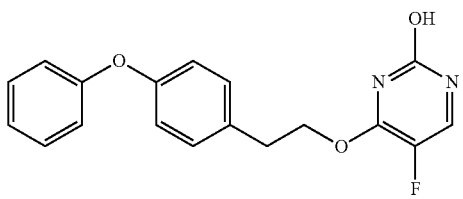 [SMILES: Oc1ncc(F)c(OCCc2ccc(Oc3ccccc3)cc2)n1]

The title compound was prepared by a procedure similar to that described for D63 starting from 2-(benzyloxy)-5-fluoro-4-(4-phenoxyphenethoxy)pyrimidine. LC-MS (ESI): m/z 327 [M+H]$^+$; 3.01 min (ret time).

D160

5-(((2-chloro-5-methylpyrimidin-4-yl)oxy)methyl)-2-(3-(trifluoromethyl)phenoxy)benzonitrile

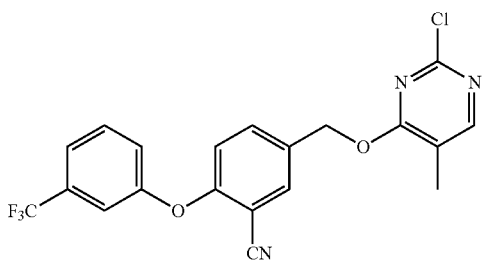 [SMILES: Cc1cnc(Cl)nc1OCc1ccc(Oc2cccc(C(F)(F)F)c2)c(C#N)c1]

The title compound was prepared by a procedure similar to that described for D3 starting from 5-(hydroxymethyl)-2-(3-(trifluoromethyl)phenoxy)benzonitrile. LC-MS (ESI): m/z 420 [M+H]$^+$; 3.74 min (ret time).

D161

5-(((5-methyl-2-oxo-1,2-dihydropyrimidin-4-yl)oxy)methyl)-2-(3-(trifluoromethyl)phenoxy)benzonitrile

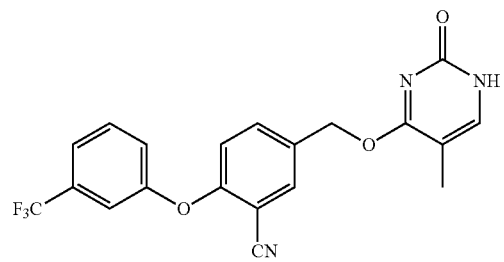 [SMILES: Cc1c[nH]c(=O)nc1OCc1ccc(Oc2cccc(C(F)(F)F)c2)c(C#N)c1]

The title compound was prepared by a procedure similar to that described for D4 starting from 5-(((2-chloro-5-methylpyrimidin-4-yl)oxy)methyl)-2-(3-(trifluoromethyl)phenoxy)benzonitrile. LC-MS (ESI): m/z 402 [M+H]$^+$; 3.10 min (ret time).

D162

2-chloro-4-((4-(3,4-difluorophenoxy)-3-fluorobenzyl)oxy)-5-methylpyrimidine

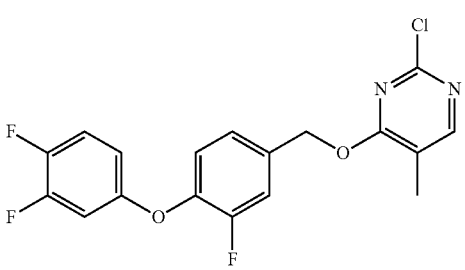 [SMILES: Cc1cnc(Cl)nc1OCc1ccc(Oc2ccc(F)c(F)c2)c(F)c1]

The title compound was prepared by a procedure similar to that described for D3 starting from (4-(3,4-difluorophenoxy)-3-fluorophenyl)methanol. LC-MS (ESI): m/z 381 [M+H]$^+$; 4.05 min (ret time).

D163

4-((4-(3,4-difluorophenoxy)-3-fluorobenzyl)oxy)-5-methylpyrimidin-2(1H)-one

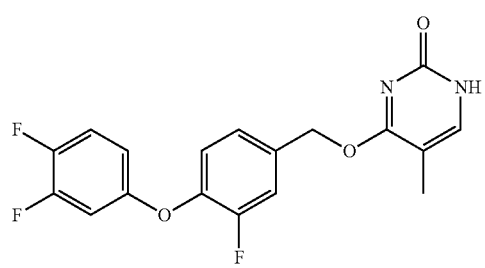 [SMILES: Cc1c[nH]c(=O)nc1OCc1ccc(Oc2ccc(F)c(F)c2)c(F)c1]

The title compound was prepared by a procedure similar to that described for D4 starting from 2-chloro-4-((4-(3,4-difluorophenoxy)-3-fluorobenzyl)oxy)-5-methylpyrimidine. LC-MS (ESI): m/z 363 [M+H]$^+$; 3.12 min (ret time).

D164

5-(((2-chloro-5-methylpyrimidin-4-yl)oxy)methyl)-2-(3,4-difluorophenoxy)benzonitrile

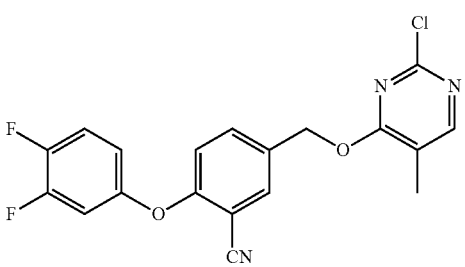

The title compound was prepared by a procedure similar to that described for D3 starting from 2-(3,4-difluorophenoxy)-5-(hydroxymethyl)benzonitrile. LC-MS (ESI): m/z 388 [M+H]$^+$; 3.81 min (ret time).

D165

2-(3,4-difluorophenoxy)-5-(((5-methyl-2-oxo-1,2-dihydropyrimidin-4-yl)oxy)methyl)benzonitrile

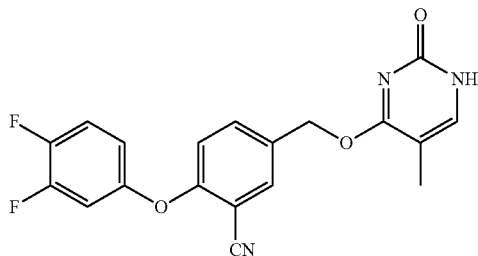 [SMILES: Cc1c[nH]c(=O)nc1OCc1ccc(Oc2ccc(F)c(F)c2)c(C#N)c1]

The title compound was prepared by a procedure similar to that described for D4 starting from 5-(((2-chloro-5-methylpyrimidin-4-yl)oxy)methyl)-2-(3,4-difluorophenoxy)benzonitrile. LC-MS (ESI): m/z 370 [M+H]$^+$; 2.93 min (ret time).

E1

2-{[4-Chloro-3-(trifluoromethyl)phenyl]oxy}-5-({[2-oxo-1-(3-pyridinylmethyl)-1,2-dihydro-4-pyrimidinyl]oxy}methyl)benzonitrile

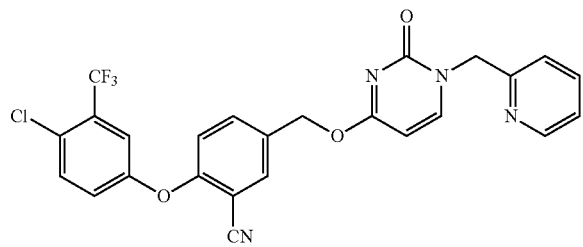 [SMILES: N#Cc1cc(COc2ccn(Cc3ccccn3)c(=O)n2)ccc1Oc1ccc(Cl)c(C(F)(F)F)c1]

A mixture of 2-{[4-chloro-3-(trifluoromethyl)phenyl]oxy}-5-{[(2-oxo-2,3-dihydro-4-pyrimidinyl)oxy]methyl}benzonitrile (100 mg, 0.237 mmol), 2-(chloromethyl)pyridine hydrochloride (58.3 mg, 0.356 mmol) and Cs$_2$CO$_3$ (464 mg, 1.42 mmol) in anhydrous N,N-dimethylformamide (10 mL) was sealed in a microwave vial, then irradiated with a microwave at 110° C. for 2 h and filtered. Purification via mass-directed autopreparation afforded the title product (10 mg). LC-MS (ESI): m/z 513 [M+H]$^+$; 4.12 min (ret time).

E2

2-{[4-Chloro-3-(trifluoromethyl)phenyl]oxy}-5-({[2-oxo-1-(4-pyridinylmethyl)-1,2-dihydro-4-pyrimidinyl]oxy}methyl)benzonitrile trifluoroacetate

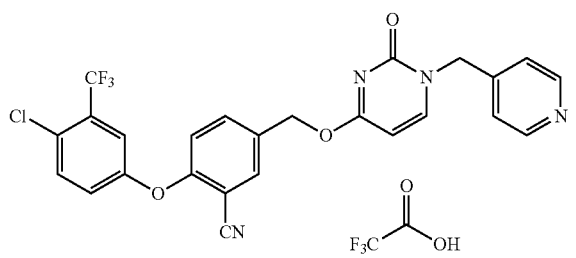

The title compound was prepared by a procedure similar to that described for E1 starting with 2-{[4-chloro-3-(trifluoromethyl)phenyl]oxy}-5-{[(2-oxo-2,3-dihydro-4-pyrimidinyl)oxy]methyl}benzonitrile and 4-(chloromethyl)pyridine hydrochloride. LC-MS (ESI): m/z 513 [M+H]$^+$; 2.8 min (ret time).

E3

2-(4-Chloro-3-(trifluoromethyl)phenoxy)-5-(((2-oxo-2,3-dihydropyrimidin-4-yl)oxy) methyl)benzonitrile

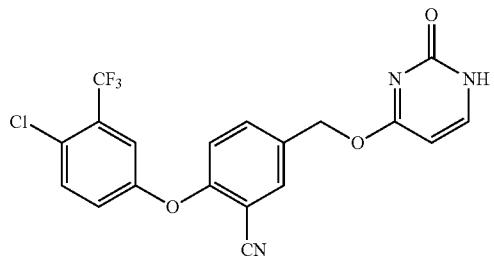 [SMILES: N#Cc1cc(COc2cc[nH]c(=O)n2)ccc1Oc1ccc(Cl)c(C(F)(F)F)c1]

The title compound was prepared by a procedure similar to that described for E1 starting with 5-{[(2-Chloro-4-pyrimidinyl)oxy]methyl}-2-{[4-chloro-3-(trifluoromethyl)phenyl]oxy}benzonitrile. LC-MS (ESI): m/z 420 [M−H]$^+$; 3.89 min (ret time).

E4

2-(4-Chloro-3-(trifluoromethyl)phenoxy)-5-(((2-oxo-1-(pyridin-3-ylmethyl)-1,2-dihydropyrimidin-4-yl)oxy)methyl)benzonitrile

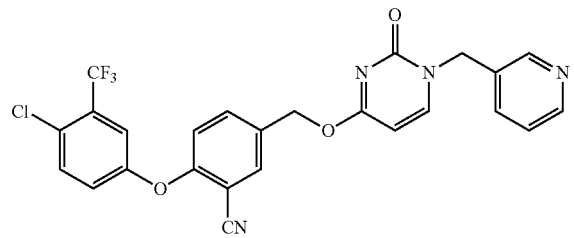 [SMILES: N#Cc1cc(COc2ccn(Cc3cccnc3)c(=O)n2)ccc1Oc1ccc(Cl)c(C(F)(F)F)c1]

The title compound was prepared by a procedure similar to that described for E1 starting from 2-{[4-chloro-3-(trifluoromethyl)phenyl]oxy}-5-{[(2-oxo-2,3-dihydro-4-pyrimidinyl)oxy]methyl}benzonitrile and 3-(chloromethyl)pyridine hydrochloride. LC-MS (ESI): m/z 513 [M+H]$^+$; 2.94 min (ret time).

E5

2-{[4-Chloro-3-(trifluoromethyl)phenyl]oxy}-5-{[(1-ethyl-2-oxo-1,2-dihydro-4-pyrimidinyl)oxy]methyl}benzonitrile

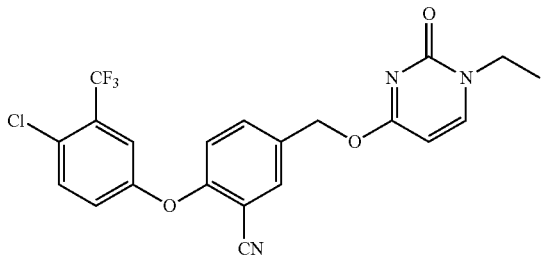 [SMILES: CCn1ccc(OCc2ccc(Oc3ccc(Cl)c(C(F)(F)F)c3)c(C#N)c2)nc1=O]

The title compound was prepared by a procedure similar to that described for E1 starting from 2-{[4-chloro-3-(trifluoromethyl)phenyl]oxy}-5-{[(2-oxo-2,3-dihydro-4-pyrimidinyl)oxy]methyl}benzonitrile and bromoethane. LC-MS (ESI): m/z 450 [M+H]⁺; 4.11 min (ret time).

E6

2-{[4-Chloro-3-(trifluoromethyl)phenyl]oxy}-5-[({1-[(1-methyl-1H-pyrazol-4-yl)methyl]-2-oxo-1,2-dihydro-4-pyrimidinyl}oxy)methyl]benzonitrile

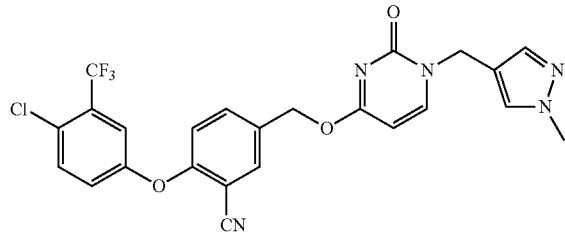 [SMILES: Cn1cc(Cn2ccc(OCc3ccc(Oc4ccc(Cl)c(C(F)(F)F)c4)c(C#N)c3)nc2=O)cn1]

The title compound was prepared by a procedure similar to that described for E1 starting from 2-{[4-chloro-3-(trifluoromethyl)phenyl]oxy}-5-{[(2-oxo-1,2-dihydro-4-pyrimidinyl)oxy]methyl}benzonitrile and 4-(chloromethyl)-1-methyl-1H-pyrazole hydrochloride. LC-MS (ESI): m/z 514 [M+H]⁺; 3.97 min (ret time).

E7

2-{[4-Chloro-3-(trifluoromethyl)phenyl]oxy}-5-(2-{[2-oxo-1-(3-pyridinylmethyl)-1,2-dihydro-4-pyrimidinyl]oxy}ethyl)benzonitrile trifluoroacetate

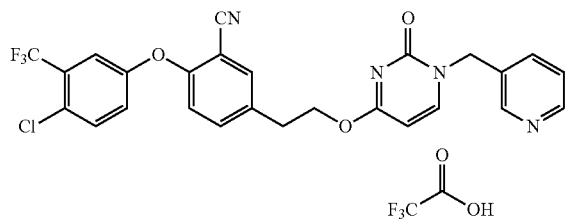

The title compound was prepared by a procedure similar to that described for E1 starting from 2-{[4-chloro-3-(trifluoromethyl)phenyl]oxy}-5-{2-[(2-oxo-2,3-dihydro-4-pyrimidinyl)oxy]ethyl}benzonitrile and 3-(chloromethyl)pyridine. LC-MS (ESI): m/z 527 [M+H]⁺; 2.94 min (ret time).

E8

4-{[(4-{[4-Chloro-3-(trifluoromethyl)phenyl]oxy}phenyl)methyl]oxy}-1-[(1-methyl-1H-pyrazol-4-yl)methyl]-2(1H)-pyrimidinone

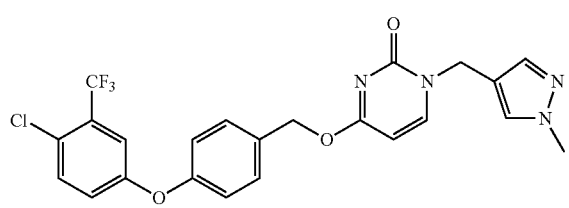 [SMILES: Cn1cc(Cn2ccc(OCc3ccc(Oc4ccc(Cl)c(C(F)(F)F)c4)cc3)nc2=O)cn1]

The title compound was prepared by a procedure similar to that described for E1 starting from 4-{[(4-{[4-chloro-3-(trifluoromethyl)phenyl]oxy}phenyl)methyl]oxy}-2(1H)-pyrimidinone and 4-(chloromethyl)-1-methyl-1H-pyrazole hydrochloride. LC-MS (ESI): m/z 491 [M+H]⁺; 3.49 min (ret time).

E9

4-{[2-(4-{[4-Chloro-3-(trifluoromethyl)phenyl]oxy}phenyl)ethyl]oxy}-1-(4-pyridinyl methyl)-2(1H)-pyrimidinone

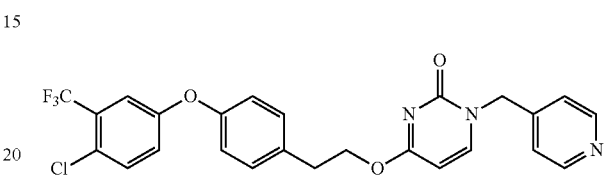

The title compound was prepared by a procedure similar to that described for E1 starting from 4-{[2-(4-{[4-chloro-3-(trifluoromethyl)phenyl]oxy}phenyl)ethyl]oxy}-2(1H)-pyrimidinone and 4-(chloromethyl)pyridine hydrochloride. LC-MS (ESI): m/z 502 [M+H]⁺; 4.27 min (ret time).

E10

4-{[2-(4-{[4-Chloro-3-(trifluoromethyl)phenyl]oxy}phenyl)ethyl]oxy}-1-(3-pyridinylmethyl)-2(1H)-pyrimidinone

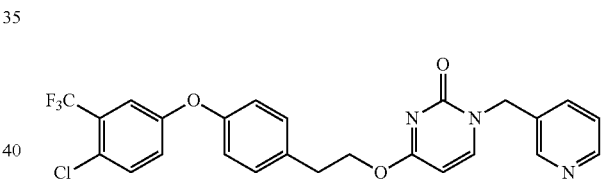

The title compound was prepared by a procedure similar to that described for E1 starting from 4-{[2-(4-{[4-chloro-3-(trifluoromethyl)phenyl]oxy}phenyl)ethyl]oxy}-2(1H)-pyrimidinone and 3-(chloromethyl)pyridine hydrochloride. LC-MS (ESI): m/z 502 [M+H]⁺; 4.30 min (ret time).

E11

4-{[2-(4-{[4-Chloro-3-(trifluoromethyl)phenyl]oxy}phenyl)ethyl]oxy}-1-(5-pyrimidinyl methyl)-2(1H)-pyrimidinone

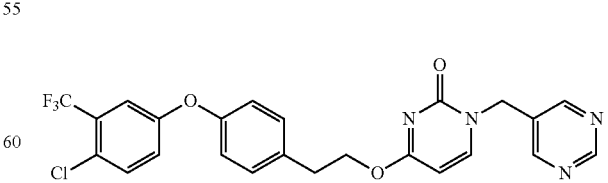

The title compound was prepared by a procedure similar to that described for E1 starting from 4-{[2-(4-{[4-chloro-3-(trifluoromethyl)phenyl]oxy}phenyl)ethyl]oxy}-2(1H)-pyrimidinone and 5-(bromomethyl)pyrimidine. LC-MS (ESI): m/z 503 [M+H]⁺; 3.55 min (ret time).

E12

4-{[2-(4-{[4-Chloro-3-(trifluoromethyl)phenyl]oxy}phenyl)ethyl]oxy}-1-[(1-methyl-1H-pyrazol-4-yl)methyl]-2(1H)-pyrimidinone

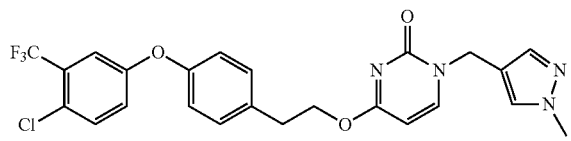 [SMILES: Cn1cc(Cn2ccc(OCCc3ccc(Oc4ccc(Cl)c(C(F)(F)F)c4)cc3)nc2=O)cn1]

The title compound was prepared by a procedure similar to that described for E1 starting with 4-{[2-(4-{[4-chloro-3-(trifluoromethyl)phenyl]oxy}phenyl)ethyl]oxy}-2(1H)-pyrimidinone and 4-(chloromethyl)-1-methyl-1H-pyrazole hydrochloride. LC-MS (ESI): m/z 505 [M+H]$^+$; 4.28 min (ret time).

E13

4-{[2-(4-{[4-Chloro-3-(trifluoromethyl)phenyl]oxy}phenyl)ethyl]oxy}-1-[2-(3-pyridinyl)ethyl]-2(1H)-pyrimidinone trifluoroacetate

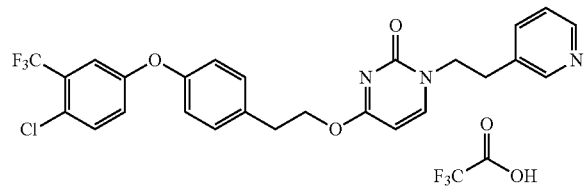

The title compound was prepared by a procedure similar to that described for E1 starting from 4-{[2-(4-{[4-chloro-3-(trifluoromethyl)phenyl]oxy}phenyl)ethyl]oxy}-2(1H)-pyrimidinone and 3-(2-chloroethyl)pyridine hydrochloride. LC-MS (ESI): m/z 515 [M+H]$^+$; 4.33 min (ret time).

E14

4{[(5-{[4-Chloro-3-(trifluoromethyl)phenyl]oxy}-2-pyridinyl)methyl]oxy}-1-(3-pyridinylmethyl)-2(1H)-pyrimidinone

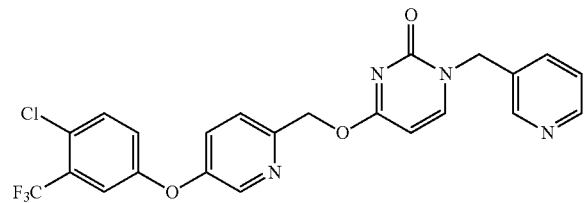 [SMILES: O=c1nc(OCc2ccc(Oc3ccc(Cl)c(C(F)(F)F)c3)cn2)ccn1Cc1cccnc1]

The title compound was prepared by a procedure similar to that described for E1 starting from 6-{[(5-{[4-chloro-3-(trifluoromethyl)phenyl]oxy}-2-pyridinyl)methyl]oxy}-2(1H)-pyrimidinone and 3-(chloromethyl)pyridine hydrochloride. LC-MS (ESI): m/z 489 [M+H]$^+$; 2.67 min (ret time).

E15

4-{[(5-{[4-Chloro-3-(trifluoromethyl)phenyl]oxy}-2-pyridinyl)methyl]oxy}-1-[(1-methyl-1H-pyrazol-4-yl)methyl]-2(1H)-pyrimidinone

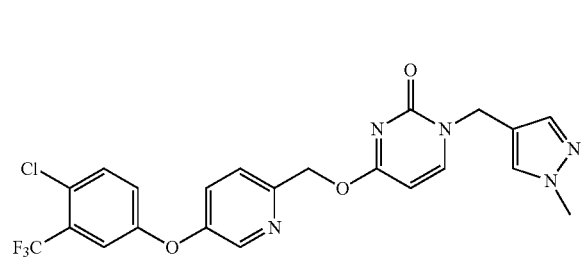 [SMILES: Cn1cc(Cn2ccc(OCc3ccc(Oc4ccc(Cl)c(C(F)(F)F)c4)cn3)nc2=O)cn1]

The title compound was prepared by a procedure similar to that described for E1 starting from 4-{[(5-{[4-chloro-3-(trifluoromethyl)phenyl]oxy}-2-pyridinyl)methyl]oxy}-2(1H)-pyrimidinone and 4-(Chloromethyl)-1-methyl-1H-pyrazole hydrochloride. LC-MS (ESI): m/z 492 [M+H]$^+$; 3.79 min (ret time).

E16

4-{[2-(5-{[4-Chloro-3-(trifluoromethyl)phenyl]oxy}-2-pyridinyl)ethyl]oxy}-1-[(1-methyl-1H-pyrazol-4-yl)methyl]-2(1H)-pyrimidinone

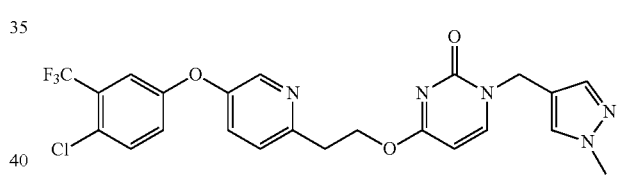

The title compound was prepared by a procedure similar to that described for E1 starting from 6-{[2-(5-{[4-chloro-3-(trifluoromethyl)phenyl]oxy}-2-pyridinyl)ethyl]oxy}-2(1H)-pyrimidinone and 4-(chloromethyl)-1-methyl-1H-pyrazole hydrochloride. LC-MS (ESI): m/z 506 [M+H]$^+$; 2.90 min (ret time).

E17

4-{[(6-{[4-Chloro-3-(trifluoromethyl)phenyl]oxy}-5-fluoro-3-pyridinyl)methyl]oxy}-1-[(1-methyl-1H-pyrazol-4-yl)methyl]-2 (1H)-pyrimidinone

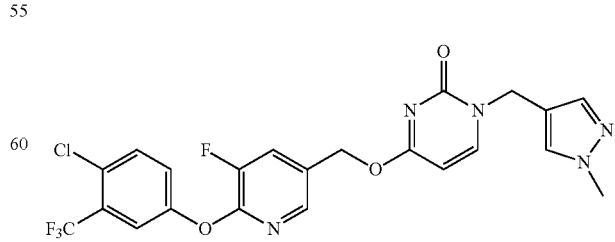

The title compound was prepared by a procedure similar to that described for E1 starting from 6-{[2-(5-{[4-chloro-3-(trifluoromethyl)phenyl]oxy}-2-pyridinyl)ethyl]oxy}-2

E18

4-{[2-(6-{[4-Chloro-3-(trifluoromethyl)phenyl]oxy}-5-fluoro-3-pyridinyl)ethyl]oxy}-1-[(1-methyl-1H-pyrazol-4-yl)methyl]-2(1H)-pyrimidinone

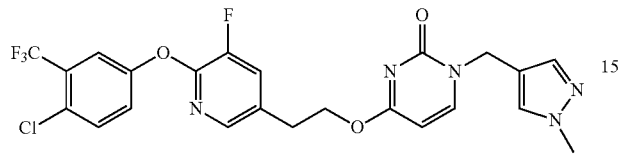

The title compound was prepared by a procedure similar to that described for E1 starting from 6-{[2-(6-{[4-chloro-3-(trifluoromethyl)phenyl]oxy}-5-fluoro-3-pyridinyl)ethyl]oxy}-2 (1H)-pyrimidinone and 4-(chloromethyl)-1-methyl-1H-pyrazole hydrochloride. LC-MS (ESI): m/z 524 [M+H]$^+$; 3.36 min (ret time).

E19

2-{[4-Chloro-3-(trifluoromethyl)phenyl]oxy}-5-({[2-oxo-1-(3-pyridinylmethyl)-1,2-dihydro-4-pyrimidinyl]amino}methyl)benzonitrile

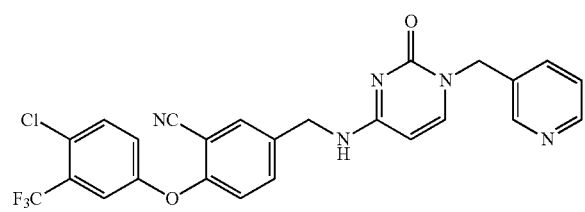 [SMILES: N#Cc1cc(CNc2ccn(Cc3cccnc3)c(=O)n2)ccc1Oc1ccc(Cl)c(C(F)(F)F)c1]

The title compound was prepared with a procedure similar to that described for E1 starting from 2-{[4-Chloro-3-(trifluoromethyl)phenyl]oxy}-5-{[(2-oxo-1,2-dihydro-4-pyrimidinyl)amino]methyl}benzonitrile and 3-(chloromethyl)pyridine hydrochloride. LC-MS (ESI): m/z 512 [M+H]$^+$; 3.70 min (ret time).

E20

5-(2-{1-[(1-Methyl-1H-pyrazol-4-yl)methyl]-2-oxo-1,2-dihydro-4-pyrimidinyl}ethyl)-2-{[3-(trifluoromethyl)phenyl]oxy}benzonitrile

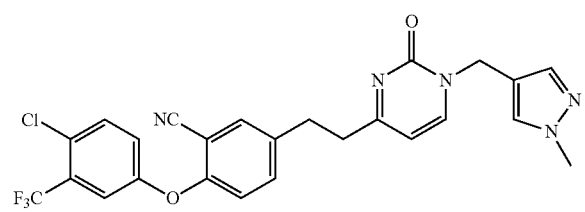 [SMILES: Cn1cc(Cn2ccc(CCc3ccc(Oc4ccc(Cl)c(C(F)(F)F)c4)c(C#N)c3)nc2=O)cn1]

The title compound was prepared with a procedure similar to that described for E1 starting form 5-[2-(2-oxo-1,2-dihydro-4-pyrimidinyl)ethyl]-2-{[3-(trifluoromethyl)phenyl]oxy}-benzonitrile and 4-(chloromethyl)-1-methyl-1H-pyrazole hydrochloride. LC-MS (ESI): m/z 480 [M+H]$^+$; 2.90 min (ret time).

E21

2-(4-chloro-3-(trifluoromethyl)phenoxy)-5-(2-(1-((1-methyl-1H-pyrazol-4-yl)methyl)-2-oxo-1,2-dihydropyrimidin-4-yl)ethyl)benzonitrile

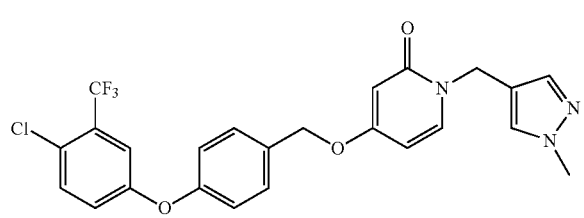 [SMILES: Cn1cc(Cn2ccc(OCc3ccc(Oc4ccc(Cl)c(C(F)(F)F)c4)cc3)cc2=O)cn1]

To a solution of 4-{[(4-{[4-chloro-3-(trifluoromethyl)phenyl]oxy}phenyl)methyl]oxy}-2(1H)-pyridinone (20 mg, 0.051 mmol) in N,N-dimethylformamide (1 mL) was added sodium hydride (8.0 mg, 0.20 mmol) in one portion. After 15 min, 4-(chloromethyl)-1-methyl-1H-pyrazole (16 mg, 0.123 mmol) was added. The reaction mixture was stirred at rt overnight, then quenched by addition of methanol, concentrated. Purification via Biotage-C$_{18}$ system afforded the title product (5.6 mg) as a white solid. LC-MS (ESI): m/z 490 [M+H]$^+$; 3.59 min (ret time).

E22

2-{[4-Chloro-3-(trifluoromethyl)phenyl]oxy}-5-[({1-[(1-methyl-1H-pyrazol-4-yl)methyl]-2-oxo-1,2-dihydro-4-pyridinyl}oxy)methyl]benzonitrile

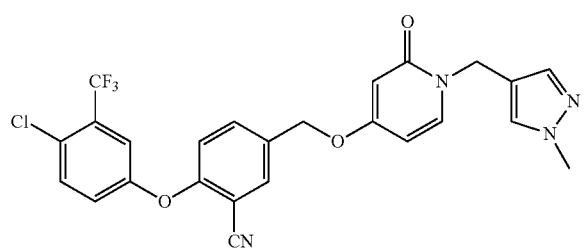 [SMILES: Cn1cc(Cn2ccc(OCc3ccc(Oc4ccc(Cl)c(C(F)(F)F)c4)c(C#N)c3)cc2=O)cn1]

To a solution of 2-{[4-Chloro-3-(trifluoromethyl)phenyl]oxy}-5-{[(2-oxo-1,2-dihydro-4-pyridinyl)oxy]methyl}benzonitrile (60 mg, 0.143 mmol) in N,N-dimethylformamide (2 mL) was added Sodium hydride (40 mg, 1.00 mmol) at rt in one portion. After stirring at rt for 10 min, 4-(chloromethyl)-1-methyl-1H-pyrazole (40 mg, 0.306 mmol) was added. The reaction mixture was heated at 60° C. in the microwave for 30 min, then quenched by addition of methanol, concentrated. Purification via Biotage-C$_{18}$ system afforded the title product (13.6 mg) as a white solid. LC-MS (ESI): m/z 515 [M+H]$^+$; 3.36 min (ret time).

E23

4-{[(4-{[4-Chloro-3-(trifluoromethyl)phenyl]oxy}phenyl)methyl]oxy}-1-ethyl-2(1H)-pyridinone

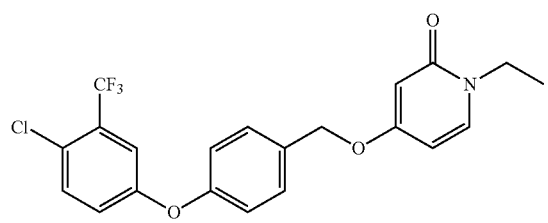 [SMILES: CCn1ccc(OCc2ccc(Oc3ccc(Cl)c(C(F)(F)F)c3)cc2)cc1=O]

To a solution of 4-{[(4-{[4-chloro-3-(trifluoromethyl)phenyl]oxy}phenyl)methyl]oxy}-2(1H)-pyridinone (80 mg, 0.202 mmol) in N,N-dimethylformamide (1 mL) was added Sodium hydride (80 mg, 2.00 mmol). After stirring at rt for 10 min, bromoethane (100 μL, 1.34 mmol) was added. The reaction mixture was warmed to 80° C. and stirred for 1 h, then cooled to rt, quenched by addition of methanol, concentrated. Purification via Biotage-Qs system afforded the title product (59.5 mg) as a white solid. LC-MS (ESI): m/z 424 [M+H]$^+$; 3.76 min (ret time).

E24

4-{[2-(4-{[4-Chloro-3-(trifluoromethyl)phenyl]oxy}phenyl)ethyl]oxy}-1-[(1-methyl-1H-pyrazol-4-yl)methyl]-2(1H)-pyridinone

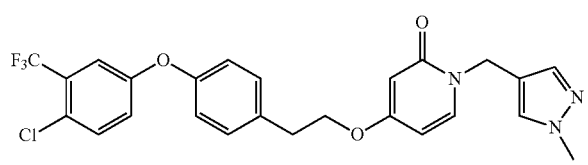 [SMILES: Cn1cc(Cn2ccc(OCCc3ccc(Oc4ccc(Cl)c(C(F)(F)F)c4)cc3)cc2=O)cn1]

The title compound was prepared by a procedure similar to that described for E21 starting from 4-{[2-(4-{[4-chloro-3-(trifluoromethyl)phenyl]oxy}phenyl)ethyl]oxy}-2 (1H)-pyridinone and 4-(Chloromethyl)-1-methyl-1H-pyrazole. LC-MS (ESI): m/z 504 [M+H]$^+$; 3.68 min (ret time).

E25

1-[(1-Methyl-1H-pyrazol-4-yl)methyl]-4-{[(4-{[3-(trifluoromethyl)phenyl]oxy}-phenyl)methyl]oxy}-2(1H)-pyridinone

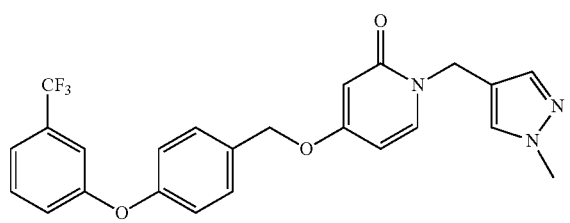 [SMILES: Cn1cc(Cn2ccc(OCc3ccc(Oc4cccc(C(F)(F)F)c4)cc3)cc2=O)cn1]

The title compound was prepared by a procedure similar to that described for E21 starting from 4-{[(4-{[3-(trifluoromethyl)phenyl]oxy}phenyl)methyl]oxy}-2(1H)-pyridinone and 4-(chloromethyl)-1-methyl-1H-pyrazole. LC-MS (ESI): m/z 456 [M+H]$^+$; 3.40 min (ret time).

E26

4-{[(4-{[4-Chloro-3-(trifluoromethyl)phenyl]oxy}phenyl)methyl]oxy}-1-(5-pyrimidinylmethyl)-2(1H)-pyridinone

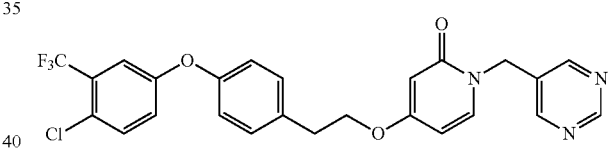

The title compound was prepared by a procedure similar to that described for E21 starting from 4-{[(4-{[4-Chloro-3-(trifluoromethyl)phenyl]oxy}phenyl)methyl]oxy}-2 (1H)-pyridinone and 5-(chloromethyl)pyrimidine. LC-MS (ESI): m/z 488 [M+H]$^+$; 3.57 min (ret time).

E27

4-{[2-(4-{[4-Chloro-3-(trifluoromethyl)phenyl]oxy}phenyl)ethyl]oxy}-1-(5-pyrimidinylmethyl)-2(1H)-pyridinone

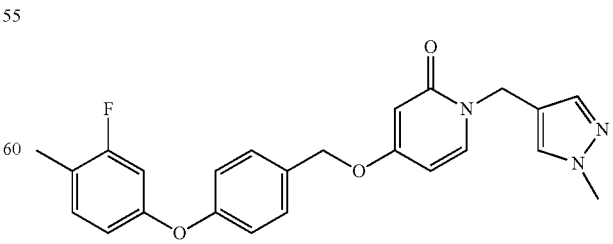

The title compound was prepared by a procedure similar to that described for E21 starting from 4-{[2-(4-{[4-chloro-3-(trifluoromethyl)phenyl]oxy}phenyl)ethyl]oxy}-2(1H)-pyridinone and 5-(chloromethyl)pyrimidine. LC-MS (ESI): m/z 502 [M+H]$^+$; 3.68 min (ret time).

E28

4-[({4-[(3-Fluoro-4-methylphenyl)oxy]phenyl}methyl)oxy]-1-[(1-methyl-1H-pyrazol-4-yl)methyl]-2(1H)-pyridinone The title compound was prepared by a procedure similar to that described for E21 starting from 4-[({4-[(3-fluoro-4-methylphenyl)oxy]phenyl}methyl)oxy]-2(1H)-pyridinone and 4-(chloromethyl)-1-methyl-1H-pyrazole. LC-MS (ESI): m/z 420 [M+H]$^+$; 3.35 min (ret time).

E29

4-{[2-(4-{[4-Chloro-3-(trifluoromethyl)phenyl]oxy}phenyl)ethyl]oxy}-5-fluoro-1-[(1-methyl-1H-pyrazol-4-yl)methyl]-2(1H)-pyrimidinone

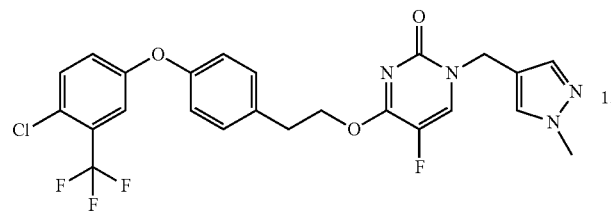

The title compound was prepared by a procedure similar to that described for E1 starting from 4-{[2-(4-{[4-chloro-3-(trifluoromethyl)phenyl]oxy}phenyl)ethyl]oxy}-5-fluoro-2(1H)-pyrimidinone. LC-MS (ESI): m/z 523 [M+H]$^+$; 4.79 min (ret time).

E30

5-chloro-4-{[2-(4-{[4-Chloro-3-(trifluoromethyl)phenyl]oxy}phenyl)ethyl]oxy}-1-[(1-methyl-1H-pyrazol-4-yl)methyl]-2(1H)-pyrimidinone

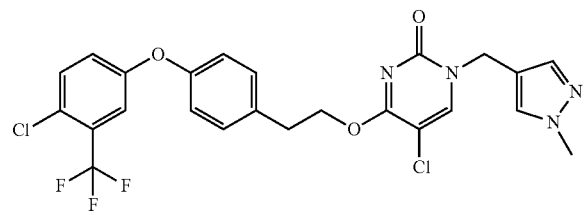 [SMILES: Cn1cc(Cn2cc(Cl)c(OCCc3ccc(Oc4ccc(Cl)c(C(F)(F)F)c4)cc3)nc2=O)cn1]

The title compound was prepared by a procedure similar to that described for E1 starting from 5-chloro-4-{[2-(4-{[4-chloro-3-(trifluoromethyl)phenyl]oxy}phenyl)ethyl]oxy}-2(1H)-pyrimidinone. LC-MS (ESI): m/z 539 [M+H]$^+$; 3.80 min (ret time).

E31

5-Chloro-4-(2-(6-(4-chloro-3-(trifluoromethyl)phenoxy)-5-fluoropyridin-3-yl)ethoxy)-1-((1-methyl-1H-pyrazol-4-yl)methyl)pyrimidin-2(1H)-one

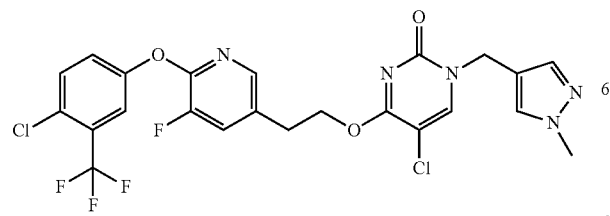

The title compound was prepared by a procedure similar to that described for E1 starting from 5-chloro-4-(2-(6-(4-chloro-3-(trifluoromethyl)phenoxy)-5-fluoropyridin-3-yl)ethoxy)pyrimidin-2-ol. LC-MS (ESI): m/z 558 [M+H]$^+$; 3.55 min (ret time).

E32

5-chloro-4-(2-(6-(4-chloro-3-(trifluoromethyl)phenoxy)-5-fluoropyridin-3-yl)ethoxy)-1-((2-methoxypyrimidin-5-yl)methyl)pyrimidin-2(1H)-one

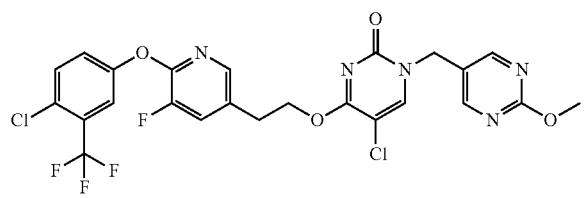 [SMILES: COc1ncc(Cn2cc(Cl)c(OCCc3cnc(Oc4ccc(Cl)c(C(F)(F)F)c4)c(F)c3)nc2=O)cn1]

The title compound was prepared by a procedure similar to that described for E1 starting from 5-chloro-4-(2-(6-(4-Chloro-3-(trifluoromethyl)phenoxy)-5-fluoropyridin-3-yl)ethoxy)pyrimidin-2-ol. LC-MS (ESI): m/z 586 [M+H]$^+$; 3.64 min (ret time).

E33

4-(2-(6-(4-chloro-3-(trifluoromethyl)phenoxy)-5-fluoropyridin-3-yl)ethoxy)-5-fluoro-1-((1-methyl-1H-pyrazol-4-yl)methyl)pyrimidin-2(1H)-one

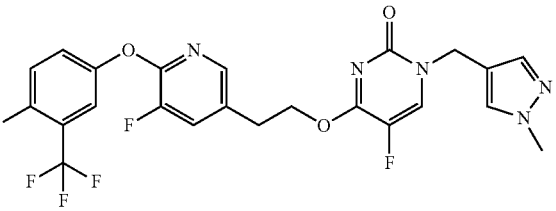

The title compound was prepared by a procedure similar to that described for E1 starting from 4-(2-(6-(4-chloro-3-(trifluoromethyl)phenoxy)-5-fluoropyridin-3-yl)ethoxy)-5-fluoropyrimidin-2(1H)-one. LC-MS (ESI): m/z 542 [M+H]$^+$; 3.45 min (ret time).

E34

4-(2-(6-(4-chloro-3-(trifluoromethyl)phenoxy)-5-fluoropyridin-3-yl)ethoxy)-5-fluoro-1-((2-methoxypyrimidin-5-yl)methyl)pyrimidin-2(1H)-one

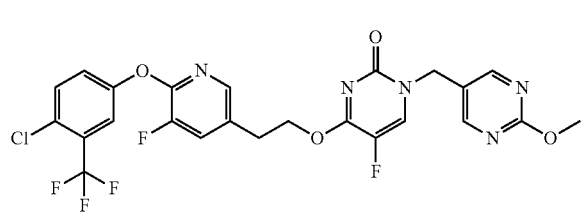 [SMILES: COc1ncc(Cn2cc(F)c(OCCc3cnc(Oc4ccc(Cl)c(C(F)(F)F)c4)c(F)c3)nc2=O)cn1]

The title compound was prepared by a procedure similar to that described for E1 starting from 4-(2-(6-(4-chloro-3-(trifluoromethyl)phenoxy)-5-fluoropyridin-3-yl)ethoxy)-5-fluoropyrimidin-2(1H)-one. LC-MS (ESI): m/z 570 [M+H]+; 4.20 min (ret time).

E35

5-chloro-1-((2-methoxypyrimidin-5-yl)methyl)-4-(2-(4'-(trifluoromethyl)-[1,1'-biphenyl]-4-yl)ethoxy)pyrimidin-2(1H)-one

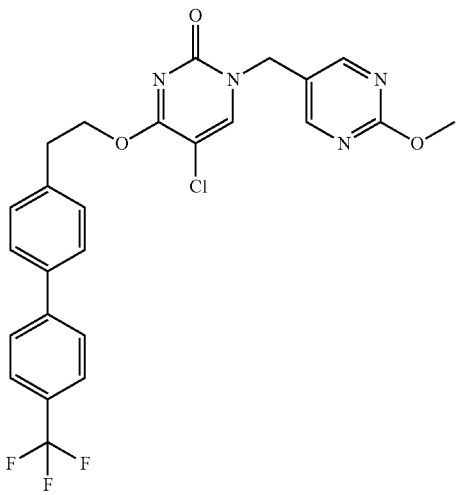 [SMILES: COc1ncc(Cn2cc(Cl)c(OCCc3ccc(-c4ccc(C(F)(F)F)cc4)cc3)nc2=O)cn1]

The title compound was prepared by a procedure similar to that described for E1 starting from 5-chloro-4-(2-(4'-(trifluoromethyl)-[1,1'-biphenyl]-4-yl)ethoxy)pyrimidin-2(1H)-one. LC-MS (ESI): m/z 517 [M+H]+; 4.37 min (ret time).

E36

4-(4-(4-chloro-3-(trifluoromethyl)phenoxy)phenethoxy)-5-fluoro-1-((2-methoxy pyrimidin-5-yl)methyl)pyrimidin-2(1H)-one

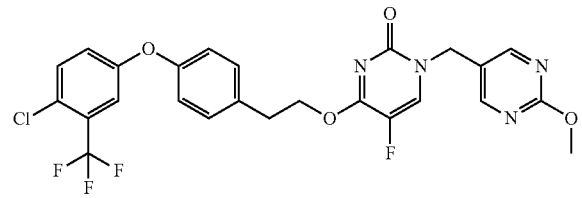

The title compound was prepared by a procedure similar to that described for E1 starting from 4 4-(4-(4-chloro-3-(trifluoromethyl)phenoxy)phenethoxy)-5-fluoropyrimidin-2(1H)-one. LC-MS (ESI): m/z 551 [M+H]+; 4.41 min (ret time).

E37

5-chloro-4-(2-(5-fluoro-6-(4-fluoro-3-(trifluoromethyl)phenoxy)pyridin-3-yl)ethoxy)-1-((2-methoxypyrimidin-5-yl)methyl)pyrimidin-2(1H)-one

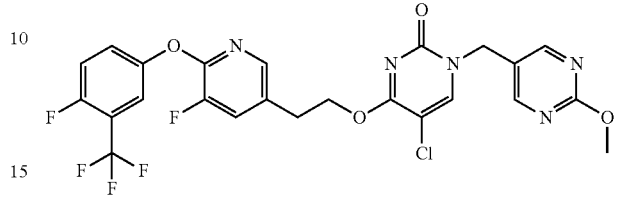

The title compound was prepared by a procedure similar to that described for E1 starting from 5-Chloro-4-(2-(5-fluoro-6-(4-fluoro-3-(trifluoromethyl)phenoxy)pyridin-3-yl)ethoxy)pyrimidin-2(1H)-one. LC-MS (ESI): m/z 570 [M+H]+; 4.15 min (ret time).

E38

5-chloro-4-(2-(5-fluoro-6-(4-fluoro-3-(trifluoromethyl)phenoxy)pyridin-3-yl)ethoxy)-1-((1-methyl-1H-pyrazol-4-yl)methyl)pyrimidin-2(1H)-one

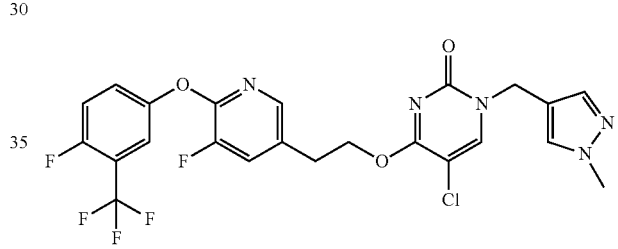

The title compound was prepared by a procedure similar to that described for E1 starting from 5-chloro-4-(2-(5-fluoro-6-(4-fluoro-3-(trifluoromethyl)phenoxy)pyridin-3-yl)ethoxy)pyrimidin-2(1H)-one. LC-MS (ESI): m/z 542 [M+H]+; 4.08 min (ret time).

E39

5-fluoro-4-(2-(6-(4-fluoro-3-(trifluoromethyl)phenoxy)pyridin-3-yl)ethoxy)-1-((1-methyl-1H-pyrazol-4-yl)methyl)pyrimidin-2(1H)-one

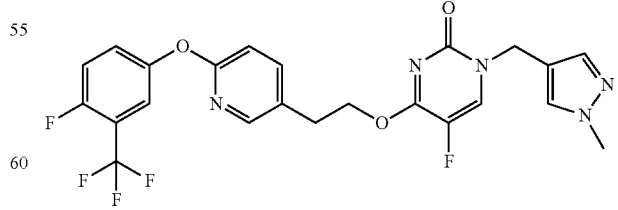

The title compound was prepared by a procedure similar to that described for E1 starting from 5-fluoro-4-(2-(6-(4-fluoro-3-(trifluoromethyl)phenoxy)pyridin-3-yl)ethoxy)pyrimidin-2(1H)-one. LC-MS (ESI): m/z 508 [M+H]+; 3.84 min (ret time).

E40

4-(2-(6-(4-chloro-3-(trifluoromethyl)phenoxy)pyridin-3-yl)ethoxy)-5-fluoro-1-((1-methyl-1H-pyrazol-4-yl)methyl)pyrimidin-2(1H)-one

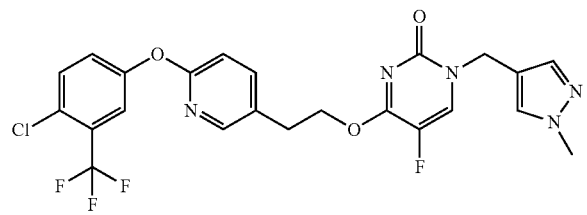 [SMILES: Cn1cc(Cn2cc(F)c(OCCc3ccc(Oc4ccc(Cl)c(C(F)(F)F)c4)nc3)nc2=O)cn1]

The title compound was prepared by a procedure similar to that described for E1 starting from 4-(2-(6-(4-Chloro-3-(trifluoromethyl)phenoxy)pyridin-3-yl)ethoxy)-5-fluoropyrimidin-2(1H)-one. LC-MS (ESI): m/z 524 [M+H]$^+$; 4.01 min (ret time).

E41

5-fluoro-4-(3-fluoro-4-((6-(trifluoromethyl)pyridin-3-yl)oxy)phenethoxy)-1-((1-methyl-1H-pyrazol-4-yl)methyl)pyrimidin-2(1H)-one

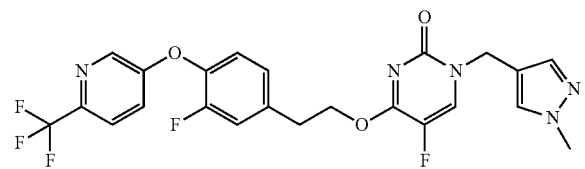 [SMILES: Cn1cc(Cn2cc(F)c(OCCc3ccc(Oc4ccc(C(F)(F)F)nc4)c(F)c3)nc2=O)cn1]

The title compound was prepared by a procedure similar to that described for E1 starting from 4-(2-(6-(4-Chloro-3-(trifluoromethyl)phenoxy)pyridin-3-yl)ethoxy)-5-fluoropyrimidin-2(1H)-one. LC-MS (ESI): m/z 508 [M+H]$^+$; 3.16 min (ret time).

E42

5-fluoro-4-(2-(5-fluoro-6-(4-fluoro-3-(trifluoromethyl)phenoxy)pyridin-3-yl)ethoxy)-1-((1-methyl-1H-pyrazol-4-yl)methyl)pyrimidin-2(1H)-one

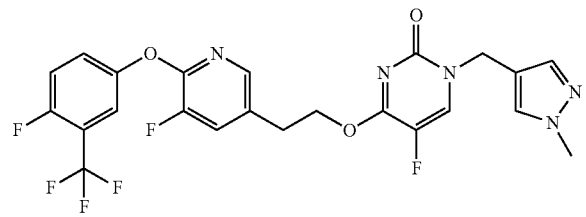 [SMILES: Cn1cc(Cn2cc(F)c(OCCc3cnc(Oc4ccc(F)c(C(F)(F)F)c4)c(F)c3)nc2=O)cn1]

The title compound was prepared by a procedure similar to that described for E1 starting from 5-fluoro-4-(2-(5-fluoro-6-(4-fluoro-3-(trifluoromethyl)phenoxy)pyridin-3-yl)ethoxy)pyrimidin-2(1H)-one. LC-MS (ESI): m/z 525 [M+H]$^+$; 3.96 min (ret time).

E43

5-fluoro-4-(2-(5-fluoro-6-(4-fluoro-3-(trifluoromethyl)phenoxy)pyridin-3-yl)ethoxy)-1-((2-methoxypyrimidin-5-yl)methyl)pyrimidin-2(1H)-one

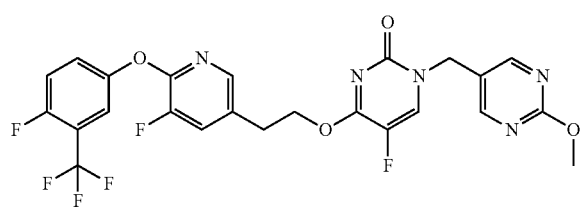

The title compound was prepared by a procedure similar to that described for E1 starting from 5-fluoro-4-(2-(5-fluoro-6-(4-fluoro-3-(trifluoromethyl)phenoxy)pyridin-3-yl)ethoxy)pyrimidin-2(1H)-one. LC-MS (ESI): m/z 554 [M+H]$^+$; 4.04 min (ret time).

E44

5-chloro-4-(4-(4-chloro-3-(trifluoromethyl)benzyl)phenethoxy)-1-((1-methyl-1H-pyrazol-4-yl)methyl)pyrimidin-2(1H)-one

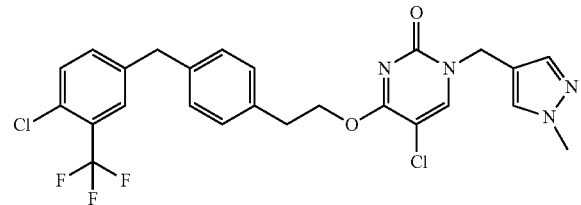

The title compound was prepared by a procedure similar to that described for E1 starting from 5-chloro-4-(4-(4-chloro-3-(trifluoromethyl)benzyl)phenethoxy)pyrimidin-2(1H)-one (D98). LC-MS (ESI): m/z 538 [M+H]$^+$; 3.77 min (ret time).

E45

5-chloro-4-(4-(4-chloro-3-(trifluoromethyl)benzyl)phenethoxy)-1-((2-methoxy pyrimidin-5-yl)methyl)pyrimidin-2(1H)-one

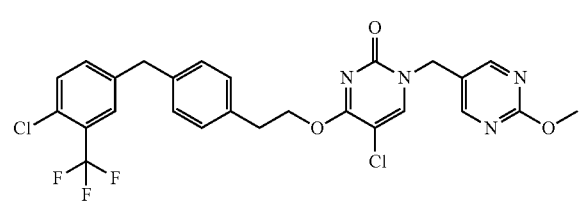 [SMILES: COc1ncc(Cn2cc(Cl)c(OCCc3ccc(Cc4ccc(Cl)c(C(F)(F)F)c4)cc3)nc2=O)cn1]

The title compound was prepared by a procedure similar to that described for E1 starting from 5-chloro-4-(2-(5-fluoro- 6-(4-fluoro-3-(trifluoromethyl)phenoxy)pyridin-3-yl)ethoxy)pyrimidin-2(1H)-one. LC-MS (ESI): m/z 564 [M+H]⁺; 3.85 min (ret time).

E46

4-(4-(4-chloro-3-(trifluoromethyl)benzyl)phenethoxy)-5-fluoro-1-((1-methyl-1H-pyrazol-4-yl)methyl)pyrimidin-2(1H)-one

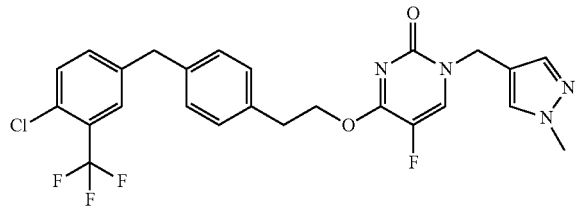

The title compound was prepared by a procedure similar to that described for E1 starting from 4-(4-(4-Chloro-3-(trifluoromethyl)benzyl)phenethoxy)-5-fluoropyrimidin-2(1H)-one. LC-MS (ESI): m/z 521 [M+H]⁺; 4.33 min (ret time).

E47

4-(4-(4-chloro-3-(trifluoromethyl)benzyl)phenethoxy)-5-fluoro-1-((2-methoxy pyrimidin-5-yl)methyl)pyrimidin-2(1H)-one

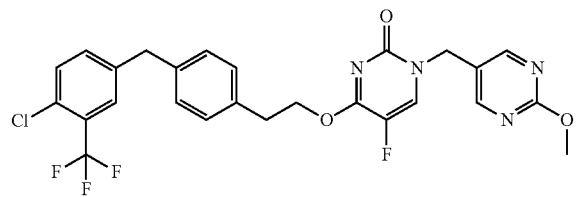 [SMILES: COc1ncc(Cn2cc(F)c(OCCc3ccc(Cc4ccc(Cl)c(C(F)(F)F)c4)cc3)nc2=O)cn1]

The title compound was prepared by a procedure similar to that described for E1 starting from 4-(4-(4-chloro-3-(trifluoromethyl)benzyl)phenethoxy)-5-fluoropyrimidin-2(1H)-one. LC-MS (ESI): m/z 548 [M+H]⁺; 441 min (ret time).

E48

5-chloro-1-((1-methyl-1H-pyrazol-4-yl)methyl)-4-(4-((4-(trifluoromethyl)pyrimidin-2-yl)oxy)phenethoxy)pyrimidin-2(1H)-one

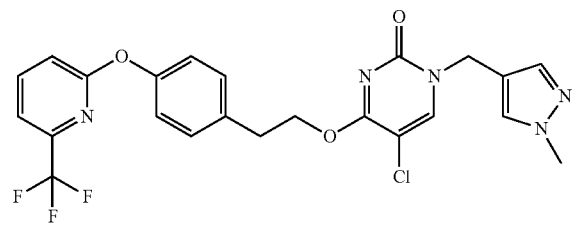 [SMILES: Cn1cc(Cn2cc(Cl)c(OCCc3ccc(Oc4cccc(C(F)(F)F)n4)cc3)nc2=O)cn1]

The title compound was prepared by a procedure similar to that described for E1 starting from 5-chloro-4-(2-(5-fluoro-6-(4-fluoro-3-(trifluoromethyl)phenoxy)pyridin-3-yl)ethoxy)pyrimidin-2(1H)-one. LC-MS (ESI): m/z 507 [M+H]⁺; 3.65 min (ret time).

E49

5-chloro-1-((2-methoxypyrimidin-5-yl)methyl)-4-(4-((4-(trifluoromethyl)pyrimidin-2-yl)oxy)phenethoxy)pyrimidin-2(1H)-one

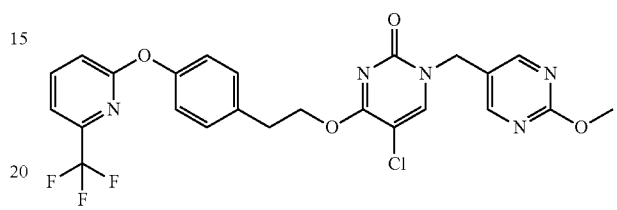

The title compound was prepared by a procedure similar to that described for E1 starting from 5-chloro-4-(2-(5-fluoro-6-(4-fluoro-3-(trifluoromethyl)phenoxy)pyridin-3-yl)ethoxy)pyrimidin-2(1H)-one. LC-MS (ESI): m/z 535 [M+H]⁺; 3.74 min (ret time).

E50

5-chloro-1-((1-methyl-1H-pyrazol-4-yl)methyl)-4-(4-((6-(trifluoromethyl)pyridin-2-yl)oxy)phenethoxy)pyrimidin-2(1H)-one

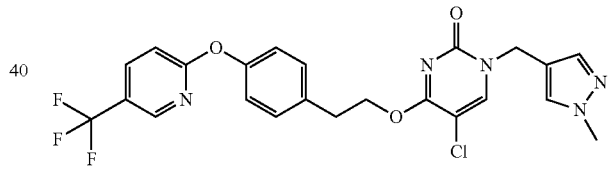

The title compound was prepared by a procedure similar to that described for E1 starting from 5-chloro-4-(4-((5-(trifluoromethyl)pyridin-2-yl)oxy)phenethoxy)pyrimidin-2(1H)-one. LC-MS (ESI): m/z 506 [M+H]⁺; 3.96 min (ret time).

E51

5-Chloro-1-((2-methoxypyrimidin-5-yl)methyl)-4-(4-((6-(trifluoromethyl)pyridin-2-yl)oxy)phenethoxy)pyrimidin-2(1H)-one

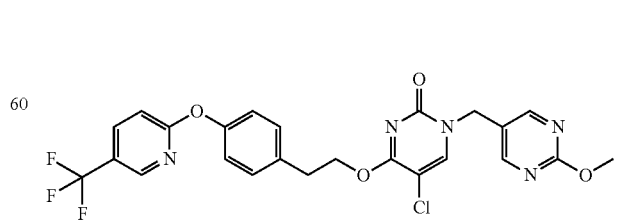

The title compound was prepared by a procedure similar to that described for E1 starting from 5-chloro-4-(4-((5-(trifluoromethyl)pyridin-2-yl)oxy)phenethoxy)pyrimidin-2(1H)-one. LC-MS (ESI): m/z 534 [M+H]⁺; 3.91 min (ret time).

E52

4-(2-(6-(4-chloro-3-(trifluoromethyl)phenoxy)pyridin-3-yl)ethoxy)-1-ethyl-5-fluoropyrimidin-2(1H)-one

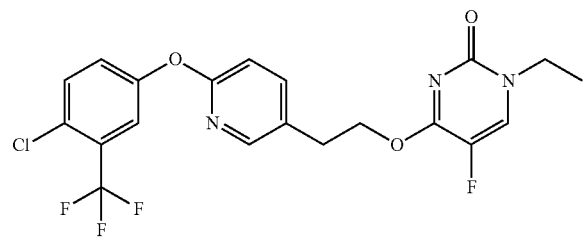 [SMILES: CCn1cc(F)c(OCCc2ccc(Oc3ccc(Cl)c(C(F)(F)F)c3)nc2)nc1=O]

The title compound was prepared by a procedure similar to that described for E1 starting from 4-(2-(6-(4-chloro-3-(trifluoromethyl)phenoxy)pyridin-3-yl)ethoxy)-5-fluoropyrimidin-2(1H)-one. LC-MS (ESI): m/z 458 [M+H]⁺; 3.50 min (ret time).

E53

5-chloro-4-((4-(3,4-difluorophenoxy)-3-fluorobenzyl)oxy)-1-((1-methyl-1H-pyrazol-4-yl)methyl)pyrimidin-2 (1H)-one

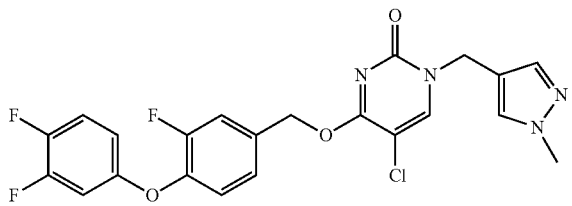 [SMILES: Cn1cc(Cn2cc(Cl)c(OCc3ccc(Oc4ccc(F)c(F)c4)c(F)c3)nc2=O)cn1]

The title compound was prepared by a procedure similar to that described for E1 starting from 5-Chloro-4-((4-(3,4-difluorophenoxy)-3-fluorobenz-yl)oxy)pyrimidin-2(1H)-one. LC-MS (ESI): m/z 477 [M+H]⁺; 4.00 min (ret time).

E54

5-chloro-4-((4-(3,4-difluorophenoxy)-3-fluorobenzyl)oxy)-1-((2-methoxypyrimidin-5-yl)methyl)pyrimidin-2(1H)-one

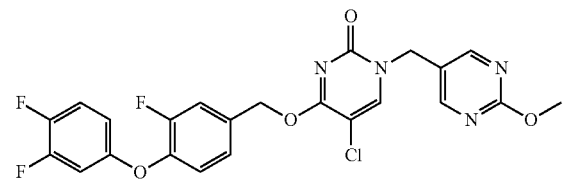 [SMILES: COc1ncc(Cn2cc(Cl)c(OCc3ccc(Oc4ccc(F)c(F)c4)c(F)c3)nc2=O)cn1]

The title compound was prepared by a procedure similar to that described for E1 starting from 5-chloro-4-((4-(3,4-difluorophenoxy)-3-fluorobenzyl)oxy)pyrimidin-2(1H)-one. LC-MS (ESI): m/z 505 [M+H]⁺; 4.07 min (ret time).

E55

4-(2-(5-(4-chloro-3-(trifluoromethyl)phenoxy)pyridin-2-yl)ethoxy)-5-fluoro-1-((1-methyl-1H-pyrazol-4-yl)methyl)pyrimidin-2(1H)-one

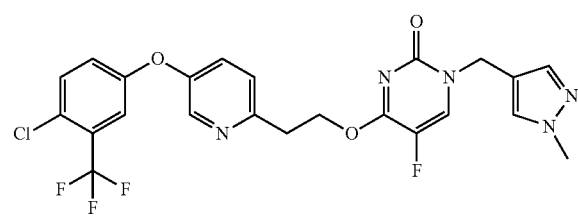

The title compound was prepared by a procedure similar to that described for E1 starting from 4-(2-(5-(4-chloro-3-(trifluoromethyl)phenoxy)pyridin-2-yl)ethoxy)-5-fluoropyrimidin-2(1H)-one. LC-MS (ESI): m/z 524 [M+H]⁺; 2.92 min (ret time).

E56

1-ethyl-5-fluoro-4-(3-fluoro-4-((6-(trifluoromethyl)pyridin-3-yl)oxy)phenethoxy)pyrimidin-2(1H)-one

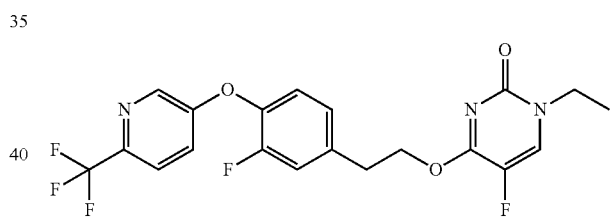

The title compound was prepared by a procedure similar to that described for E1 starting from 5-fluoro-4-(3-fluoro-4-((6-(trifluoromethyl)pyridin-3-yl)oxy)phenethoxy)pyrimidin-2(1H)-one. LC-MS (ESI): m/z 442 [M+H]⁺; 2.91 min (ret time).

E57

5-fluoro-1-((1-methyl-1H-pyrazol-4-yl)methyl)-4-(4-((6-(trifluoromethyl)pyridin-2-yl)oxy)phenethoxy)pyrimidin-2(1H)-one

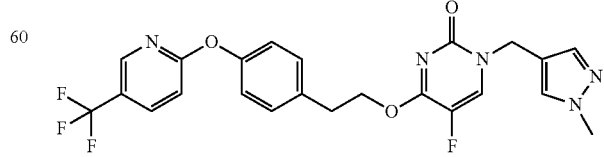

The title compound was prepared by a procedure similar to that described for E1 starting from 5-fluoro-4-(4-((5-(trifluoromethyl)pyridin-2-yl)oxy)phenethoxy)pyrimidin-2(1H)-one. LC-MS (ESI): m/z 490 [M+H]⁺; 3.82 min (ret time).

E58

5-fluoro-1-((2-methoxypyrimidin-5-yl)methyl)-4-(4-((6-(trifluoromethyl)pyridin-2-yl)oxy)phenethoxy)pyrimidin-2(1H)-one

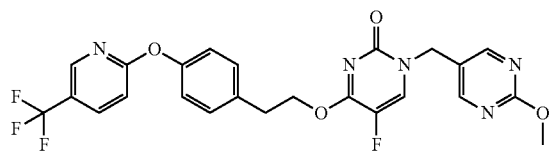 [SMILES: COc1ncc(Cn2cc(F)c(OCCc3ccc(Oc4ccc(C(F)(F)F)cn4)cc3)nc2=O)cn1]

The title compound was prepared by a procedure similar to that described for E1 starting from 5-fluoro-4-(4-((5-(trifluoromethyl)pyridin-2-yl)oxy)phenethoxy)pyrimidin-2(1H)-one. LC-MS (ESI): m/z 518 [M+H]⁺; 3.91 min (ret time).

E59

4-(4-(3,4-difluorophenoxy)-3-fluorophenethoxy)-5-fluoro-1-((1-methyl-1H-pyrazol-4-yl)methyl)pyrimidin-2(1H)-one, trifluoroacetic acid salt

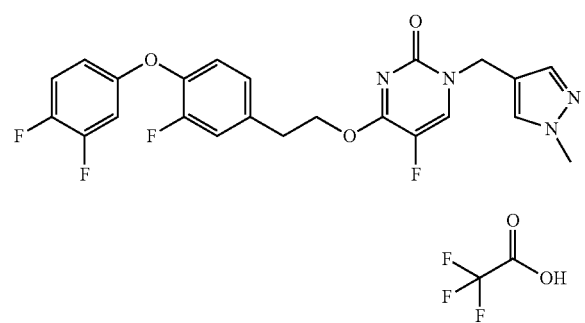 [SMILES: Cn1cc(Cn2cc(F)c(OCCc3ccc(Oc4ccc(F)c(F)c4)c(F)c3)nc2=O)cn1 ; O=C(O)C(F)(F)F]

The title compound was prepared by a procedure similar to that described for E1 starting from 4-(4-(3,4-difluorophenoxy)-3-fluorophenethoxy)-5-fluoropyrimidin-2(1H)-one. LC-MS (ESI): m/z 475 [M+H]⁺; 3.30 min (ret time).

E60

5-fluoro-4-(3-fluoro-4-((6-(trifluoromethyl)pyridin-2-yl)oxy)phenethoxy)-1-((1-methyl-1H-pyrazol-4-yl)methyl)pyrimidin-2(1H)-one

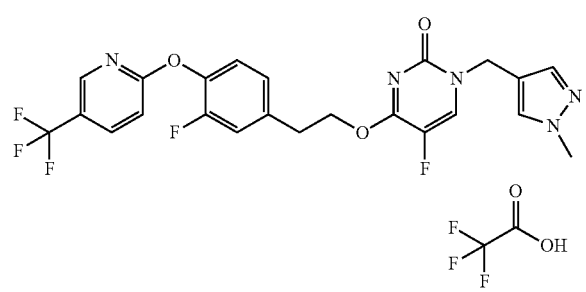 [SMILES: Cn1cc(Cn2cc(F)c(OCCc3ccc(Oc4ccc(C(F)(F)F)cn4)c(F)c3)nc2=O)cn1 ; O=C(O)C(F)(F)F]

The title compound was prepared by a procedure similar to that described for E1 starting from 5-fluoro-4-(3-fluoro-4-((5-(trifluoromethyl)pyridin-2-yl)oxy)phenethoxy)pyrimidin-2(1H)-one. LC-MS (ESI): m/z 508 [M+H]⁺; 3.24 min (ret time).

E61

5-fluoro-1-((1-methyl-1H-pyrazol-4-yl)methyl)-4-(4-((6-methylpyridin-2-yl)oxy)phenethoxy)pyrimidin-2(1H)-one

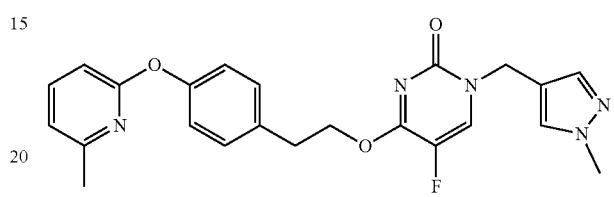

The title compound was prepared by a procedure similar to that described for E1 starting from 5-fluoro-4-(4-((6-methylpyridin-2-yl)oxy)phenethoxy)pyrimidin-2(1H)-one. LC-MS (ESI): m/z 436 [M+H]⁺; 2.65 min (ret time).

E62

5-fluoro-1-((2-methoxypyrimidin-5-yl)methyl)-4-(4-((6-methylpyridin-2-yl)oxy) phenethoxy)pyrimidin-2(1H)-one

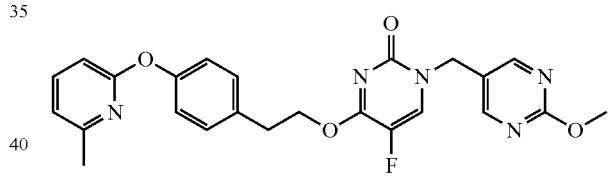

The title compound was prepared by a procedure similar to that described for E1 starting from 5-fluoro-4-(4-((6-methylpyridin-2-yl)oxy)phenethoxy)pyrimidin-2(1H)-one. LC-MS (ESI): m/z 464 [M+H]⁺; 2.73 min (ret time).

E63

1-ethyl-5-fluoro-4-(4-((6-(trifluoromethyl)pyridin-2-yl)oxy)phenethoxy)pyrimidin-2(1H)-one, trifluoroacetic acid salt

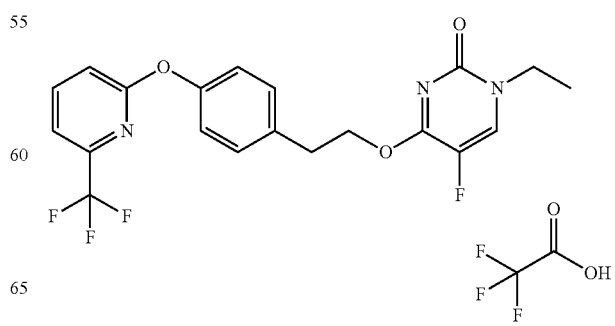

E64

5-fluoro-1-((1-methyl-1H-pyrazol-4-yl)methyl)-4-(4-((6-(trifluoromethyl)pyridin-2-yl)oxy)phenethoxy)pyrimidin-2(1H)-one

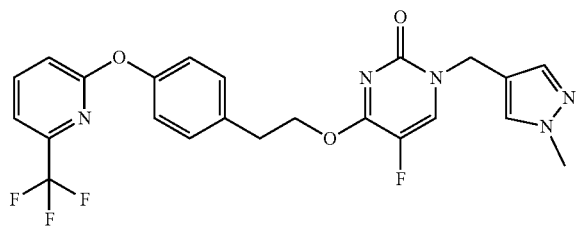 [SMILES: Cn1cc(Cn2cc(F)c(OCCc3ccc(Oc4cccc(C(F)(F)F)n4)cc3)nc2=O)cn1]

The title compound was prepared by a procedure similar to that described for E1 starting from 5-fluoro-4-(4-((6-(trifluoromethyl)pyridin-2-yl)oxy)phenethoxy)pyrimidin-2(1H)-one. LC-MS (ESI): m/z 490 [M+H]⁺; 3.17 min (ret time).

E65

5-fluoro-1-((2-methoxypyrimidin-5-yl)methyl)-4-(4-((6-(trifluoromethyl)pyridin-2-yl)oxy)phenethoxy)pyrimidin-2(1H)-one

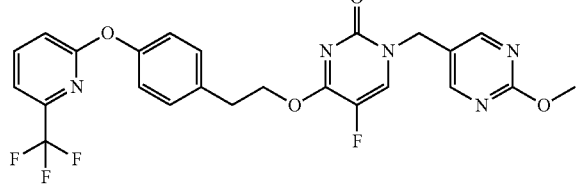

The title compound was prepared by a procedure similar to that described for E1 starting from 5 5-fluoro-4-(4-((6-(trifluoromethyl)pyridin-2-yl)oxy)phenethoxy)pyrimidin-2 (1H)-one. LC-MS (ESI): m/z 518 [M+H]⁺; 3.29 min (ret time).

E66

4-(4-(4-chloro-3-(trifluoromethyl)phenoxy)phenethoxy)-5-methyl-1-((1-methyl-1H-pyrazol-4-yl)methyl)pyrimidin-2 (1H)-one

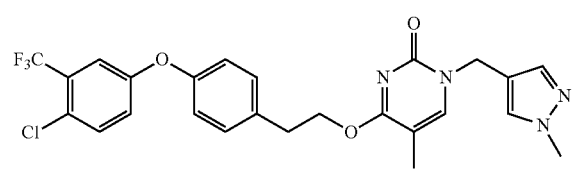 [SMILES: Cc1cn(Cc2cnn(C)c2)c(=O)nc1OCCc1ccc(Oc2ccc(Cl)c(C(F)(F)F)c2)cc1]

The title compound was prepared by a procedure similar to that described for E1 starting from 4-(4-(4-chloro-3-(trifluoromethyl)phenoxy)phenethoxy)-5-methylpyrimidin-2(1H)-one. LC-MS (ESI): m/z 519 [M+H]⁺; 3.72 min (ret time).

E67

4-(2-(6-(3,4-difluorophenoxy)pyridin-3-yl)ethoxy)-5-methyl-1-((1-methyl-1H-pyrazol-4-yl)methyl)pyrimidin-2(1H)-one

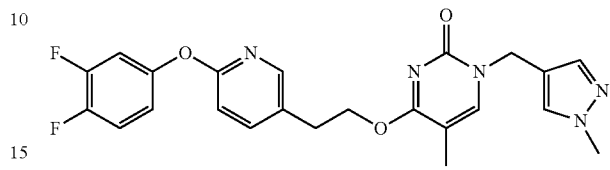

The title compound was prepared by a procedure similar to that described for E1 starting from 4-(2-(6-(3,4-difluorophenoxy)pyridin-3-yl)ethoxy)-5-methylpyrimidin-2(1H)-one. LC-MS (ESI): m/z 454 [M+H]⁺; 2.96 min (ret time).

E68

5-fluoro-1-((1-methyl-1H-pyrazol-4-yl)methyl)-4-(4-phenoxyphenethoxy)pyrimidin-2(1H)-one

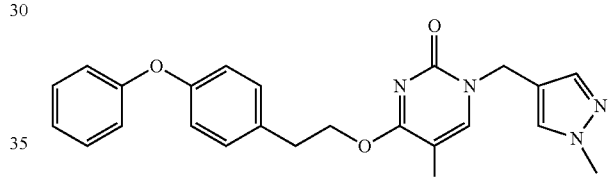

The title compound was prepared by a procedure similar to that described for E1 starting from 5-fluoro-4-(4-phenoxyphenethoxy)pyrimidin-2(1H)-one. LC-MS (ESI): m/z 421 [M+H]⁺; 3.18 min (ret time).

E69

5-(((5-methyl-1-((1-methyl-1H-pyrazol-4-yl)methyl)-2-oxo-1,2-dihydropyrimidin-4-yl)oxy)methyl)-2-(3-(trifluoromethyl)phenoxy)benzonitrile

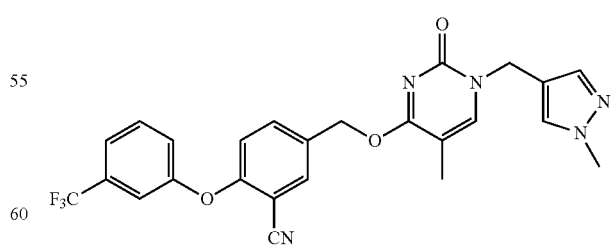

The title compound was prepared by a procedure similar to that described for E1 starting from 5-(((5-methyl-2-oxo-1,2-dihydropyrimidin-4-yl)oxy)methyl)-2-(3-(trifluoromethyl)phenoxy)benzonitrile. LC-MS (ESI): m/z 496 [M+H]⁺; 3.25 min (ret time).

E70

4-(2-(6-(3,4-difluorophenoxy)pyridin-3-yl)ethoxy)-1-((2-methoxypyrimidin-5-yl)methyl)-5-methylpyrimidin-2(1H)-one

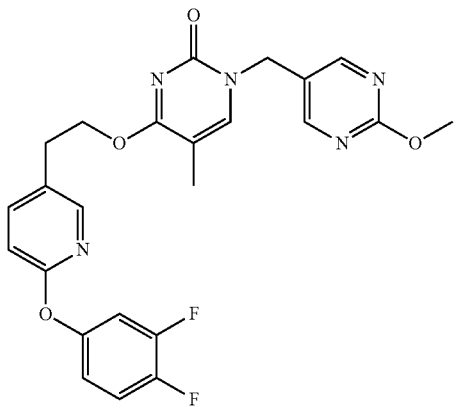 [SMILES: COc1ncc(Cn2cc(C)c(OCCc3ccc(Oc4ccc(F)c(F)c4)nc3)nc2=O)cn1]

The title compound was prepared by a procedure similar to that described for E1 starting from 4-(2-(6-(3,4-difluorophenoxy)pyridin-3-yl)ethoxy)-5-methylpyrimidin-2(1H)-one. LC-MS (ESI): m/z 482 [M+H]$^+$; 3.02 min (ret time).

E71

2-(3,4-difluorophenoxy)-5-(((5-methyl-1-((1-methyl-1H-pyrazol-4-yl)methyl)-2-oxo-1,2-dihydropyrimidin-4-yl)oxy)methyl)benzonitrile

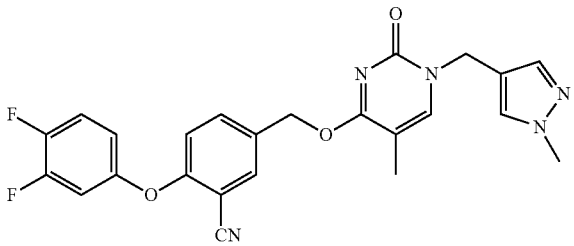 [SMILES: Cc1cn(Cc2cnn(C)c2)c(=O)nc1OCc1ccc(Oc2ccc(F)c(F)c2)c(C#N)c1]

The title compound was prepared by a procedure similar to that described for E1 starting from 2-(3,4-difluorophenoxy)-5-(((5-methyl-2-oxo-1,2-dihydropyrimidin-4-yl)oxy)methyl)benzonitrile. LC-MS (ESI): m/z 464 [M+H]$^+$; 3.08 min (ret time).

E72

4-((4-(3,4-difluorophenoxy)-3-fluorobenzyl)oxy)-5-methyl-1-((1-methyl-1H-pyrazol-4-yl)methyl)pyrimidin-2(1H)-one

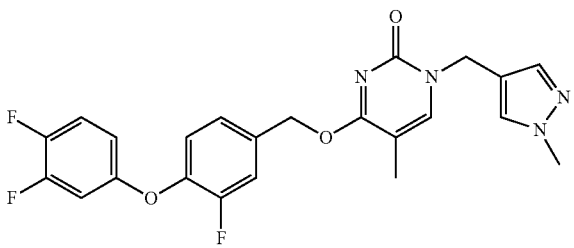 [SMILES: Cc1cn(Cc2cnn(C)c2)c(=O)nc1OCc1ccc(Oc2ccc(F)c(F)c2)c(F)c1]

The title compound was prepared by a procedure similar to that described for E1 starting from 4-((4-(3,4-difluorophenoxy)-3-fluorobenzyl)oxy)-5-methylpyrimidin-2(1H)-one LC-MS (ESI): m/z 457 [M+H]$^+$; 3.28 min (ret time).

D. BIOLOGICAL ASSAY AND DATA

The compounds of present invention are Lp-PLA$_2$ inhibitors, and are useful in the treatment of diseases mediated by Lp-PLA$_2$. The biological activities of the compounds of present invention can be determined by using any suitable assay for determining the activity of a compound as a Lp-PLA$_2$ inhibitor, as well as tissue and in vivo models.

The biological activity data for each compound was either reported in at least one experiment or the average of multiple experiments. It is understood that the data described herein may have reasonable variations depending on the specific conditions and procedures used by the person conducting the experiments.

Lipoprotein-Associated Phospholipase A2 (Lp-PLA$_2$) Biochemical Assay (1) Recombinant Human Lp-PLA$_2$ Assay (rhLp-PLA$_2$) (Also Referred to as "PED6" Assay)

N-((6-(2,4-dinitrophenyl)amino)-hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6) is a commercially available fluorescently-labelled phospholipid, which is commercially available from Molecular Probes. There is a quenching para-nitro phenyl (PNP) group in the sn3 position and a Bodipy fluorescein (FL) group in the sn2 position. Upon cleavage with Lp-PLA$_2$, the Bodipy F1 group is liberated and then may result in an increase in fluorescence. Inhibitors of Lp-PLA$_2$ therefore prevent this cleavage and no fluorescent increase is observed.

The PED6 assay was run as an unquenched 10 µL assay. Compounds source plate was prepared by making 1:3 (by volume) serial dilution of the compounds into pure DMSO on 384-well microplate. Then, 0.01 µL of compounds on compound source plate were transferred into 384 well Greiner 784076 (black) plates by ECHO liquid dispenser. 5 µL of recombinant human Lp-PLA$_2$ enzyme (2 nM rhLp-PLA$_2$ in assay buffer of 50 mM HEPES, pH7.4, 150 mM NaCl, 1 mM CHAPS) was added to each well of the plate with compounds. Plates were centrifuged for 10 sec at 500 rpm. After 30 minutes preincubation, 5 of substrate (4 µM PED6 [from 5 mM DMSO stock] in assay buffer of 50 mM HEPES, pH7.4, 150 mM NaCl, 1 mM CHAPS) was added to 384 well Greiner 784076 (black) plates. Plates were centrifuged for 10 sec at 500 rpm. Plate was covered to protect from light and incubated for 20 min at room temperature. Plates were read for fluorescence intensity at ex: 480/em: 540 using ViewLux microplate imager. PIC50 data, curve and QC analysis was conducted by using XL fit module in Excel.

All exemplified compounds of the present invention were tested according to the above assays or similar assay as described above and were found to demonstrate inhibition activity to Lp-PLA$_2$. The compounds described below were tested generally according to the PED6 assay described above. The pIC$_{50}$ value for each compound was either reported in at least one experiment or the average of multiple experiments. It is noted that the upper limit for pIC$_{50}$ obtained in the PED6 assay described above is 9.3. If a refined assay is used, compounds that exhibit pIC$_{50}$ equal to 9.3 in the PED6 assay described above may demonstrate pIC$_{50}$ higher than 9.3.

The pIC$_{50}$ values in the PED6 assay for all tested compounds were at least 5.0.

The pIC$_{50}$ values in the PED6 assay for all compounds except examples 23, 25, 26, 28, 61-63, 67, 70 were at least 8.0.

The pIC$_{50}$ values in the PED6 assay for examples 1, 4, 5, 8-12, 17, 18, 31, 32, 33, 41, 45, 46, 47, 53, 59, 60, 66, 69, 71 and 72 were at least 9.0.

(2) PLA2 VIIB Assay

PLA2 VIIB (also known as Novel Serine Dependent Lipase, NSDL) is a serine hydrolase with 40% amino acid identity with human Lp-PLA$_2$. Sequence comparisons indicate that the PLA VIIB active site catalytic triad positions are similar to those of Lp-PLA$_2$. Similar to Lp-PLA$_2$, it is capable of hydrolyzing oxidatively modified phospholipids and may be assayed using known Lp-PLA$_2$ substrates.

Upon cleavage by a phopholipase, it liberates a fluorescent Bodipy group. Recombinant human PLA2 VIIB is used as the phospholipase source in this assay, and compounds are screened to test their degree of inhibition in this assay. The assay is used to determine the degree of selectivity of the testing compounds between PLA2 VIIB and Lp-PLA$_2$.

The PLA2 VIIB assay was applied as an unquenched 10 µL assay. Compounds source plate is prepared by making 1:3 (by volume) serial dilution of the compounds into pure DMSO on 384-well microplate, 0.01 µL of compounds on compound source plate were transferred into 384 well Greiner 784076 (black) plates—by ECHO liquid dispenser. 5 µL of Novel Serine Dependent Lipase (NSDL) enzyme (5 nM NSDL in assay buffer of 50 mM HEPES, pH 7.4, 150 mM NaCl, 1 mM CHAPS) was added to each well with compounds. Plates were centrifuged for 10 sec at 500 rpm. After 30 minutes preincubation, 5 µL of substrate (5 µM PED6 [from 5 mM DMSO stock] in assay buffer of 50 mM HEPES, pH7.4, 150 mM NaCl, 1 mM CHAPS) was added to 384 well Greiner 784076 (black) low-volume plates by BRAVO liquid handling station. Plates were kinetic read by starting read immediately after PED6 addition at ex: 480/em: 540 using ViewLux microplate reader. pIC50 data, curve and QC analysis was conducted using XLfit module in Excel.

All exemplified compounds of the present invention were tested in PLA2 VIIB assay or similar assay as described above. All tested compounds except Examples 39, 40, 63 and 67 had over 100 fold selectivity between human recombinant Lp-PLA$_2$ and PLA2 VIIB.

(3) Lipoprotein-Associated Phospholipase A2 (Lp-PLA$_2$) Human Plasma Assay (Also Referred to as "Thio-PAF Assay")

The human plasma assay utilizes a thioester analog of PAF (phosphatidylcholine), where hydrolysis yields to the formation of a phospholipid containing a free thiol group. The amount of thiol is quantitated continuously by reacting with CPM (7-diethylamino-3-(4'-maleimidylphenyl)-4-methylcoumarin), a maleimide which increases in fluoresence after Michael addition of thiols. This assay may detect the activity of Lp-PLA$_2$ from plasma, as determined by specific inhibition by Lp-PLA$_2$ inhibitors.

The thio-PAF assay was run as a quenched 15 µL assay. Compounds source plate was prepared by making 1:3 (by volume) serial dilution of the compounds into pure DMSO on 384-well microplate. 0.01 µL of compounds on compound source plate were transferred to 384 well Greiner 784076 (black) low-volume plates by ECHO liquid dispenser. 8 µL pooled human plasma, which was previously aliquoted and frozen, was added. Plates were centrifuged for 10 sec at 500 rpm. After 30 minutes preincubation, 2 µL of substrate (2.5 mM thio-PAF, 3.2 mM NEM (N-ethylmaleimide) [made fresh daily in DMSO], and 32 µM CPM [from a DMSO stock] in assay buffer of 50 mM HEPES, pH7.4, 150 mM NaCl, 1 mM CHAPS was added to 384 well Greiner 784076 (black) low-volume plates by BRAVO liquid handling station. Plates were centrifuged for 10 sec at 500 rpm. Plate was covered to protect from light and incubated for 2 min at room temperature. Reaction was quenched with 5 µL of 5% aqueous trifluoroacetic acid (TFA). Plates were covered to protect from light and incubated for 40 min at room temperature. Plates were read at ex: 380/em: 485 using-Envision microplate reader. PIC50 data, curve and QC analysis was conducted by using XLFit module in Excel.

All exemplified compounds of the present invention were tested in thio-PAF assay or similar assay as described above.

The pIC$_{50}$ values in the thio-PAF assay for all compounds except examples 3 and 23 were at least 5.0.

The pIC$_{50}$ values in the thio-PAF assay for examples 1, 2, 4-22, 24, 29-34, 36-55, 57-60, 64-67, and 69-72 were at least 6.0.

The pIC$_{50}$ values in the thio-PAF assay for examples 2, 4, 6-12, 14-19, 29-34, 36-47, 50, 51, 53-55, 57-60, 66, 69, 71 and 72 were at least 7.0.

E. METHODS OF USE

The compounds of this invention are inhibitors of Lp-PLA$_2$. Therefore, these compounds may be used in therapy, for example, in the treatment of disorders associated with the activity of Lp-PLA$_2$. Accordingly, another aspect of the invention is directed to methods of treating conditions associated with the activity of Lp-PLA$_2$. As will be appreciated by those skilled in the art, a particular condition or its treatment may involve one or more underlying mechanisms associated with Lp-PLA$_2$ activity, including one or more of the mechanisms described herein.

In some embodiments, an inhibitor of Lp-PLA$_2$ according to the invention may be used in treating any of the disorders disclosed in the following published patent applications; WO96/13484, WO96/19451, WO97/02242, WO97/12963, WO97/21675, WO97/21676, WO 97/41098, WO97/41099, WO99/24420, WO00/10980, WO00/66566, WO00/66567, WO00/68208, WO01/60805, WO02/30904, WO02/30911, WO03/015786, WO03/016287, WO03/041712, WO03/042179, WO03/042206, WO03/042218, WO03/086400, WO03/87088, WO08/048,867, US 2008/0103156, US 2008/0090851, US 2008/0090852, WO08/048,866, WO05/003118 CA 2530816A1), WO06/063811, WO06/063813, WO 2008/141176, JP 200188847, US 2008/0279846 A1, US 2010/0239565 A1, and US 2008/0280829 A1.

In one embodiment, the compounds of this invention may be used to treat any disease that involves endothelial dysfunction, for example, atherosclerosis, (e.g. peripheral vascular atherosclerosis and cerebrovascular atherosclerosis), diabetes, hypertension, angina pectoris and after ischaemia and reperfusion.

In one embodiment, the compounds of the present invention may be used to treat any disease that involves lipid oxidation in conjunction with enzyme activity, for example, in addition to conditions such as atherosclerosis and diabetes, other conditions such as rheumatoid arthritis, stroke, inflammatory conditions of the brain such as Alzheimer's Disease, various neuropsychiatric disorders such as schizophrenia, myocardial infarction, ischemia, reperfusion injury, sepsis, and acute and chronic inflammation.

In one embodiment, the compounds of the present invention may be used to treat disease that involves activated monocytes, macrophages or lymphocytes, as all of these cell types express Lp-PLA$_2$ including diseases involving activated macrophages such as M1, dendritic and/or other macrophages which generate oxidative stress; exemplary disorder includes, but are not limited to, psoriasis, rheumatoid arthritis, wound healing chronic obstructive pulmonary disease (COPD) liver cirrhosis, atopic dermatitis, pulmonary emphysema, chronic pancreatitis, chronic gastritis, aortic aneurysm, atherosclerosis, multiple sclerosis, Alzheimer's disease, and autoimmune diseases such as lupus.

In one embodiment, the present invention provides methods of treating a disease associated with the activity of Lp-PLA$_2$, which comprises treating a subject in need thereof with a therapeutically effective amount of an inhibitor of Lp-PLA$_2$. The disease may be associated with the increased involvement of monocytes, macrophages or lymphocytes; with the formation of lysophosphatidylcholine and oxidized free fatty acids; with lipid oxidation in conjunction with Lp-PLA$_2$ activity; or with endothelial dysfunction.

In other embodiments, the compounds of the invention may be used for the primary or secondary prevention of acute coronary events, e.g. caused by atherosclerosis; adjunctive therapy in the prevention of restenosis; or delaying the progression of diabetic or hypertensive renal insufficiency. Prevention includes treating a subject at risk of having such conditions.

In certain embodiment, the compounds of the present invention may be used to treat the disease described herein in combination with an anti-hyperlipidaemic, anti-atherosclerotic, anti-diabetic, anti-anginal, anti-inflammatory, or anti-hypertension agent or an agent for lowering Lipoprotein (a) (Lp(a)). Examples of the above include, but are not limited to, cholesterol synthesis inhibitors such as statins, anti-oxidants such as probucol, insulin sensitizers, calcium channel antagonists, and anti-inflammatory drugs such as non-steroidal anti-inflammatory Drugs (NSAIDs). Examples of agents for lowering Lp(a) include the aminophosphonates described in WO 97/02037, WO 98/28310, WO 98/28311 and WO 98/28312.

In one embodiment, the compounds of the present invention may be used with statin. The statins are a well-known class of cholesterol lowering agents and include atorvastatin, simvarstatin, pravastatin, cerivastatin, fluvastatin, lovastatin and rosuvastatin. The two agents may be administered at substantially the same time or at different times, according to the discretion of the physician.

In certain embodiment, the compounds of the present invention may be used with an anti-diabetic agent or an insulin sensitizer. In one embodiment, a compound of the present invention may be used with PPAR gamma activators, for instance GI262570 (GlaxoSmithKline) and the glitazone class of compounds such as rosiglitazone, troglitazone and pioglitazone.

In one embodiment, the compounds of the present invention may be used to treat a neurodegeneration disease in a subject. The methods comprise administering to a subject in need thereof a pharmaceutical composition comprising an agent that inhibits the activity of Lp-PLA$_2$. Exemplary neurodegeneration diseases include, but are not limited to, Alzheimer's disease, vascular dementia, Parkinson's disease and Huntington's disease. In certain embodiment, the neurodegeneration disease described herein is associated with an abnormal blood brain barrier. In one embodiment, the subject administered an agent that inhibits the activity of Lp-PLA$_2$ is a human.

In one embodiment, the present invention provides methods of treating a subject with or at risk of vascular dementia. The methods comprise administering to the subject a pharmaceutical composition comprising a safe and effective amount of a compound of present invention. In certain embodiment, the vascular dementia is associated with Alzheimer's disease.

In one embodiment, the present invention provides methods of treating a neurological disorder associated with an abnormal blood brain barrier (BBB) function, inflammation, and/or microglia activation in a subject in need thereof. The methods comprise administering to the subject a safe and effective amount of a compound of present invention. In certain embodiment, the abnormal blood-brain barrier is a permeable blood brain barrier. In one embodiment, the disease is a neurodegeneration disease. Such neurodegeneration diseases are, for example, but are not limited to, vascular dementia, Alzheimer's disease, Parkinson's disease and Huntington's disease. In certain embodiment, the present invention provides methods of treating disease associated with a subject with blood brain barrier (BBB) leakage. Exemplary disease include, but is not limited to, brain hemorrhage, cerebral amyloid angiopathy. In one embodiment, the neurodegeneration disease is Alzheimer's disease. In certain embodiment, the neurodegeneration disease is vascular dementia. In one embodiment, the neurodegeneration disease is Multiple Sclerosis (MS).

In one embodiment, the present invention provides methods of decreasing beta amyloid, referred to as "Aβ" accumulation in the brain of a subject. The methods comprise administering to a subject in need thereof a pharmaceutical composition comprising a safe and effective amount of a compound of the present invention. In certain embodiment, the beta amyloid is Abeta-42.

In certain embodiment, when a subject is administered a safe and effective amount of a compound of the present invention, the methods may further comprise administering to the subject another therapeutic agent that may be useful in treating the neurodegenerative disease for which the subject is being treated, or that may be a co-morbidity. For example, when the neurodegenerative disease is similar to Alzheimer's disease, the subject may be treated with other agents targeting Alzheimer's disease such as ARICEPT® or donepezil, COGNEX® or tacrine, EXELON® or rivastigmine, REMINYL® or galantamine, anti-amyloid vaccine, Abeta-lowering therapies, mental exercise or stimulation.

In one embodiment, the present invention relates to methods of treating metabolic bone diseases by administering to the subject in need thereof a safe and effective amount of a compound of the present invention. Exemplary metabolic bone diseases include, diseases associated with loss of bone mass and density including, but are not limited to, osteoporosis and osteopenic related diseases. Exemplary osteoporosis and osteopenic related diseases include, but are not limited to, bone marrow abnormalities, dyslipidemia, Paget's diseases, type II diseases, metabolic syndrome, insulin resistance, hyperparathyroidism and related diseases. In certain embodiment, the subject in need thereof is a human.

It is believed that methods of preventing osteoporosis and/or osteopenic diseases described herein may be affected by inhibiting the expression of Lp-PLA$_2$ and/or inhibiting the protein activity of Lp-PLA$_2$. Accordingly, some embodiments of the present invention provide methods for inhibiting Lp-PLA$_2$ by blocking enzyme activity. In one embodiment, methods for inhibiting Lp-PLA$_2$ by reducing and/or down-regulating the expression of Lp-PLA$_2$ RNA are provided. In certain embodiment, preventing and/or reducing loss of bone mass and/or loss of bone density leads to preventing or reducing symptoms associated with metabolic bone diseases such as osteoporosis and/or osteopenic diseases.

In one embodiment, the methods further comprise administering to a subject in need thereof additional therapeutic agents used in the treatment of metabolic bone diseases. For example, when the metabolic bone disease is osteoporosis additional therapeutic agents such as bisphosphates (e.g., alendronate, ibandromate, risedronate, calcitonin, raloxifene, a selective estrogen modulator (SERM), estrogen therapy, hormone replacement therapy (ET/HRT) and teriparatide) may be used.

One aspect of the present invention provides methods for treating eye diseases by administering a safe and effective amount of a compound of present invention. Eye diseases applicable in the present invention may be associated with the breakdown of the inner blood-retinal barrier (iBRB). Exemplary eye diseases relate to diabetic eye diseases and disorders include macular edema, diabetic retinopathy, and the like. Further, in one embodiment, the present invention relates to methods for treating eye diseases by administering a compound of the present invention to inhibit Lp-PLA$_2$. Exemplary eye diseases include, but are not limited to, central retinal vein occlusion, branched retinal vein occlusion, Irvine-Gass syndrome (post cataract and post-surgical), retinitis pigmentosa, pars planitis, birdshot retinochoroidopathy, epiretinal membrane, choroidal tumors, cystic macular edema, parafoveal telengiectasis, tractional maculopathies, vitreomacular traction syndromes, retinal detachment, neuroretinitis, idiopathic macular edema, and the like.

Further, some embodiments of the present invention provide methods for treating diabetic macular edema in a subject. The method comprises administering to a subject in need thereof a safe and effective amount of a compound of present invention.

In one embodiment, the present invention provides methods of treating a subject with or at risk of macular edema. The methods comprise administering to the subject a safe and effective amount of a compound of the present invention. In certain embodiment, the macular edema is associated with diabetic eye disease, for example, diabetic retinopathy. In one embodiment, the macular edema is associated with posterior uveitis.

In one embodiment, the present invention provides methods of treating glaucoma or macular degeneration. The methods comprise administering to the subject a safe and effective amount of a compound of the present invention.

In one embodiment, the present invention provides methods of treating a disease associated with the breakdown of the inner blood-retinal barrier in a subject in need thereof. The methods comprise administering to the subject a safe and effective amount of a compound of the present invention.

In one embodiment, systemic inflammatory diseases such as, juvenile rheumatoid arthritis, inflammatory bowel disease, Kawasaki disease, multiple sclerosis, sarcoidosis, polyarteritis, psoriatic arthritis, reactive arthritis, systemic lupus erythematosus, Vogt-Koyanagi-Harada syndrome, Lyme disease, Bechet's disease, ankylosing sponsylitis, chronic granulomatous disease, enthesitis, may be the underlying cause of posterior uveitis affecting the retina, and which can result in macula edema. The present invention relates to methods for treating posterior uveitis or any of these systemic inflammatory diseases by administering a safe and effective amount of a compound of the present invention.

It is believed that Lp-PLA$_2$ inhibitors may have beneficial effects on indications associated with M1/M2 macrophage polarization. The belief is based on the following studies. A study was carried out by GSK to investigate the relationship between M1/M2 macrophage polarization and different diseases. 94 human markers described in Martinez F O et al., distinguishing M1 and M2-phenotypes was used against a GSK subscribed GeneLogic database. (See Martinez F O et al. (2006) J Immunol 177, 7303-7311.) The Connectivity Map methodology described in Lamb J et al. was used to identify the fraction of samples in each disease state having expression characteristics consistent with a M1-favoring or M2-favoring macrophage population. (See Lamb J et al. (2006) Science 313, 1929-1935) (PMID 17008526)). The study showed that liver cirrhosis, skin psoriasis, atopic dermatitis, pulmonary emphysema, chronic pancreatitis, chronic gastritis, aortic aneurysm have M1/M2 imbalance.

A further study was carried out to study the impact of Lp-PLA$_2$ inhibitors on modulating M1/M2 imbalance. In this study, rats were induced to develop experimental autoimmune encephalomyelitis (EAE) by immunization with myelin basic protein (MBP) antigen and treated with a known Lp-PLA$_2$ inhibitor: 5-((9-Methoxy-4-oxo-6,7-dihydro-4H-pyrimido[6,1-a]isoquinolin-2-yl)oxy)-2-(3-(trifluoromethyl)phenoxy)benzonitrile (See PCT application no. PCT/CN2011/001597) For preventive treatment, compound administration started at day 0 whereas it started at 7 day in therapeutic treatment. Rats were subsequently monitored for symptoms of EAE. Rats were immunized with MBP to develop EAE and symptoms were monitored daily. Plasma Lp-PLA$_2$ activity and LysoPC concentration were determined at different time points through the course of EAE.

Ex vivo analysis of proinflammatory (M1) and anti-inflammatory (M2) markers in control and compound treated EAE mice. Splenic macrophages were harvested at day 13 post MBP-immunization and assayed for expression of a variety of markers by realtime PCR. CNS infiltrating cells were harvested and macrophages were analyzed for expression of M1 and M2 markers by realtime PCR. Treatment with compound resulted in the decrease in M1 markers and increase in M2 markers, which potentially indicated the possibility of anti-inflammation and tissue repair.

Therefore, in one embodiment, the present invention provides methods of treating disease associated with macrophage polarization, particularly M1/M2 macrophage polarization. Exemplary diseases associated with macrophage polarization are, but not limited to, liver cirrhosis, skin psoriasis, atopic dermatitis, pulmonary emphysema, chronic pancreatitis, chronic gastritis, aortic aneurysm, atherosclerosis, multiple sclerosis, and other autoimmune diseases that are associated with macrophage polarization.

One aspect of the present invention provides the use of a compound of the present invention for the preparation of a medicament for carrying out a method described herein. Another aspect of the present invention provides a compound of the present invention for use in carrying out methods of treatment described herein.

F. COMPOSITION

The compounds of the present invention may be formulated into pharmaceutical compositions prior to administration to a subject. Accordingly, one aspect of the invention is directed to pharmaceutical compositions comprising a compound of the invention and one or more pharmaceutically-acceptable excipients. In accordance with another aspect of the invention, a process for the preparation of a pharmaceutical composition including admixing a compound of the Formula (I) or Formula (LA) or salts thereof, solvates etc thereof, with one or more pharmaceutically acceptable excipients.

Pharmaceutical compositions may be presented in unit dose forms containing a predetermined amount of active ingredient per unit dose. Such a unit may contain, for example 0.5 mg to 1 g, preferably 1 mg to 700 mg, more preferably 5 mg to 100 mg of a compound of the Formula (I) or Formula (IA) or salts thereof, solvates etc thereof, depending on the condition being treated, the route of administration and the age, weight and condition of the patient, or pharmaceutical compositions may be presented in unit dose forms containing a predetermined amount of active ingredient per unit dose. In one embodiment, the unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or nonaqueous liquids; edible foams or whips; or oil-in-water liquid emulsions or water-in-oil liquid emulsions.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of the Formula (I) or Formula (IA) or salts thereof, solvates etc thereof for the treatment of anemia will generally be in the range of 0.1 to 100 mg/kg body weight of recipient per day and more usually in the range of 1 to 10 mg/kg body weight per day. Thus, for a 70 kg adult mammal, the actual amount per day would usually be from 70 to 700 mg and this amount may be given in a single dose per day or in a number of sub-doses per day as such as two, three, four, five or six doses per day. Or the dosing can be done intermittently, such as once every other day, once a week or once a month. An effective amount of a salt or solvate, etc., may be determined as a proportion of the effective amount of the compound of formula (I) per se. It is envisaged that similar dosages would be appropriate for treatment of the other conditions referred to above.

The pharmaceutical compositions of the invention may contain one compound of the invention. In one embodiment, the pharmaceutical compositions may contain more than one compound of the invention. For example, in certain embodiment, the pharmaceutical compositions may contain two compounds of the invention. In addition, the pharmaceutical compositions may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient may be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided.

The compounds of the invention and the pharmaceutically-acceptable excipient or excipients may be formulated into a dosage form adapted for administration to the subject by the desired route of administration. For example, dosage forms include those adapted for (1) oral administration (including buccal or sublingual) such as tablets, capsules, caplets, pills, troches, powders, syrups, elixers, suspensions, solutions, emulsions, sachets, and cachets; (2) parenteral administration (including subcutaneous, intramuscular, intravenous or intradermal) such as sterile solutions, suspensions, and powders for reconstitution; (3) transdermal administration such as transdermal patches; (4) rectal administration such as suppositories; (5) nasal inhalation such as dry powders, aerosols, suspensions, and solutions; and (6) topical administration (including buccal, sublingual or transdermal) such as creams, ointments, lotions, solutions, pastes, sprays, foams, and gels. Such compositions may be prepared by any method known in the art of pharmacy, for example by bringing into association a compound of Formal (I) with the carrier(s) or excipient(s).

Pharmaceutical compositions adapted for oral administration may be presented as discrete units such as capsules or tablets; powders or granules; solutions or suspensions in aqueous or nonaqueous liquids; edible foams or whips; or oil-in-water liquid emulsions or water-in-oil liquid emulsions.

Suitable pharmaceutically-acceptable excipients may vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate carrying or transporting of the compound or compounds of the invention once administered to the subject from an organ, or a portion of the body, to another organ, or a portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharma-* ceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

What is claimed is:

1. A compound of Formula (I) or a pharmaceutically acceptable salt thereof

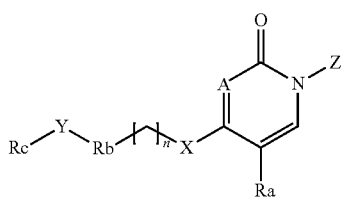

wherein:
A is N or CH;
n is 1 or 2;
X is O, $CH_2$ or NH;
when A is N, Y is absent, O or $CH_2$ or when A is CH, Y is O;
Z is H, $C_1$-$C_3$alkyl, —($C_1$-$C_3$alkyl)-heteroaryl wherein said heteroaryl is optionally substituted with one or more substituents independently selected from the group consisting of $C_1$-$C_3$alkyl and $C_1$-$C_3$alkoxyl;
Ra is H, F, Cl, or $C_1$-$C_3$alkyl;
Rb is phenyl or heteroaryl, either of which is optionally substituted with one or more substituents independently selected from the group consisting of CN and halo; and
Rc is phenyl or heteroaryl, wherein either of phenyl or heteroaryl is optionally substituted with one or more substituents independently selected from the group consisting of halo, $C_1$-$C_3$alkyl, and $C_1$-$C_3$haloalkyl.

2. The compound according to claim 1, wherein A is N.

3. The compound according to claim 1, wherein n is 1 or 2.

4. The compound according to claim 1, wherein X is O.

5. The compound according to claim 1, wherein Y is O.

6. The compound according to claim 1, wherein Z is —$CH_2$-heteroaryl, wherein said heteroaryl is selected from the group consisting of pyridinyl, pyrazolyl, pyrimidinyl, and the heteroaryl is optionally substituted with one or more substituents independently selected from the group consisting of $CH_2$ and —$OCH_3$.

7. The compound according to claim 1, wherein Ra is H.

8. The compound according to claim 1, wherein Rb is phenyl optionally substituted with one or more substituents independently selected from the group consisting of CN and F.

9. The compound according to claim 1, wherein Rc is phenyl optionally substituted with one or more substituents independently selected from the group consisting or F.

10. The compound according to claim 1, wherein
A is N;
n is 1 or 2;
X is O;
Y is O;
Z is —$CH_2$-heteroaryl, wherein said heteroaryl is selected from the group consisting of pyridinyl, pyrazolyl, pyrimidinyl, and the heteroaryl is optionally substituted with one or more substituents independently selected from the group consisting of $CH_3$ and —$OCH_3$;
Ra is H, F or Cl;
Rb is phenyl optionally substituted with one or more substituents independently selected from the group consisting of CN and F; and
Rc is phenyl optionally substituted with one or more substituents independently selected from the group consisting of F, Cl, $CH_3$ and $CF_3$.

11. A pharmaceutical composition comprising a compound of Formula (I) according to claim 1 and a pharmaceutically acceptable carrier.

12. A method for treating Alzheimer's disease in a subject comprising administering to a subject in need thereof a safe and effective amount of a compound of Formula (I) or a pharmaceutically acceptable salt thereof according to claim 1.

13. A method for treating atherosclerosis in a subject comprising administering to a subject in need thereof a safe and effective amount of a compound of Formula (I) or a pharmaceutically acceptable salt thereof according to claim 1.

* * * * *